US010077221B2

(12) United States Patent
Bonnet et al.

(10) Patent No.: US 10,077,221 B2
(45) Date of Patent: *Sep. 18, 2018

(54) COMPOSITION COMPRISING HF AND E-3,3,3-TRIFLUORO-1-CHLOROPROPENE

(71) Applicant: ARKEMA FRANCE, Colombes (FR)

(72) Inventors: Philippe Bonnet, Lyons (FR); Bertrand Collier, Saint-Genis-Laval (FR); Dominique Deur-Bert, Charly (FR); Laurent Wendlinger, Soucieu en Jarrest (FR)

(73) Assignee: ARKEMA FRANCE, Colombes (FR)

( * ) Notice: Subject to any disclaimer, the term of this patent is extended or adjusted under 35 U.S.C. 154(b) by 175 days.

This patent is subject to a terminal disclaimer.

(21) Appl. No.: 14/774,161

(22) PCT Filed: Feb. 21, 2014

(86) PCT No.: PCT/FR2014/050364
§ 371 (c)(1),
(2) Date: Sep. 10, 2015

(87) PCT Pub. No.: WO2014/147311
PCT Pub. Date: Sep. 25, 2014

(65) Prior Publication Data
US 2016/0023974 A1 Jan. 28, 2016

(30) Foreign Application Priority Data
Mar. 20, 2013 (FR) ..................................... 13 52483

(51) Int. Cl.
*C07C 21/18* (2006.01)
*C01B 7/19* (2006.01)
*C09K 3/30* (2006.01)
*C09K 5/04* (2006.01)

(52) U.S. Cl.
CPC .............. *C07C 21/18* (2013.01); *C01B 7/191* (2013.01); *C09K 3/30* (2013.01); *C09K 5/044* (2013.01)

(58) Field of Classification Search
None
See application file for complete search history.

(56) References Cited

U.S. PATENT DOCUMENTS 6,013,846 A * 1/2000 Wismer .................. C07C 17/00 570/164
6,646,020 B2 11/2003 Nyberg et al.
6,814,884 B2 11/2004 Jannick et al.
7,438,826 B1 10/2008 Chen et al.
7,442,321 B1 10/2008 Chen et al.
8,323,524 B2 12/2012 Flynn et al.
8,450,537 B2 * 5/2013 Rao ......................... C07C 17/10 570/156
8,541,478 B2 9/2013 Singh et al.
2004/0180978 A1 9/2004 Dreir
2005/0156135 A1 7/2005 Minor et al.
2005/0285079 A1 12/2005 Minor
2006/0142173 A1 6/2006 Johnson et al.
2006/0266976 A1 11/2006 Minor et al.
2007/0100173 A1 * 5/2007 Miller ..................... C01B 7/191 570/178
2007/0100175 A1 * 5/2007 Miller ..................... C01B 7/196 570/178
2007/0145325 A1 6/2007 Minor
2008/0051612 A1 * 2/2008 Knapp .................... C07C 17/25 570/178
2008/0098755 A1 5/2008 Singh et al.
2008/0125505 A1 5/2008 Bowman et al.
2009/0095014 A1 4/2009 Sun et al.
2009/0099274 A1 4/2009 Van Der Puy
2009/0127496 A1 * 5/2009 Rao ........................ B01J 27/125 252/67
2009/0253820 A1 10/2009 Bowman et al.
2009/0305876 A1 12/2009 Singh et al.
2009/0318323 A1 12/2009 Johnson et al.
(Continued)

FOREIGN PATENT DOCUMENTS

EP 0 940 382 A1 9/1999
JP S62-225860 A 10/1987
(Continued)

OTHER PUBLICATIONS

Official Action issued in JP 2011-531537, dated Jan. 20, 2016, 7 pages, Japan Patent Office, JP.
Official Action issued in JP 2015-026010, dated Mar. 1, 2016, 6 pages (3 pages JP OA; 3 pages Machine English-language translation), Japanese Patent Office, JP.
International Search Report (PCT/ISA/210) dated Jun. 6, 2014, by the European Patent Office as the International Searching Authority for International Application No. PCT/FR2014/050364.
U.S. Appl. No. 14/987,347, Pigamo, et al.
(Continued)

*Primary Examiner* — Joseph D Anthony
(74) *Attorney, Agent, or Firm* — Buchanan Ingersoll & Rooney P.C.

(57) ABSTRACT

An azeotropic or quasi-azeotropic composition including hydrogen fluoride, E-3,3,3-trifluoro-1-chloropropene and optionally one or more (hydro)halogen-carbon compounds including between 1 and 3 carbon atoms. Also, a preferred azeotropic or quasi-azeotropic composition including hydrogen fluoride, E-3,3,3-trifluoro-1-chloropropene, and optionally one or more compounds selected from among 1,1,1,2,2-pentafluoropropane, 2,3,3,3-tetrafluoropropene, 3,3,3-trifluoropropene, 3,3,3-trifluoro-2-chloropropene, 1,3,3,3-tetrafluoropropene, trifluoropropyne, 1,1,1,3,3-pentafluoropropane, 1,1,1,3,3-pentafluoropropane, 1,1,1,3,3-pentafluoropropene, 1,1,1,2,3-pentafluoropropene and 2-chloro,1,1,1,2-tetrafluoropropane.

15 Claims, No Drawings

(56) References Cited

U.S. PATENT DOCUMENTS

| | | | | |
|---|---|---|---|---|
| 2010/0004155 | A1 | 1/2010 | Ishihara et al. | |
| 2010/0072415 | A1* | 3/2010 | Rao | B01J 23/26 252/67 |
| 2010/0102273 | A1 | 4/2010 | Basu et al. | |
| 2010/0105788 | A1 | 4/2010 | Chen et al. | |
| 2010/0113629 | A1 | 5/2010 | Van Horn et al. | |
| 2010/0187088 | A1* | 7/2010 | Merkel | B01D 3/36 203/50 |
| 2010/0237279 | A1* | 9/2010 | Hulse | C07C 17/206 252/182.12 |
| 2011/0041529 | A1 | 2/2011 | Chen et al. | |
| 2011/0112340 | A1* | 5/2011 | Smith | C07C 17/04 570/169 |
| 2011/0197602 | A1 | 8/2011 | Abbas et al. | |
| 2011/0218369 | A1* | 9/2011 | Elsheikh | C07C 17/206 570/151 |
| 2011/0309287 | A1 | 12/2011 | Chen et al. | |
| 2011/0309288 | A1 | 12/2011 | Chen et al. | |
| 2011/0315915 | A1 | 12/2011 | Abbas et al. | |
| 2012/0041239 | A1* | 2/2012 | Suzuki | C07C 17/206 570/160 |
| 2012/0053369 | A1* | 3/2012 | Hulse | C07C 17/206 570/135 |
| 2012/0053372 | A1 | 3/2012 | Hulse et al. | |
| 2012/0056122 | A1* | 3/2012 | Hulse | C01B 7/191 252/67 |
| 2012/0138841 | A1* | 6/2012 | Hulse | A62D 1/0057 252/2 |
| 2012/0138847 | A1 | 6/2012 | Van Horn et al. | |
| 2012/0145955 | A1 | 6/2012 | Abbas et al. | |
| 2012/0222448 | A1* | 9/2012 | Chaki | C07C 17/383 62/617 |
| 2012/0329893 | A1 | 12/2012 | Abbas | |
| 2013/0037058 | A1 | 2/2013 | Abbas | |
| 2013/0105296 | A1* | 5/2013 | Chaki | C01B 7/196 203/60 |
| 2013/0231399 | A9 | 9/2013 | Basu et al. | |
| 2014/0012052 | A1* | 1/2014 | Pham | C07C 17/38 570/160 |
| 2015/0152235 | A1 | 6/2015 | Abbas | |
| 2016/0009555 | A1* | 1/2016 | Bonnet | C07C 21/18 252/182.12 |
| 2016/0023176 | A1* | 1/2016 | Bonnet | C01B 7/191 51/307 |
| 2016/0023974 | A1* | 1/2016 | Bonnet | C07C 21/18 252/182.12 |
| 2016/0031773 | A1* | 2/2016 | Bonnet | C01B 7/195 252/182.12 |
| 2016/0046548 | A1* | 2/2016 | Bonnet | C01B 7/19 252/182.12 |
| 2016/0115104 | A1 | 4/2016 | Pigamo et al. | |

FOREIGN PATENT DOCUMENTS

| | | | |
|---|---|---|---|
| JP | H03-168566 | A | 7/1991 |
| JP | H04-110388 | A | 4/1992 |
| JP | H06-272978 | A | 9/1994 |
| JP | 2002-501035 | A | 1/2002 |
| JP | 2008-133438 | A | 6/2008 |
| JP | 2008-524433 | A | 7/2008 |
| JP | 2011-037912 | A | 2/2011 |
| JP | 2011-510119 | A | 3/2011 |
| JP | 2012-506944 | A | 3/2012 |
| WO | WO 99/37598 | A1 | 7/1999 |
| WO | WO 02/40613 | A1 | 5/2002 |
| WO | WO 2004/037913 | A2 | 5/2004 |
| WO | WO 2004/037913 | A3 | 5/2004 |
| WO | WO 2006/069362 | A2 | 6/2006 |
| WO | WO 2006/069362 | A3 | 6/2006 |
| WO | WO 2007/002625 | A2 | 1/2007 |
| WO | WO 2007/002625 | A3 | 1/2007 |
| WO | WO 2007/053736 | A2 | 5/2007 |
| WO | WO 2008/002500 | A1 | 1/2008 |
| WO | WO 2009/089511 | A2 | 7/2009 |
| WO | WO 2009/089511 | A3 | 7/2009 |
| WO | WO 2009/140231 | A2 | 11/2009 |
| WO | WO 2010/043807 | A1 | 4/2010 |
| WO | WO 2010/059493 | A1 | 5/2010 |
| WO | WO 2010/062572 | A2 | 6/2010 |
| WO | WO 2010/062572 | A3 | 6/2010 |
| WO | WO 2010/085397 | A1 | 7/2010 |
| WO | WO 2010/088196 | A2 | 8/2010 |
| WO | WO 2012/075283 | A2 | 6/2012 |
| WO | WO 2014/147310 | A1 | 9/2014 |
| WO | WO 2014/147312 | A1 | 9/2014 |
| WO | WO 2014/147313 | A1 | 9/2014 |
| WO | WO 2014/147314 | A1 | 9/2014 |

OTHER PUBLICATIONS

Pigamo, Anne, et al., U.S. Appl. No. 14/987,347 entitled "E-1,Chloro-3,3,3-Trifluoropropene Production Process from 1,1,3,3-Tetrachloropropene," filed Jan. 4, 2016.

Forane Blwoing Agents by Arkema, Technical Profile Forane© 1233zd, copyright 2013, Arkema, King of Prussia, PA, www.forane.com, retrieved Jun. 2017, 6 pages.

U.S. Appl. No. 15/809,477, Pigamo, et al.

U.S. Appl. No. 15/575,980, Pigamo, et al.

Pigamo, Anne, et al., U.S. Appl. No. 15/809,477 entitled "E-1-Chloro-3,3,3-Trifluoropropene Production Process From 1,1,3,3-Tetrachloropropene", filed Nov. 10, 2017.

Pigamo, Anne, et al., U.S. Appl. No. 15/575,980 entitled "Compositions Based on 1,1,3,3-Tetrachloropropene", filed Nov. 21, 2017.

* cited by examiner

COMPOSITION COMPRISING HF AND E-3,3,3-TRIFLUORO-1-CHLOROPROPENE

The present invention relates to azeotropic or quasi-azeotropic compositions comprising E-3,3,3-trifluoro-1-chloropropene and hydrogen fluoride. These compositions may originate from intermediate compositions in the production of E-3,3,3-trifluoro-1-chloropropene and are generally useful in processes for recycling hydrogen fluoride.

The manufacture of E-3,3,3-trifluoro-1-chloropropene accompanied by a multitude of by-products, having a boiling point close to HCFO-1233zdE, leads to relatively complex and expensive purification steps. The difficulty encountered during the purification of HCFO-1233zdE generally implies an appreciable loss of desired product. Furthermore, these by-products may form azeotropic compositions with E-3,3,3-trifluoro-1-chloropropene, making separation by distillation simple, very difficult, or even impossible.

Fluids based on E-3,3,3-trifluoro-1-chloropropene have found numerous applications in varied industrial fields, especially as heat-transfer fluid, propellants, foaming agents, swelling agents, gaseous dielectrics, polymerization medium or monomer, support fluids, abrasive agents, drying agents and fluids for power production units.

Particular importance is given to fluids that have a low impact on the environment.

Following various experiments and trials, the Applicant has discovered that the compound E-3,3,3-trifluoro-1-chloropropene formed a heteroazeotropic or quasi-heteroazeotropic compound with hydrogen fluoride. It is difficult to identify novel fluids corresponding to these characteristics since azeotropes are not predictable.

The subject of the present invention is an azeotropic or quasi-azeotropic composition comprising hydrogen fluoride, E-3,3,3-trifluoro-1-chloropropene and optionally one or more (hydro)halocarbon compounds comprising between 1 and 3 carbon atoms.

According to one embodiment of the invention, the composition is heteroazeotropic or quasi-heteroazeotropic.

A heteroazeotropic or quasi-heteroazeotropic mixture is an azeotropic or quasi-azeotropic mixture in which the condensed liquid forms two immiscible solutions that can be readily separated, for example by decantation. This property is a considerable advantage for the recovery of HF.

The term "quasi-azeotropic" or "quasi-heteroazeotropic" has a broad meaning and is intended to include compositions that are strictly azeotropic or strictly heteroazeotropic and those that behave like an azeotropic or heteroazeotropic mixture.

A mixture is azeotropic when the pressure at the dew point is equal to that at the bubble formation point, which means that the vapor composition is equal to that of the condensed liquid.

A mixture is considered as quasi-azeotropic when the pressure at the dew point is substantially equal to that at the bubble formation point, which means that the vapor composition is substantially equal to that of the condensed liquid.

Another way of characterizing a mixture as quasi-azeotropic when the pressure difference between the pressure at the dew point and the pressure at the bubble formation point is low, preferentially less than or equal to 5%, on the basis of the pressure at the bubble formation point.

Compositions according to the invention especially concern the following compounds, the acronyms of which represent:

HF: hydrogen fluoride
HCC-40: chloromethane, or $CH_3Cl$
HCFC-115: chloropentafluoroethane, or $C_2F_5Cl$
HCFC-124: chlorotetrafluoroethane, or $C_2HF_4Cl$
HFC-125: pentafluoroethane, or $C_2HF_5$
HCFC-133a: 1-chloro-2,2,2-trifluoroethane, or $C_2H_2F_3Cl$
HFC-134a: 1,1,1,2-tetrafluoroethane, or $C_2H_2F_4$
HCFC-142b: 1-chloro-1,1-difluoroethane, or $C_2H_3F_2Cl$
HFC-143a: 1,1,1-trifluoroethane, or $C_2H_3F_3$
HFC-152a: 1,1-difluoroethane, or $C_2H_4F_2$
HFO-1132: 1,2-difluoroethylene, or $C_2H_2F_2$
HFO-1141: fluoroethylene, or $C_2H_3F$
HFO-1234yf: 2,3,3,3-tetrafluoropropene or $CH_2{=}CF{-}CF_3$
HFC-245cb: 1,1,1,2,2-pentafluoropropane or $CF_3{-}CF_2{-}CH_3$
HFO-1234zeE: E-1,3,3,3-tetrafluoropropene or E-$CF_3{-}CH{=}CHF$
HFO-1234zeZ: Z-1,3,3,3-tetrafluoropropene or Z—$CF_3{-}CH{=}CHF$
HFO-1243zf: 3,3,3-trifluoropropene or $CF_3{-}CH{=}CH_2$
HCFO-1233xf: 3,3,3-trifluoro-2-chloropropene or $CF_3{-}CCl{=}CH_2$
HCFO-1233zdE: E-3,3,3-trifluoro-1-chloropropene or E-$CF_3{-}CH{=}CHCl$
HCFO-1233zdZ: Z-3,3,3-trifluoro-1-chloropropene or Z—$CF_3{-}CH{=}CHCl$
HFO-1225yeZ: Z-1,1,1,2,3-pentafluoropropene or Z—$CHF{=}CF{-}CF_3$
HFO-1225yeE: E-1,1,1,2,3-pentafluoropropene or E-$CHF{=}CF{-}CF_3$
HFO-1225zc: 1,1,3,3,3-pentafluoropropene or $CF_2{=}CH{-}CF_3$
HFO-1225yc: 1,1,2,3,3-pentafluoropropene or $CF_2{=}CF{-}CF_2$
HCFC-1214: dichlorotetrafluoropropene, or $C_3F_4Cl_2$
HCFO-1215: chloropentafluoropropene, or $C_3F_5Cl$
HFO-1216: hexafluoropropene, or $C_3F_6$
HCFO-1223: dichlorotrifluoropropene, or $C_3HF_3Cl_2$
HCFO-1224: chlorotetrafluoropropene, or $C_3HF_4Cl$
HCFO-1232: dichlorodifluoropropene, or $C_3H_2F_2Cl_2$
HCFO-1233xc: 1,1,3-trifluoro-2-chloropropene or $CH_2F{-}CCl{=}CF_2$
HCFO-1233xe: 1,3,3-trifluoro-2-chloropropene or $CHF_2{-}CCl{=}CHF$
HCFO-1233yb: 1,2,3-trifluoro-1-chloropropene or $CH_2F{-}CF{=}CFCl$
HCFO-1233yc: 1,1,2-trifluoro-3-chloropropene or $CH_2Cl{-}CF{=}CF_2$
HCFO-1233yd: 2,3,3-trifluoro-1-chloropropene or $CHF_2{-}CF{=}CHCl$
HCFO-1233ye: 1,2,3-trifluoro-3-chloropropene or $CHClF{-}CF{=}CHF$
HCFO-1233yt 2,3,3-trifluoro-3-chloropropene or $CClF_2{-}CF{=}CH_2$
HCFO-1233zb: 1,3,3-trifluoro-1-chloropropene or $CHF_2{-}CH{=}CFCl$
HCFO-1233zc: 1,1,3-trifluoro-3-chloropropene or $CHClF{-}CH{=}CF_2$
HCFO-1233ze: 1,3,3-trifluoro-3-chloropropene or $CClF_2{-}CH{=}CHF$
HFO-1234yc: 1,1,2,3-tetrafluoropropene or $CF_2{=}CF{-}CH_2F$
HFO-1234ye: 1,2,3,3-tetrafluoropropene or $CHF{=}CF{-}CHF_2$
HFO-1234zc: 1,1,3,3-tetrafluoropropene or $CF_2{=}CH{-}CHF_2$ HCFO-1242: chlorodifluoropropene, or $C_3H_3F_2Cl$
HFO-1243yc: 1,1,2-trifluoropropene or $CH_3—CF═CF_2$
HFO-1243ye: 1,2,3-trifluoropropene or $CH_2F—CF═CHF$
HFO-1243yf: 2,3,3-trifluoropropene or $CHF_2—CF═CH_2$
HFO-1243zc: 1,1,3-trifluoropropene or $CH_2F—CH═CF_2$
HFO-1243ze: 1,3,3-trifluoropropene or $CHF_2—CH═CHF$
HCFO-1251: chlorofluoropropene, or $C_3H_4FCl$
HFO-1252: difluoropropene, or $C_3H_4F_2$
HFO-216: hexafluoropropene, or $C_3F_6Cl_2$
HCFO-217: chloroheptafluoropropane, or $C_3F_7Cl$
HFC-218: octafluoropropane, or $C_3F_8$
HCFC-225: dichloropentafluoropropane, or $C_3HF_5Cl_2$
HCFC-226: chlorohexafluoropropane, or $C_3HF_6Cl$
HFC-227: heptafluoropropane, or $C_3HF_7$
HCFC-234: dichlorotetrafluoropropane, or $C_3H_2F_4Cl_2$
HCFC-235: chloropentafluoropropane, or $C_3H_2F_5Cl$
HFC-236: hexafluoropropane, or $C_3H_2F_6$
HCFC-243: dichlorotrifluoropropane, or $C_3H_3F_3Cl_2$
HCFC-244: chlorotetrafluoropropane, or $C_3H_3F_4Cl$
HCFC-244bb: 2-chloro,1,1,1,2-tetrafluoropropane or $CF_3—CFCl—CH_3$
HFC-245fa: 1,1,1,3,3-pentafluoropropane or $CF_3—CH_2—CHF_2$
HFC-245ea: 1,1,2,3,3-pentafluoropropane or $CHF_2—CHF—CHF_2$
HFC-245eb: 1,1,1,2,3-pentafluoropropane or $CF_3—CHF—CH_2F$
HFC-245ca: 1,1,2,2,3-pentafluoropropane or $CHF_2—CF_2—CH_2F$
HCFC-253: chlorotrifluoropropane, or $C_3H_4F_3Cl$
HFC-254: tetrafluoropropane, or $C_3H_4F_4$
HCFC-262: Chlorodifluoropropane, or $C_3H_5F_2Cl$
HFC-263: trifluoropropane, or $C_3H_5F_3$
Trifluoropropyne: $CF_3—C≡CH$ The composition according to the invention may optionally be a mixture of one or more azeotropes and/or heteroazeotropes of ternary, quaternary, penternary systems, systems with six compounds, systems with seven compounds, systems with eight or more compounds.

The compound(s) containing 1 and/or 2 carbon atoms may be chosen especially from chloromethane, chloropentafluoroethane, 1-chloro-1,2,2,2-tetrafluoroethane, 1-chloro-1,1,2,2-tetrafluoroethane, pentafluoroethane, 1-chloro-1,2,2-trifluoroethane, 1-chloro-2,2,2-trifluoroethane, 1,1,2,2-tetrafluoroethane, 1,1,1,2-tetrafluoroethane, 1-chloro-1,2-difluoroethane, 1-chloro-1,1-difluoroethane, 1,1,2-trifluoroethane, 1,1,1-trifluoroethane, 1,1,2-trifluoroethane, 1,1-difluoroethane, 1,2-difluoroethylene and fluoroethylene.

The compound(s) containing 3 carbon atoms may be chosen especially from 1,2-dichloro-1,1,2,3,3,3-hexafluoropropane, 1,3-dichloro-1,1,2,2,3,3-hexafluoropropane, 1,1-dichloro-1,2,2,3,3,3-hexafluoropropane, 2,2-dichloro-1,1,1,3,3,3-hexafluoropropane, 1-chloro-1,1,2,2,3,3,3-heptafluoropropane, 2-chloro-1,1,1,2,3,3,3-heptafluoropropane, octafluoropropane, dichloropentafluoropropane, 2,2-dichloro-1,1,1,3,3-pentafluoropropane, 2,3-dichloro-1,1,1,2,3-pentafluoropropane, 1,2-dichloro-1,1,2,3,3-pentafluoropropane, 3,3-dichloro-1,1,1,2,2-pentafluoropropane, 1,3-dichloro-1,1,2,2,3-pentafluoropropane, 1,1-dichloro-1,2,2,3,3-pentafluoropropane, 1,2-dichloro-1,1,3,3,3-pentafluoropropane, 1,3-dichloro-1,1,2,3,3-pentafluoropropane, 1,1-dichloro-1,2,3,3,3-pentafluoropropane, chlorohexafluoropropane, 2-chloro-1,1,1,2,3,3-hexafluoropropane, 3-chloro-1,1,1,2,2,3-hexafluoropropane, 1-chloro-1,1,2,2,3,3-hexafluoropropane, 2-chloro-1,1,1,3,3,3-hexafluoropropane, 1-chloro-1,1,2,3,3,3-hexafluoropropane, 1,1,2,2,3,3,3-heptafluoropropane, 1,1,1,2,3,3,3-Heptafluoropropane, dichlorotetrafluoropropane, 2,2-dichloro-1,1,3,3-tetrafluoropropane, 2,2-dichloro-1,1,1,3-tetrafluoropropane, 1,2-dichloro-1,2,3,3-tetrafluoropropane, 2,3-dichloro-1,1,1,2-tetrafluoropropane, 1,2-dichloro-1,1,2,3-tetrafluoropropane, 1,3-dichloro-1,2,2,3-tetrafluoropropane, 1,1-dichloro-2,2,3,3-tetrafluoropropane, 1,3-dichloro-1,1,2,2-tetrafluoropropane, 1,1-dichloro-1,2,2,3-tetrafluoropropane, 2,3-dichloro-1,1,1,3-tetrafluoropropane, 1,3-dichloro-1,1,3,3-tetrafluoropropane, 1,3-dichloro-1,1,3,3-tetrafluoropropane, 1,1-dichloro-1,3,3,3-tetrafluoropropane, 1,1-dichloro-2,3,3,3-tetrafluoropropane, 1,3-dichloro-1,1,2,3-tetrafluoropropane, 1,1-dichloro-1,2,3,3-tetrafluoropropane, chloropentafluoropropane, 1-chloro-1,2,2,3,3-pentafluoropropane, 3-chloro-1,1,1,2,3-pentafluoropropane, 1-chloro-1,1,2,2,3-pentafluoropropane, 2-chloro-1,1,1,3,3-pentafluoropropane, 1-chloro-1,1,3,3,3-pentafluoropropane, 1-chloro-1,1,2,3,3-pentafluoropropane, 3-chloro-1,1,1,2,2-pentafluoropropane, 2-chloro-1,1,2,3,3-pentafluoropropane, 2-chloro-1,1,1,2,3-pentafluoropropane, 1,1,1,2,2,3-hexafluoropropane, 1,1,1,2,3,3-hexafluoropropane, 1,1,1,3,3,3-hexafluoropropane, 1,1,2,2,3,3-hexafluoropropane, dichlorotrifluoropropane, 1,1-dichloro-3,3,3-trifluoropropane, 1,3-dichloro-1,1,3-trifluoropropane, 1,1-dichloro-1,3,3-trifluoropropane, 1,3-dichloro-1,2,3-trifluoropropane, 1,1-dichloro-2,3,3-trifluoropropane, 1,3-dichloro-1,1,2-trifluoropropane, 1,1-dichloro-1,2,3-trifluoropropane, 1,2-dichloro-1,3,3-trifluoropropane, 2,3-dichloro-1,1,1-trifluoropropane, 1,2-dichloro-1,1,3-trifluoropropane, 1,3-dichloro-1,2,2-trifluoropropane, 1,1-dichloro-2,2,3-trifluoropropane, 1,1-dichloro-1,2,2-trifluoropropane, 2,3-dichloro-1,1,2-trifluoropropane, 1,2-dichloro-1,2,3-trifluoropropane, 1,2-dichloro-1,1,2-trifluoropropane, 2,2-dichloro-1,1,3-trifluoropropane, 2,2-dichloro-3,3,3-trifluoropropane, chlorotetrafluoropropane, 2-chloro-1,2,3,3-tetrafluoropropane, 2-chloro-1,1,1,2-tetrafluoropropane, 3-chloro-1,1,2,2-tetrafluoropropane, 1-chloro-1,2,2,3-tetrafluoropropane, 1-chloro-1,1,2,2-tetrafluoropropane, 2-chloro-1,1,3,3-tetrafluoropropane, 2-chloro-1,1,1,3-tetrafluoropropane, 3-chloro-1,1,2,3-tetrafluoropropane, 3-chloro-1,1,1,2-tetrafluoropropane, 1-chloro-1,1,2,3-tetrafluoropropane, 3-chloro-1,1,1,3-tetrafluoropropane, 1-chloro-1,1,3,3-tetrafluoropropane, pentafluoropropane, 1,1,2,2,3-pentafluoropropane, 1,1,2,3,3-pentafluoropropane, 1,1,1,2,3-pentafluoropropane, 1,1,1,3,3-pentafluoropropane, chlorotrifluoropropane, 2-chloro-1,2,3-trifluoropropane, 2-chloro-1,1,2-trifluoropropane, 1-chloro-2,2,3-trifluoropropane, 1-chloro-1,2,2-trifluoropropane, 3-chloro-1,1,2-trifluoropropane, 1-chloro-1,2,3-trifluoropropane, 1-chloro-1,1,2-trifluoropropane, 3-chloro-1,3,3-trifluoropropane, 3-chloro-1,1,1-trifluoropropane, 1-chloro-1,1,3-trifluoropropane, 2-chloro-1,1,3-trifluoropropane, 2-chloro-1,1,1-trifluoropropane, 1,1,2,2-tetrafluoropropane, 1,1,1,3-tetrafluoropropane, 1,1,2,3-tetrafluoropropane, 1,1,1,2-tetrafluoropropane, 1,2,2,3-tetrafluoropropane, 1,1,3,3-tetrafluoropropane, chlorodifluoropropane, 1-chloro-2,2-difluoropropane, 3-chloro-1,1-difluoropropane, 1-chloro-1,3-difluoropropane, 1-chloro-1,1-difluoropropane, 1-chloro-2,3-difluoropropane, 1-chloro-1,2-difluoropropane, 2-chloro-1,3-difluoropropane, 2-chloro-1,1-difluoropropane, 2-chloro-1,2-difluoropropane, trifluoropropane, 1,1,1-trifluoropropane, 1,1,3-trifluoropropane, 1,2,3-trifluoropropane, 1,1,2-trifluoropropane, 1,2,2-trifluoropropane, dichlorotetrafluoropropene, 1,2-dichloro-1,3,3,3- tetrafluoropropene, 1,1-dichloro-2,3,3,3-tetrafluoropropene, 1,3-dichloro-1,2,3,3-tetrafluoropropene, 2,3-dichloro-1,1,3,3-tetrafluoropropene, 3,3-dichloro-1,1,2,3-tetrafluoropropene, chloropentafluoropropene, 1-chloropentafluoropropene, 2-chloropentafluoropropene, 3-chloropentafluoropropene, hexafluoropropene, dichlorotrifluoropropene, 1,1-dichloro-3,3,3-trifluoropropene, 1,2-dichloro-3,3,3-trifluoropropene, 2,3-dichloro-1,3,3-trifluoropropene, 1,3-dichloro-2,3,3-trifluoropropene, 1,2-dichloro-1,3,3-trifluoropropene, 2,3-dichloro-1,1,3-trifluoropropene, 1,1-dichloro-2,3,3-trifluoropropene, 1,3-dichloro-1,2,3-trifluoropropene, 3,3-dichloro-1,1,2-trifluoropropene, 3,3-dichloro-1,2,3-trifluoropropene, 1,3-dichloro-1,3,3-trifluoropropene, 3,3-dichloro-1,1,3-trifluoropropene, 1-chloro-2,3,3,3-tetrafluoropropene, 1-chloro-1,3,3,3-tetrafluoropropene, 2-chloro-1,3,3,3-tetrafluoropropene, 3-chloro-1,2,3,3-tetrafluoropropene, 3-chloro-1,1,3,3-tetrafluoropropene, 2-chloro-1,1,3,3-tetrafluoropropene, 1-chloro-1,2,3,3-tetrafluoropropene, 3-chloro-1,1,2,3-tetrafluoropropene, 1,2,3,3,3-pentafluoropropene, 1,1,3,3,3-pentafluoropropene, 1,1,2,3,3-pentafluoropropene, dichlorodifluoropropene, 2,3-dichloro-3,3-difluoropropene, 1,2-dichloro-1,3-difluoropropene, 2,3-dichloro-1,1-difluoropropene, 1,2-dichloro-3,3-difluoropropene, 2,3-dichloro-1,3-difluoropropene, 1,1-dichloro-2,3-difluoropropene, 1,3-dichloro-1,2-difluoropropene, 1,3-dichloro-2,3-difluoropropene, 3,3-dichloro-1,2-difluoropropene, 3,3-dichloro-2,3-difluoropropene, 1,1-dichloro-3,3-difluoropropene, 1,3-dichloro-1,3-difluoropropene, 3,3-dichloro-1,1-difluoropropene, 1,3-dichloro-3,3-difluoropropene, 3,3-dichloro-1,3-difluoropropene, chlorotrifluoropropene, 2-chloro-1,1,3-trifluoropropene, 2-chloro-1,3,3-trifluoropropene, 1-chloro-1,2,3-trifluoropropene, 3-chloro-1,1,2-trifluoropropene, 1-chloro-2,3,3-trifluoropropene, 3-chloro-1,2,3-trifluoropropene, 3-chloro-2,3,3-trifluoropropene, 1-chloro-1,3,3-trifluoropropene, 3-chloro-1,1,3-trifluoropropene, 3-chloro-1,3,3-trifluoropropene, 1,1,2,3-tetrafluoropropene, 2,3,3,3-tetrafluoropropene, 1,2,3,3-tetrafluoropropene, 1,1,3,3-tetrafluoropropene, chlorodifluoropropene, 3-chloro-3,3-difluoropropene, 3-chloro-1,3-difluoropropene, 2-chloro-1,1-difluoropropene, 2-chloro-1,3-difluoropropene, 2-chloro-3,3-difluoropropene, 1-chloro-1,2-difluoropropene, 1-chloro-2,3-difluoropropene, 3-chloro-1,2-difluoropropene, 3-chloro-2,3-difluoropropene, 1-chloro-1,3-difluoropropene, 3-chloro-1,1-difluoropropene, 1-chloro-3,3-difluoropropene, trifluoropropene, 1,1,2-trifluoropropene, 1,2,3-trifluoropropene, 2,3,3-trifluoropropene, 1,1,3-trifluoropropene, 1,3,3-trifluoropropene, chlorofluoropropene, 1-chloro-3-fluoropropene, 1-chloro-1-fluoropropene, 1-chloro-2-fluoropropene, 2-chloro-1-fluoropropene, 2-chloro-3-fluoropropene, 3-chloro-2-fluoropropene, 3-chloro-1-fluoropropene, 3-chloro-3-fluoropropene, difluoropropene, 1,2-difluoropropene, 2,3-difluoropropene, 1,1-difluoropropene, 1,3-difluoropropene, 3,3-difluoropropene, 1,1,1,2,2-pentafluoropropane, E-1,3,3,3-tetrafluoropropene, Z-1,3,3,3-tetrafluoropropene, 3,3,3-trifluoropropene, 3,3,3-trifluoro-2-chloropropene, E-3,3,3-trifluoro-1-chloropropene, Z-3,3,3-trifluoro-1-chloropropene and trifluoropropyne. Preferably, the ternary compositions consisting essentially of HF—HFCO-1233zdE-HFC-245fa are excluded from the present invention.

A subject of the present invention is also an azeotropic or quasi-azeotropic composition comprising hydrogen fluoride, E-3,3,3-trifluoro-1-chloropropene, and optionally one or more compounds chosen from 1,1,1,2,2-pentafluoropropane, 2,3,3,3-tetrafluoropropene, 3,3,3-trifluoropropene, 3,3,3-trifluoro-2-chloropropene, 1,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

A subject of the present invention is also an azeotropic or quasi-azeotropic composition comprising hydrogen fluoride, E-3,3,3-trifluoro-1-chloropropene and optionally at least one or more organic compounds chosen from 1,1,1,2,2-pentafluoropropane, 2,3,3,3-tetrafluoropropene, E-1,3,3,3-tetrafluoropropene, Z-1,3,3,3-tetrafluoropropene, 3,3,3-trifluoropropene, 3,3,3-trifluoro-2-chloropropene.

According to one embodiment, the composition according to the invention comprises hydrogen fluoride, E-3,3,3-trifluoro-1-chloropropene, 1,1,1,2,2-pentafluoropropane and optionally one or more compounds chosen from 2,3,3,3-tetrafluoropropene, 3,3,3-trifluoropropene, 3,3,3-trifluoro-2-chloropropene, 1,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, E-3,3,3-trifluoro-1-chloropropene, 2,3,3,3-tetrafluoropropene and optionally one or more compounds chosen from 3,3,3-trifluoropropene, 3,3,3-trifluoro-2-chloropropene, 1,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to one embodiment, the composition according to the invention comprises hydrogen fluoride, E-3,3,3-trifluoro-1-chloropropene, 3,3,3-trifluoropropene and optionally one or more compounds chosen from 3,3,3-trifluoro-2-chloropropene, 1,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, E-3,3,3-trifluoro-1-chloropropene, 3,3,3-trifluoro-2-chloropropene and optionally one or more compounds chosen from 1,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to one embodiment, the composition according to the invention comprises hydrogen fluoride, E-3,3,3-trifluoro-1-chloropropene, 1,3,3,3-tetrafluoropropene and optionally one or more compounds chosen from trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, E-3,3,3-trifluoro-1-chloropropene, trifluoropropyne and optionally one or more compounds chosen from 1,1,1,3,3-pentafluoropropane, 1,1,1,3,3-pentafluoropropene, 1,1,1,2,3-pentafluoropropene and 2-chloro,1,1,1,2-tetrafluoropropane.

According to one embodiment, the composition according to the invention comprises hydrogen fluoride, E-3,3,3-trifluoro-1-chloropropene, 1,1,1,3,3-pentafluoropropane and optionally one or more compounds chosen from 1,1,1,3,3-pentafluoropropene, 1,1,1,2,3-pentafluoropropene and 2-chloro,1,1,1,2-tetrafluoropropane.

According to another embodiment, the composition according to the invention comprises hydrogen fluoride, E-3,3,3-trifluoro-1-chloropropene, 1,1,1,3,3-pentafluoropropene and optionally one or more compounds chosen from 1,1,1,2,3-pentafluoropropene and 2-chloro,1,1,1,2-tetrafluoropropane.

According to one embodiment, the composition according to the invention comprises hydrogen fluoride, E-3,3,3-trifluoro-1-chloropropene, 1,1,1,3,3-pentafluoropropene and optionally 2-chloro-1,1,1,2-tetrafluoropropane.

According to another embodiment, the composition according to the invention comprises hydrogen fluoride, E-3,3,3-trifluoro-1-chloropropene and 2-chloro-1,1,1,2-tetrafluoropropane.

According to one embodiment, the composition according to the invention comprises hydrogen fluoride, E-3,3,3-trifluoro-1-chloropropene, 1,1,1,2,2-pentafluoropropane and optionally one or more compounds chosen from 2,3,3,3-tetrafluoropropene, E-1,3,3,3-tetrafluoropropene, Z-1,3,3,3-tetrafluoropropene, 3,3,3-trifluoropropene, 3,3,3-trifluoro-2-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to one embodiment, the composition according to the invention comprises hydrogen fluoride, E-3,3,3-trifluoro-1-chloropropene, 2,3,3,3-tetrafluoropropene and optionally one or more compounds chosen from E-1,3,3,3-tetrafluoropropene, Z-1,3,3,3-tetrafluoropropene, 3,3,3-trifluoropropene, 3,3,3-trifluoro-2-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane. According to one embodiment, the composition according to the invention comprises hydrogen fluoride, E-3,3,3-trifluoro-1-chloropropene, E-1,3,3,3-tetrafluoropropene and optionally one or more compounds chosen from Z-1,3,3,3-tetrafluoropropene, 3,3,3-trifluoropropene, 3,3,3-trifluoro-2-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, E-3,3,3-trifluoro-1-chloropropene, Z-1,3,3,3-tetrafluoropropene and optionally one or more compounds chosen from 3,3,3-trifluoropropene, 3,3,3-trifluoro-2-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, E-3,3,3-trifluoro-1-chloropropene, 3,3,3-trifluoropropene and optionally one or more compounds chosen from 3,3,3-trifluoro-2-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrachloropropane.

According to one embodiment according to the invention, the composition comprises hydrogen fluoride, E-3,3,3-trifluoro-1-chloropropene, 3,3,3-trifluoro-2-chloropropene and optionally one or more compounds chosen from trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

Irrespective of the embodiment, the composition preferably comprises from 1% to 85% and advantageously from 5% to 80% by weight of hydrogen fluoride and from 99% to 15% and advantageously from 20% to 95% by weight of the sum of the organic compounds; more particularly, the composition comprises from 1% to 85% by weight of hydrogen fluoride and from 99% to 15% by weight of the sum of the organic compounds (HFO-1233zdE and the (hydro)halocarbon compounds).

Irrespective of the embodiment, the boiling point of the composition according to the invention is between −20° C. and 80° C. and at a pressure between 0.1 and 44 bar absolute, preferentially between 0° C. and 40° C. and preferentially at a pressure of between 0.7 and 18 bar absolute, advantageously between 0.9 and 12.5 bar absolute.

The Applicant has discovered that the compositions according to the invention have advantageous properties in particular for the recycling of HF in the reaction step. Thus, the condensed phase of these compositions, optionally when they are subjected to a distillation step and/or a liquid/liquid separation step, such as by decantation, form two immiscible liquid phases.

By way of example, for the ternary compounds containing hydrogen fluoride, E-3,3,3-trifluoro-1-chloropropene and a compound chosen from 1,1,1,2,2-pentafluoropropane, 2,3,3,3-tetrafluoropropene, 3,3,3-trifluoropropene, 1,3,3,3-tetrafluoropropene, 3,3,3-trifluoro-2-chloropropene, the appearance of a heteroazeotrope characterized by two liquid phases, one rich in HF and the other depleted in HF, depends on the amount of HF in the composition. These decantation ranges as a function of the HF content in the compositions were characterized for at least isotherms at 0° C., 25° C. and 40° C.

Similarly, the decantation ranges for the ternary compounds containing hydrogen fluoride, E-3,3,3-trifluoro-1-chloropropene and a compound chosen from trifluoropropyne, 1,1,1,3,3-pentafluoropropane, 1,1,1,3,3-pentafluoropropene, Z-1,1,1,2,3-pentafluoropropene and 2-chloro-1,1,1,2-tetrafluoropropane are characterized by a phase depleted in HF and a phase enriched in HF for at least isotherms at 0° C., 25° C. and 40° C.

The Applicant has observed the same phenomenon for compositions of hydrogen fluoride, E-3,3,3-trifluoro-1-chloropropene comprising several compounds chosen from 1,1,1,2,2-pentafluoropropane, 2,3,3,3-tetrafluoropropene, 3,3,3-trifluoropropene, 1,3,3,3-tetrafluoropropene, 3,3,3-trifluoro-2-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

An azeotropic or quasi-azeotropic composition that is preferred according to the invention comprises from 5% to 70% by weight of hydrogen fluoride and from 95% to 30% by weight of HCFO-1233zdE, the boiling point of this preferred composition is between 0 and 40° C. at a pressure of between 0.9 and 4 bar absolute.

An azeotropic or quasi-azeotropic composition that is preferred according to the invention preferably comprises from 10% to 65% by weight of hydrogen fluoride and from 90% to 35% by weight of HCFO-1233zdE, the boiling point of this preferred composition is between 0 and 40° C. at a pressure of between 0.9 and 4 bar absolute.

An azeotropic or quasi-azeotropic composition that is preferred according to the invention comprises from 1% to 85% by weight of hydrogen fluoride and from 99% to 15% by weight of the sum of HCFO-1233zdE and of HFC-245cb, the boiling point of this preferred composition is between 0 and 40° C. at a pressure of between 0.9 and 10.5 bar absolute.

An azeotropic or quasi-azeotropic composition that is preferred according to the invention preferably comprises from 10% to 80% by weight of hydrogen fluoride and from 90% to 20% by weight of the sum of HCFO-1233zdE and of HFO-245b, the boiling point of this preferred composition is between 0 and 40° C. at a pressure of between 0.9 and 10.5 bar absolute.

An azeotropic or quasi-azeotropic composition that is preferred according to the invention comprises from 1% to 80% by weight of hydrogen fluoride and from 99% to 20% by weight of the sum of HCFO-1233zdE and of HFO-1243zf, the boiling point of this preferred composition is between 0 and 40° C. at a pressure of between 0.9 and 10.5 bar absolute.

An azeotropic or quasi-azeotropic composition that is preferred according to the invention preferably comprises from 5% to 75% by weight of hydrogen fluoride and from 95% to 25% by weight of the sum of HCFO-1233zdE and of HFO-1243zf, the boiling point of this preferred composition is between 0 and 40° C. at a pressure of between 0.9 and 10.5 bar absolute.

An azeotropic or quasi-azeotropic composition that is preferred according to the invention comprises from 1% to 85% by weight of hydrogen fluoride and from 99% to 15% by weight of the sum of HCFO-1233zdE, of HFC-245cb and of HFO-1243zf, the boiling point of this preferred composition is between 0 and 40° C. at a pressure of between 0.9 and 10.5 bar absolute.

An azeotropic or quasi-azeotropic composition that is preferred according to the invention preferably comprises from 5% to 80% by weight of hydrogen fluoride and from 95% to 20% by weight of the sum of HCFO-1233zdE, of HFC-245cb and of HFO-1243zf, the boiling point of this preferred composition is between 0 and 40° C. at a pressure of between 0.9 and 10.5 bar absolute.

An azeotropic or quasi-azeotropic composition that is preferred according to the invention comprises from 1% to 80% by weight of hydrogen fluoride and from 99% to 20% by weight of the sum of HCFO-1233zd, of HCFC-244bb, of HFC-245a, of trifluoropropyne, of HFO-1225yeZ and of HFO-1225zc, the boiling point of this preferred composition is between 0 and 40° C. at a pressure of between 0.7 and 18 bar absolute.

An azeotropic or quasi-azeotropic composition that is preferred according to the invention preferably comprises from 5% to 75% by weight of hydrogen fluoride and from 95% to 25% by weight of the sum of HCFO-1233zd, of HCFC-244bb, of HFC-245a, of trifluoropropyne, of HFO-1225yeZ and of HFO-1225zc, the boiling point of this preferred composition is between 0 and 40° C. at a pressure of between 0.7 and 18 bar absolute.

The pressure characteristics of the mixtures in Examples 1, 4, 7, 10, 13, 16, 19 and 22 have been calculated for an isotherm at 25° C.

Examples 2, 5, 8, 11, 14, 17, 20 and 23 represent the boiling points and pressure ranges of the mixtures and Examples 3, 6, 9, 12, 15, 18, 21 and 23 represent the decantation ranges of the mixtures of Examples 1, 4, 7, 10, 13, 16, 19 and 22 as a function of the mass percentage of HF characterized for isotherms at 0° C., 25° C. and 40° C. The decantation ranges of Examples 3, 6, 9, 12, 15, 18, 21 and 23 are calculated for mixtures of organic compounds having equal-mass contents. By way of example, for a ternary mixture, a mixture containing 50% by weight of each of the two organic compounds is considered; for a penternary mixture, a mixture containing 25% by weight of each of the four organic compounds is considered, the mass fraction of HF ranging from 0 to 1. These calculations are performed at the liquid-vapor equilibrium, under azeotropic conditions.

Example 1: Binary Mixture

HF-HCFO-1233zdE

| | Binary HF - F1233zdE | | |
|---|---|---|---|
| HF massfrac | Isotherm 0° C. Pressure bar | Isotherm 25° C. Pressure bar | Isotherm 40° C. Pressure bar |
| 0 | 0.5 | 1.3 | 2.2 |
| 0.05 | 0.9 | 2.4 | 4.0 |
| 0.1 | 0.9 | 2.4 | 4.0 |
| 0.15 | 0.9 | 2.4 | 4.0 |
| 0.2 | 0.9 | 2.4 | 4.0 |
| 0.25 | 0.9 | 2.4 | 4.0 |
| 0.3 | 0.9 | 2.4 | 4.0 |
| 0.35 | 0.9 | 2.4 | 4.0 |
| 0.4 | 0.9 | 2.4 | 4.0 |
| 0.45 | 0.9 | 2.4 | 4.0 |
| 0.5 | 0.9 | 2.4 | 4.0 |
| 0.55 | 0.9 | 2.4 | 4.0 |
| 0.6 | 0.9 | 2.4 | 4.0 |
| 0.65 | 0.9 | 2.4 | 4.0 |
| 0.7 | 0.9 | 2.4 | 4.0 |
| 0.75 | 0.9 | 2.4 | 3.9 |
| 0.8 | 0.9 | 2.3 | 3.8 |
| 0.85 | 0.9 | 2.2 | 3.5 |
| 0.9 | 0.8 | 1.9 | 3.2 |
| 0.95 | 0.6 | 1.6 | 2.7 |
| 1 | 0.5 | 1.2 | 1.9 |

Example 2: Temperature and Pressure Range of the Binary Mixture

| | Boiling point range | |
|---|---|---|
| Binary | Temperature ° C. | Pressure bar abs |
| HF-HCFO-1233zdE-HFC-245cb | 0 to 40 | ~0.9 to ~4.0 |

Example 3: Decantation Range of the Binary Mixture

| | Decantation ranges Mass percentage of HF Temperature | | |
|---|---|---|---|
| Binary system | 0° C. | 25° C. | 40° C. |
| HF-HCFO-1233zdE | 5-80% | 5-75% | 5-70% |

Example 4: Ternary Mixtures, Isotherm at 25° C.

| HF-HCFO-1233zdE-HFC-245cb | | | | | |
|---|---|---|---|---|---|
| Organics 0.95 F1233zdE + 0.05 F245cb | | Organics 0.5 F1233zdE + 0.05 F245cb | | Organics 0.05 F1233zdE + 0.95 F245cb | |
| MASSFRAC HF | TOTAL PRESSURE bar | MASSFRAC HF | TOTAL PRESSURE bar | MASSFRAC HF | TOTAL PRESSURE bar |
| 0 | 1.5 | 0 | 3.0 | 0 | 4.5 |
| 0.05 | 2.6 | 0.05 | 4.2 | 0.05 | 5.7 |
| 0.1 | 2.6 | 0.1 | 4.2 | 0.1 | 5.7 |
| 0.15 | 2.6 | 0.15 | 4.2 | 0.15 | 5.7 |
| 0.2 | 2.6 | 0.2 | 4.2 | 0.2 | 5.7 |
| 0.25 | 2.6 | 0.25 | 4.2 | 0.25 | 5.7 |
| 0.3 | 2.6 | 0.3 | 4.2 | 0.3 | 5.7 |
| 0.35 | 2.6 | 0.35 | 4.2 | 0.35 | 5.7 |
| 0.4 | 2.6 | 0.4 | 4.2 | 0.4 | 5.7 |
| 0.45 | 2.6 | 0.45 | 4.2 | 0.45 | 5.7 |
| 0.5 | 2.6 | 0.5 | 4.2 | 0.5 | 5.7 |
| 0.55 | 2.6 | 0.55 | 4.2 | 0.55 | 5.7 |
| 0.6 | 2.6 | 0.6 | 4.3 | 0.6 | 5.7 |
| 0.65 | 2.6 | 0.65 | 4.3 | 0.65 | 5.7 |
| 0.7 | 2.6 | 0.7 | 4.3 | 0.7 | 5.7 |
| 0.75 | 2.6 | 0.75 | 4.4 | 0.75 | 5.7 |
| 0.8 | 2.5 | 0.8 | 4.4 | 0.8 | 5.7 |
| 0.85 | 2.4 | 0.85 | 4.1 | 0.85 | 5.7 |
| 0.9 | 2.1 | 0.9 | 3.5 | 0.9 | 4.9 |
| 0.95 | 1.7 | 0.95 | 2.6 | 0.95 | 3.5 |
| 1 | 1.2 | 1 | 1.2 | 1 | 1.2 |

| HF-HCFO-1233zdE-HFC-245cb | | | | | |
|---|---|---|---|---|---|
| Organics 0.95 F1233zdE + 0.05 F1233xf | | Organics 0.5 F1233zdE + 0.5 1233xf | | Organics 0.05 F1233zdE + 0.95 F1233xf | |
| MASSFRAC HF | TOTAL PRESSURE bar | MASSFRAC HF | TOTAL PRESSURE bar | MASSFRAC HF | TOTAL PRESSURE bar |
| 0 | 1.3 | 0 | 1.4 | 0 | 1.5 |
| 0.05 | 2.4 | 0.05 | 2.5 | 0.05 | 2.6 |
| 0.1 | 2.4 | 0.1 | 2.5 | 0.1 | 2.6 |
| 0.15 | 2.4 | 0.15 | 2.5 | 0.15 | 2.6 |
| 0.2 | 2.4 | 0.2 | 2.5 | 0.2 | 2.6 |
| 0.25 | 2.4 | 0.25 | 2.5 | 0.25 | 2.6 |
| 0.3 | 2.4 | 0.3 | 2.5 | 0.3 | 2.6 |
| 0.35 | 2.4 | 0.35 | 2.5 | 0.35 | 2.6 |
| 0.4 | 2.4 | 0.4 | 2.5 | 0.4 | 2.6 |
| 0.45 | 2.4 | 0.45 | 2.5 | 0.45 | 2.6 |
| 0.5 | 2.4 | 0.5 | 2.5 | 0.5 | 2.6 |
| 0.55 | 2.4 | 0.55 | 2.5 | 0.55 | 2.6 |
| 0.6 | 2.4 | 0.6 | 2.5 | 0.6 | 2.6 |
| 0.65 | 2.4 | 0.65 | 2.5 | 0.65 | 2.6 |
| 0.7 | 2.4 | 0.7 | 2.5 | 0.7 | 2.6 |
| 0.75 | 2.4 | 0.75 | 2.5 | 0.75 | 2.6 |
| 0.8 | 2.3 | 0.8 | 2.4 | 0.8 | 2.5 |
| 0.85 | 2.2 | 0.85 | 2.3 | 0.85 | 2.3 |
| 0.9 | 1.9 | 0.9 | 2.0 | 0.9 | 2.1 |
| 0.95 | 1.6 | 0.95 | 1.7 | 0.95 | 1.7 |
| 1 | 1.2 | 1 | 1.2 | 1 | 1.2 |

| HF-HFO-1234zeE-HCFO-1233zdE | | | | | |
|---|---|---|---|---|---|
| Organics 0.95 F1233zdE + 0.05 F1234zeE | | Organics 0.5 F1233zdE + 0.5 F1234zeE | | Organics 0.05 F1233zdE + 0.95 F1234zeE | |
| MASSFRAC HF | TOTAL PRESSURE bar | MASSFRAC HF | TOTAL PRESSURE bar | MASSFRAC HF | TOTAL PRESSURE bar |
| 0 | 1.5 | 0 | 3.2 | 0 | 4.7 |
| 0.05 | 2.6 | 0.05 | 4.2 | 0.05 | 5.7 |
| 0.1 | 2.6 | 0.1 | 4.2 | 0.1 | 5.7 |
| 0.15 | 2.6 | 0.15 | 4.2 | 0.15 | 5.7 |
| 0.2 | 2.6 | 0.2 | 4.2 | 0.2 | 5.7 |

-continued

| | | | | | |
|---|---|---|---|---|---|
| 0.25 | 2.6 | 0.25 | 4.2 | 0.25 | 5.7 |
| 0.3 | 2.6 | 0.3 | 4.2 | 0.3 | 5.7 |
| 0.35 | 2.6 | 0.35 | 4.2 | 0.35 | 5.7 |
| 0.4 | 2.6 | 0.4 | 4.2 | 0.4 | 5.7 |
| 0.45 | 2.6 | 0.45 | 4.2 | 0.45 | 5.7 |
| 0.5 | 2.6 | 0.5 | 4.1 | 0.5 | 5.6 |
| 0.55 | 2.6 | 0.55 | 4.1 | 0.55 | 5.6 |
| 0.6 | 2.6 | 0.6 | 4.1 | 0.6 | 5.5 |
| 0.65 | 2.6 | 0.65 | 4.1 | 0.65 | 5.4 |
| 0.7 | 2.6 | 0.7 | 4.0 | 0.7 | 5.2 |
| 0.75 | 2.6 | 0.75 | 3.8 | 0.75 | 5.0 |
| 0.8 | 2.4 | 0.8 | 3.6 | 0.8 | 4.7 |
| 0.85 | 2.3 | 0.85 | 3.2 | 0.85 | 4.2 |
| 0.9 | 2.0 | 0.9 | 2.8 | 0.9 | 3.5 |
| 0.95 | 1.7 | 0.95 | 2.1 | 0.95 | 2.5 |
| 1 | 1.2 | 1 | 1.2 | 1 | 1.2 |

HF-HFO-1234zeZ-HCFO-1233zdE

| Organics 0.95 F1233zdE + 0.05 F1234zeE | | Organics 0.5 F1233zdE + 0.5 F1234zeE | | Organics 0.05 F1233zdE + 0.95 F1234zeE | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 1.3 | 0 | 1.6 | 0 | 1.8 |
| 0.05 | 2.4 | 0.05 | 2.7 | 0.05 | 2.9 |
| 0.1 | 2.4 | 0.1 | 2.7 | 0.1 | 2.9 |
| 0.15 | 2.4 | 0.15 | 2.7 | 0.15 | 2.9 |
| 0.2 | 2.4 | 0.2 | 2.7 | 0.2 | 2.9 |
| 0.25 | 2.4 | 0.25 | 2.7 | 0.25 | 2.9 |
| 0.3 | 2.4 | 0.3 | 2.7 | 0.3 | 2.9 |
| 0.35 | 2.4 | 0.35 | 2.7 | 0.35 | 2.9 |
| 0.4 | 2.4 | 0.4 | 2.7 | 0.4 | 2.9 |
| 0.45 | 2.4 | 0.45 | 2.7 | 0.45 | 2.9 |
| 0.5 | 2.4 | 0.5 | 2.7 | 0.5 | 2.9 |
| 0.55 | 2.4 | 0.55 | 2.7 | 0.55 | 2.9 |
| 0.6 | 2.4 | 0.6 | 2.7 | 0.6 | 2.9 |
| 0.65 | 2.4 | 0.65 | 2.7 | 0.65 | 2.9 |
| 0.7 | 2.4 | 0.7 | 2.7 | 0.7 | 2.9 |
| 0.75 | 2.4 | 0.75 | 2.7 | 0.75 | 2.9 |
| 0.8 | 2.3 | 0.8 | 2.6 | 0.8 | 2.8 |
| 0.85 | 2.2 | 0.85 | 2.4 | 0.85 | 2.6 |
| 0.9 | 2.0 | 0.9 | 2.1 | 0.9 | 2.3 |
| 0.95 | 1.6 | 0.95 | 1.7 | 0.95 | 1.8 |
| 1 | 1.2 | 1 | 1.2 | 1 | 1.2 |

HF-HFO-1234yf-HCFO-1233zdE

| Organics 0.95 F1233zdE + 0.05 F1234yf | | Organics 0.5 F1233zdE + 0.5 F1234yf | | Organics 0.05 F1233zdE + 0.95 F1234yf | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 1.5 | 0 | 4.2 | 0 | 6.5 |
| 0.05 | 2.7 | 0.05 | 5.3 | 0.05 | 7.5 |
| 0.1 | 2.7 | 0.1 | 5.3 | 0.1 | 7.5 |
| 0.15 | 2.7 | 0.15 | 5.3 | 0.15 | 7.5 |
| 0.2 | 2.7 | 0.2 | 5.3 | 0.2 | 7.5 |
| 0.25 | 2.7 | 0.25 | 5.3 | 0.25 | 7.5 |
| 0.3 | 2.7 | 0.3 | 5.3 | 0.3 | 7.5 |
| 0.35 | 2.7 | 0.35 | 5.3 | 0.35 | 7.5 |
| 0.4 | 2.7 | 0.4 | 5.3 | 0.4 | 7.5 |
| 0.45 | 2.7 | 0.45 | 5.3 | 0.45 | 7.5 |
| 0.5 | 2.7 | 0.5 | 5.3 | 0.5 | 7.5 |
| 0.55 | 2.7 | 0.55 | 5.3 | 0.55 | 7.5 |
| 0.6 | 2.7 | 0.6 | 5.3 | 0.6 | 7.5 |
| 0.65 | 2.7 | 0.65 | 5.3 | 0.65 | 7.5 |
| 0.7 | 2.7 | 0.7 | 5.3 | 0.7 | 7.5 |
| 0.75 | 2.7 | 0.75 | 5.2 | 0.75 | 7.4 |
| 0.8 | 2.6 | 0.8 | 4.9 | 0.8 | 7.0 |
| 0.85 | 2.4 | 0.85 | 4.5 | 0.85 | 6.5 |
| 0.9 | 2.1 | 0.9 | 3.8 | 0.9 | 5.4 |
| 0.95 | 1.7 | 0.95 | 2.8 | 0.95 | 3.8 |
| 1 | 1.2 | 1 | 1.2 | 1 | 1.2 |

-continued

| HF-HCFO-1233zdE-HFO-1234zf | | | | | |
|---|---|---|---|---|---|
| Organics 0.95 F1234zf + 0.05 F1233zdE | | Organics 0.5 F1234zf + 0.5 F1233zdE | | Organics 0.05 F1234zf + 0.95 F1233zdE | |
| MASSFRAC HF | TOTAL PRESSURE bar6.6 | MASSFRAC HF | TOTAL PRESSURE bar | MASSFRAC HF | TOTAL PRESSURE bar |
| 0 | 5.7 | 0 | 3.9 | 0 | 1.6 |
| 0.05 | 6.6 | 0.05 | 5.0 | 0.05 | 2.7 |
| 0.1 | 6.6 | 0.1 | 4.9 | 0.1 | 2.7 |
| 0.15 | 6.6 | 0.15 | 4.9 | 0.15 | 2.7 |
| 0.2 | 6.6 | 0.2 | 4.9 | 0.2 | 2.7 |
| 0.25 | 6.6 | 0.25 | 4.9 | 0.25 | 2.7 |
| 0.3 | 6.6 | 0.3 | 4.9 | 0.3 | 2.7 |
| 0.35 | 6.6 | 0.35 | 4.9 | 0.35 | 2.7 |
| 0.4 | 6.6 | 0.4 | 4.9 | 0.4 | 2.7 |
| 0.45 | 6.6 | 0.45 | 4.9 | 0.45 | 2.7 |
| 0.5 | 6.6 | 0.5 | 4.9 | 0.5 | 2.7 |
| 0.55 | 6.6 | 0.55 | 4.9 | 0.55 | 2.7 |
| 0.6 | 6.6 | 0.6 | 4.9 | 0.6 | 2.7 |
| 0.65 | 6.5 | 0.65 | 4.8 | 0.65 | 2.7 |
| 0.7 | 6.4 | 0.7 | 4.8 | 0.7 | 2.7 |
| 0.75 | 6.3 | 0.75 | 4.8 | 0.75 | 2.7 |
| 0.8 | 6.0 | 0.8 | 4.4 | 0.8 | 2.5 |
| 0.85 | 5.5 | 0.85 | 4.0 | 0.85 | 2.4 |
| 0.9 | 4.6 | 0.9 | 3.4 | 0.9 | 2.1 |
| 0.95 | 3.3 | 0.95 | 2.5 | 0.95 | 1.7 |
| 1 | 1.2 | 1 | 1.2 | 1 | 1.2 |

Example 54: Temperature and Pressure Range of Ternary Mixtures

| | Boiling point range | |
|---|---|---|
| Ternary | Temperature ° C. | Pressure bar abs |
| HF-HCFO-1233zdE-HFC-245cb | 0 to 40 | ~1.0 to ~8.9 |
| HF-HCFO-1233xf-HCFO-1233zdE | 0 to 40 | ~0.9 to ~4.0 |
| HF-HFO-1234zeE-HCFO-1233zdE | 0 to 40 | ~1.0 to ~8.8 |
| HF-HFO-1234zeZ-HCFO-1233zdE | 0 to 40 | ~0.9 to ~4.8 |
| HF-HCFO-1233zdE-HFO-1243zf | 0 to 40 | ~1.1 to ~10.2 |
| HF-HFO-1234yf-HCFO-1233zdE | 0 to 40 | ~1.0 to ~11.4 |

Example 6: Decantation Range of Ternary Mixtures

| | Decantation ranges Mass percentage of HF | | |
|---|---|---|---|
| Ternary | Isotherm 0° C. | Isotherm 25° C. | Isotherm 40° C. |
| HF-HCFO-1233zdE-HFC-245cb | 5-80 | 5-75 | 5-75 |
| HF-HCFO-1233xf-HCFO-1233zdE | 5-80 | 5-75 | 5-65 |
| HF-HFO-1234zeE-HCFO-1233zdE | 5-70 | 5-65 | 10-50 |
| HF-HFO-1234zeZ-HCFO-1233zdE | 5-80 | 5-75 | 5-65 |
| HF-HCFO-1233zdE-HFO-1243zf | 5-75 | 5-65 | 15-45 |
| HF-HFO-1234yf-HCFO-1233zdE | 5-75 | 5-70 | 15-55 |

Example 7: Quaternary Mixtures, Isotherm at 25° C.

| HF - HCFO-1233xf - HCFO-1233zdE - HFC-245cb | | | | | | | |
|---|---|---|---|---|---|---|---|
| Organics 0.9 F1233xf + 0.05 F1233zdE + 0.05 F245cb | | Organics 0.4 F1233xf + 0.3 F1233zdE + 0.3 F245cb | | Organics 0.05 F1233xf + 0.9 F1233zdE + 0.05 F245cb | | Organics 0.05 F1233xf + 0.05 F1233zdE + 0.9 F245cb | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 2.4 | 0 | 1.5 | 0 | 4.3 |
| 0.05 | 2.8 | 0.05 | 3.6 | 0.05 | 2.6 | 0.05 | 5.5 |
| 0.1 | 2.8 | 0.1 | 3.6 | 0.1 | 2.6 | 0.1 | 5.5 |
| 0.15 | 2.8 | 0.15 | 3.6 | 0.15 | 2.6 | 0.15 | 5.5 |
| 0.2 | 2.8 | 0.2 | 3.6 | 0.2 | 2.6 | 0.2 | 5.5 |
| 0.25 | 2.8 | 0.25 | 3.6 | 0.25 | 2.6 | 0.25 | 5.5 |
| 0.3 | 2.8 | 0.3 | 3.6 | 0.3 | 2.6 | 0.3 | 5.5 |

-continued

| | | | | | | | |
|---|---|---|---|---|---|---|---|
| 0.35 | 2.8 | 0.35 | 3.6 | 0.35 | 2.6 | 0.35 | 5.5 |
| 0.4 | 2.8 | 0.4 | 3.6 | 0.4 | 2.6 | 0.4 | 5.5 |
| 0.45 | 2.8 | 0.45 | 3.6 | 0.45 | 2.6 | 0.45 | 5.5 |
| 0.5 | 2.8 | 0.5 | 3.6 | 0.5 | 2.6 | 0.5 | 5.5 |
| 0.55 | 2.8 | 0.55 | 3.6 | 0.55 | 2.6 | 0.55 | 5.5 |
| 0.6 | 2.8 | 0.6 | 3.7 | 0.6 | 2.6 | 0.6 | 5.5 |
| 0.65 | 2.8 | 0.65 | 3.7 | 0.65 | 2.6 | 0.65 | 5.5 |
| 0.7 | 2.8 | 0.7 | 3.7 | 0.7 | 2.6 | 0.7 | 5.6 |
| 0.75 | 2.8 | 0.75 | 3.7 | 0.75 | 2.6 | 0.75 | 5.6 |
| 0.8 | 2.7 | 0.8 | 3.7 | 0.8 | 2.5 | 0.8 | 5.6 |
| 0.85 | 2.5 | 0.85 | 3.4 | 0.85 | 2.4 | 0.85 | 5.5 |
| 0.9 | 2.2 | 0.9 | 2.9 | 0.9 | 2.1 | 0.9 | 4.8 |
| 0.95 | 1.8 | 0.95 | 2.2 | 0.95 | 1.7 | 0.95 | 3.4 |
| 1 | 1.2 | 1 | 1.2 | 1 | 1.2 | 1 | 1.2 |

HF - HCFO-1233xf - HCFO-1233zdE - HFO-1234zeE

| Organics 0.9 F1233xf + 0.05 F1233zdE + 0.05 F1234zeE | | Organics 0.05 F1233xf + 0.9 F1233zdE + 0.05 F1234zeE | | Organics 0.05 F1233xf + 0.05 F1233zdE + 0.9 F1234zeE | | Organics 0.4 F1233xf + 0.3 F1233zdE + 0.3 F1234zeE | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 1.5 | 0 | 4.6 | 0 | 2.5 |
| 0.05 | 2.8 | 0.05 | 2.6 | 0.05 | 5.5 | 0.05 | 3.5 |
| 0.1 | 2.8 | 0.1 | 2.6 | 0.1 | 5.5 | 0.1 | 3.5 |
| 0.15 | 2.8 | 0.15 | 2.6 | 0.15 | 5.5 | 0.15 | 3.5 |
| 0.2 | 2.8 | 0.2 | 2.6 | 0.2 | 5.5 | 0.2 | 3.5 |
| 0.25 | 2.8 | 0.25 | 2.6 | 0.25 | 5.5 | 0.25 | 3.5 |
| 0.3 | 2.8 | 0.3 | 2.6 | 0.3 | 5.5 | 0.3 | 3.5 |
| 0.35 | 2.8 | 0.35 | 2.6 | 0.35 | 5.5 | 0.35 | 3.5 |
| 0.4 | 2.8 | 0.4 | 2.6 | 0.4 | 5.5 | 0.4 | 3.5 |
| 0.45 | 2.8 | 0.45 | 2.6 | 0.45 | 5.5 | 0.45 | 3.5 |
| 0.5 | 2.8 | 0.5 | 2.6 | 0.5 | 5.5 | 0.5 | 3.5 |
| 0.55 | 2.8 | 0.55 | 2.6 | 0.55 | 5.4 | 0.55 | 3.5 |
| 0.6 | 2.8 | 0.6 | 2.6 | 0.6 | 5.4 | 0.6 | 3.5 |
| 0.65 | 2.8 | 0.65 | 2.6 | 0.65 | 5.3 | 0.65 | 3.5 |
| 0.7 | 2.8 | 0.7 | 2.6 | 0.7 | 5.1 | 0.7 | 3.5 |
| 0.75 | 2.8 | 0.75 | 2.6 | 0.75 | 4.3 | 0.75 | 3.3 |
| 0.8 | 2.6 | 0.8 | 2.5 | 0.8 | 4.6 | 0.8 | 3.2 |
| 0.85 | 2.4 | 0.85 | 2.3 | 0.85 | 4.1 | 0.85 | 2.9 |
| 0.9 | 2.2 | 0.9 | 2.0 | 0.9 | 3.4 | 0.9 | 2.5 |
| 0.95 | 1.7 | 0.95 | 1.7 | 0.95 | 2.5 | 0.95 | 1.9 |
| 1 | 1.2 | 1 | 1.2 | 1 | 1.2 | 1 | 1.2 |

HF - HCFO-1233xf - HCFO-1233zdE - HFO-1234zeZ

| Organics 0.9 F1233xf + 0.05 F1233zdE + 0.05 F1234zeZ | | Organics 0.05 F1233xf + 0.9 F1233zdE + 0.05 F1234zeZ | | Organics 0.05 F1233xf + 0.05 F1233zdE + 0.9 F1234zeZ | | Organics 0.4 F1233xf + 0.3 F1233zdE + 0.3 F1234zeZ | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.5 | 0 | 1.4 | 0 | 1.8 | 0 | 1.6 |
| 0.05 | 2.7 | 0.05 | 2.5 | 0.05 | 2.9 | 0.05 | 2.7 |
| 0.1 | 2.7 | 0.1 | 2.5 | 0.1 | 2.9 | 0.1 | 2.7 |
| 0.15 | 2.7 | 0.15 | 2.5 | 0.15 | 2.9 | 0.15 | 2.7 |
| 0.2 | 2.7 | 0.2 | 2.5 | 0.2 | 2.9 | 0.2 | 2.7 |
| 0.25 | 2.7 | 0.25 | 2.5 | 0.25 | 2.9 | 0.25 | 2.7 |
| 0.3 | 2.7 | 0.3 | 2.5 | 0.3 | 2.9 | 0.3 | 2.7 |
| 0.35 | 2.7 | 0.35 | 2.5 | 0.35 | 2.9 | 0.35 | 2.7 |
| 0.4 | 2.7 | 0.4 | 2.5 | 0.4 | 2.9 | 0.4 | 2.7 |
| 0.45 | 2.7 | 0.45 | 2.5 | 0.45 | 2.9 | 0.45 | 2.7 |
| 0.5 | 2.7 | 0.5 | 2.5 | 0.5 | 2.9 | 0.5 | 2.7 |
| 0.55 | 2.7 | 0.55 | 2.5 | 0.55 | 2.9 | 0.55 | 2.7 |
| 0.6 | 2.7 | 0.6 | 2.5 | 0.6 | 2.9 | 0.6 | 2.7 |
| 0.65 | 2.7 | 0.65 | 2.5 | 0.65 | 2.9 | 0.65 | 2.7 |
| 0.7 | 2.7 | 0.7 | 2.5 | 0.7 | 2.9 | 0.7 | 2.7 |
| 0.75 | 2.7 | 0.75 | 2.5 | 0.75 | 2.9 | 0.75 | 2.7 |
| 0.8 | 2.5 | 0.8 | 2.4 | 0.8 | 2.9 | 0.8 | 2.5 |
| 0.85 | 2.4 | 0.85 | 2.2 | 0.85 | 2.5 | 0.85 | 2.4 |

-continued

| | | | | | | | |
|---|---|---|---|---|---|---|---|
| 0.9 | 2.1 | 0.9 | 2.0 | 0.9 | 2.3 | 0.9 | 2.1 |
| 0.95 | 1.7 | 0.95 | 1.6 | 0.95 | 1.8 | 0.95 | 1.7 |
| 1 | 1.2 | 1 | 1.2 | 1 | 1.2 | 1 | 1.2 |

HF - HCFO-1233xf - HCFO-1233zdE - HFO-1234zf

| Organics 0.9 F1233xf + 0.05 F1233zdE + 0.05 F1243zf | | Organics 0.05 F1233xf + 0.9 F1233zdE + 0.05 F1243zf | | Organics 0.05 F1233xf + 0.05 F1233zdE + 0.9 F1243zf | | Organics 0.4 F1233xf + 0.3 F1233zdE + 0.3 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 1.6 | 0 | 5.5 | 0 | 3.0 |
| 0.05 | 2.9 | 0.05 | 2.7 | 0.05 | 6.4 | 0.05 | 4.1 |
| 0.1 | 2.9 | 0.1 | 2.7 | 0.1 | 6.5 | 0.1 | 4.1 |
| 0.15 | 2.9 | 0.15 | 2.7 | 0.15 | 6.5 | 0.15 | 4.1 |
| 0.2 | 2.9 | 0.2 | 2.7 | 0.2 | 6.5 | 0.2 | 4.1 |
| 0.25 | 2.9 | 0.25 | 2.7 | 0.25 | 6.5 | 0.25 | 4.1 |
| 0.3 | 2.9 | 0.3 | 2.7 | 0.3 | 6.5 | 0.3 | 4.1 |
| 0.35 | 2.9 | 0.35 | 2.7 | 0.35 | 6.5 | 0.35 | 4.1 |
| 0.4 | 2.9 | 0.4 | 2.7 | 0.4 | 6.5 | 0.4 | 4.1 |
| 0.45 | 2.9 | 0.45 | 2.7 | 0.45 | 6.5 | 0.45 | 4.1 |
| 0.5 | 2.9 | 0.5 | 2.7 | 0.5 | 6.4 | 0.5 | 4.1 |
| 0.55 | 2.9 | 0.55 | 2.7 | 0.55 | 6.4 | 0.55 | 4.1 |
| 0.6 | 2.9 | 0.6 | 2.7 | 0.6 | 6.4 | 0.6 | 4.0 |
| 0.65 | 2.9 | 0.65 | 2.7 | 0.65 | 6.4 | 0.65 | 4.0 |
| 0.7 | 2.9 | 0.7 | 2.7 | 0.7 | 6.3 | 0.7 | 4.0 |
| 0.75 | 2.9 | 0.75 | 2.7 | 0.75 | 6.1 | 0.75 | 3.9 |
| 0.8 | 2.7 | 0.8 | 2.6 | 0.8 | 5.8 | 0.8 | 3.7 |
| 0.85 | 2.5 | 0.85 | 2.4 | 0.85 | 5.3 | 0.85 | 3.4 |
| 0.9 | 2.2 | 0.9 | 2.1 | 0.9 | 4.5 | 0.9 | 2.9 |
| 0.95 | 1.8 | 0.95 | 1.7 | 0.95 | 3.2 | 0.95 | 2.2 |
| 1 | 1.2 | 1 | 1.2 | 1 | 1.2 | 1 | 1.2 |

HF - HFC-245cb - HCFO-1233zdE - HFO-1234zeE

| Organics 0.9 F245cb + 0.05 F1233zdE + 0.05 F1234zeE | | Organics 0.05 F245cb + 0.9 F1233zdE + 0.05 F1234zeE | | Organics 0.05 F245cb + 0.05 F1233zdE + 0.9 F1234zeE | | Organics 0.4 F245cb + 0.3 F1233zdE + 0.3 F1234zeE | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.5 | 0 | 1.7 | 0 | 4.7 | 0 | 3.8 |
| 0.05 | 5.7 | 0.05 | 2.8 | 0.05 | 5.7 | 0.05 | 4.9 |
| 0.1 | 5.7 | 0.1 | 2.8 | 0.1 | 5.7 | 0.1 | 4.9 |
| 0.15 | 5.7 | 0.15 | 2.8 | 0.15 | 5.7 | 0.15 | 4.9 |
| 0.2 | 5.7 | 0.2 | 2.8 | 0.2 | 5.7 | 0.2 | 4.9 |
| 0.25 | 5.7 | 0.25 | 2.8 | 0.25 | 5.7 | 0.25 | 4.9 |
| 0.3 | 5.7 | 0.3 | 2.8 | 0.3 | 5.7 | 0.3 | 4.9 |
| 0.35 | 5.7 | 0.35 | 2.8 | 0.35 | 5.7 | 0.35 | 4.9 |
| 0.4 | 5.7 | 0.4 | 2.8 | 0.4 | 5.7 | 0.4 | 4.9 |
| 0.45 | 5.7 | 0.45 | 2.8 | 0.45 | 5.7 | 0.45 | 4.9 |
| 0.5 | 5.7 | 0.5 | 2.8 | 0.5 | 5.7 | 0.5 | 4.9 |
| 0.55 | 5.7 | 0.55 | 2.8 | 0.55 | 5.6 | 0.55 | 4.9 |
| 0.6 | 5.7 | 0.6 | 2.8 | 0.6 | 5.5 | 0.6 | 4.9 |
| 0.65 | 5.7 | 0.65 | 2.8 | 0.65 | 5.5 | 0.65 | 4.9 |
| 0.7 | 5.7 | 0.7 | 2.8 | 0.7 | 5.3 | 0.7 | 4.9 |
| 0.75 | 5.7 | 0.75 | 2.8 | 0.75 | 5.1 | 0.75 | 4.9 |
| 0.8 | 5.7 | 0.8 | 2.7 | 0.8 | 4.8 | 0.8 | 4.7 |
| 0.85 | 5.6 | 0.85 | 2.5 | 0.85 | 4.3 | 0.85 | 4.3 |
| 0.9 | 4.8 | 0.9 | 2.2 | 0.9 | 3.6 | 0.9 | 3.7 |
| 0.95 | 3.4 | 0.95 | 1.8 | 0.95 | 2.6 | 0.95 | 2.7 |
| 1 | 1.2 | 1 | 1.2 | 1 | 1.2 | 1 | 1.2 |

-continued

| HF - HFC-245cb - HCFO-1233zdE - HFO-1234zeZ | | | | | | | |
|---|---|---|---|---|---|---|---|
| Organics 0.9 F245cb + 0.05 F1233zdE + 0.05 F1234zeZ | | Organics 0.05 F245cb + 0.9 F1233zdE + 0.05 F1234zeZ | | Organics 0.05 F245cb + 0.05 F1233zdE + 0.9 F1234zeZ | | Organics 0.4 F245cb + 0.3 F1233zdE + 0.3 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.3 | 0 | 1.5 | 0 | 1.3 | 0 | 2.8 |
| 0.05 | 5.5 | 0.05 | 2.5 | 0.05 | 3.0 | 0.05 | 3.9 |
| 0.1 | 5.5 | 0.1 | 2.6 | 0.1 | 3.0 | 0.1 | 3.9 |
| 0.15 | 5.5 | 0.15 | 2.6 | 0.15 | 3.0 | 0.15 | 3.9 |
| 0.2 | 5.5 | 0.2 | 2.6 | 0.2 | 3.0 | 0.2 | 3.9 |
| 0.25 | 5.5 | 0.25 | 2.6 | 0.25 | 3.0 | 0.25 | 3.9 |
| 0.3 | 5.5 | 0.3 | 2.6 | 0.3 | 3.0 | 0.3 | 4.0 |
| 0.35 | 5.5 | 0.35 | 2.6 | 0.35 | 3.0 | 0.35 | 4.0 |
| 0.4 | 5.5 | 0.4 | 2.6 | 0.4 | 3.0 | 0.4 | 4.0 |
| 0.45 | 5.5 | 0.45 | 2.6 | 0.45 | 3.0 | 0.45 | 4.0 |
| 0.5 | 5.5 | 0.5 | 2.6 | 0.5 | 3.0 | 0.5 | 4.0 |
| 0.55 | 5.5 | 0.55 | 2.6 | 0.55 | 3.0 | 0.55 | 4.0 |
| 0.6 | 5.5 | 0.6 | 2.6 | 0.6 | 3.0 | 0.6 | 4.0 |
| 0.65 | 5.5 | 0.65 | 2.7 | 0.65 | 3.1 | 0.65 | 4.0 |
| 0.7 | 5.6 | 0.7 | 2.7 | 0.7 | 3.1 | 0.7 | 4.1 |
| 0.75 | 5.6 | 0.75 | 2.7 | 0.75 | 3.1 | 0.75 | 4.1 |
| 0.8 | 5.6 | 0.8 | 2.5 | 0.8 | 2.3 | 0.8 | 4.1 |
| 0.85 | 5.5 | 0.85 | 2.4 | 0.85 | 2.7 | 0.85 | 3.8 |
| 0.9 | 4.8 | 0.9 | 2.1 | 0.9 | 2.4 | 0.9 | 3.3 |
| 0.95 | 3.4 | 0.95 | 1.7 | 0.95 | 1.9 | 0.95 | 2.5 |
| 1 | 1.2 | 1 | 1.2 | 1 | 1.2 | 1 | 1.2 |

| HF - HFC-245cb - HCFO-1233zdE - HFO-1243zf | | | | | | | |
|---|---|---|---|---|---|---|---|
| Organics 0.9 F245cb + 0.05 F1233zdE + 0.05 F1243zf | | Organics 0.05 F245cb + 0.9 F1233zdE + 0.05 F1243zf | | Organics 0.05 F245cb + 0.05 F1233zdE + 0.9 F1243zf | | Organics 0.4 F245cb + 0.3 F1233zdE + 0.3 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.6 | 0 | 1.8 | 0 | 5.6 | 0 | 4.2 |
| 0.05 | 5.7 | 0.05 | 2.9 | 0.05 | 6.6 | 0.05 | 5.3 |
| 0.1 | 5.7 | 0.1 | 2.9 | 0.1 | 6.6 | 0.1 | 5.3 |
| 0.15 | 5.7 | 0.15 | 2.9 | 0.15 | 6.6 | 0.15 | 5.3 |
| 0.2 | 5.7 | 0.2 | 2.9 | 0.2 | 6.6 | 0.2 | 5.3 |
| 0.25 | 5.7 | 0.25 | 2.9 | 0.25 | 6.6 | 0.25 | 5.3 |
| 0.3 | 5.7 | 0.3 | 2.9 | 0.3 | 6.6 | 0.3 | 5.3 |
| 0.35 | 5.7 | 0.35 | 2.9 | 0.35 | 6.6 | 0.35 | 5.3 |
| 0.4 | 5.7 | 0.4 | 2.9 | 0.4 | 6.6 | 0.4 | 5.3 |
| 0.45 | 5.7 | 0.45 | 2.9 | 0.45 | 6.6 | 0.45 | 5.3 |
| 0.5 | 5.7 | 0.5 | 2.9 | 0.5 | 6.6 | 0.5 | 5.3 |
| 0.55 | 5.7 | 0.55 | 2.9 | 0.55 | 6.6 | 0.55 | 5.3 |
| 0.6 | 5.7 | 0.6 | 2.9 | 0.6 | 6.6 | 0.6 | 5.3 |
| 0.65 | 5.7 | 0.65 | 2.9 | 0.65 | 6.6 | 0.65 | 5.3 |
| 0.7 | 5.8 | 0.7 | 2.9 | 0.7 | 6.4 | 0.7 | 5.3 |
| 0.75 | 5.8 | 0.75 | 2.9 | 0.75 | 5.2 | 0.75 | 5.1 |
| 0.8 | 5.8 | 0.8 | 2.8 | 0.8 | 6.0 | 0.8 | 4.7 |
| 0.85 | 5.7 | 0.85 | 2.6 | 0.85 | 5.5 | 0.85 | 4.1 |
| 0.9 | 4.9 | 0.9 | 2.3 | 0.9 | 4.7 | 0.9 | 2.9 |
| 0.95 | 3.5 | 0.95 | 1.8 | 0.95 | 3.3 | 0.95 | 1.2 |
| 1 | 1.2 | 1 | 1.2 | 1 | 1.2 | 1 | 1.2 |

| HF - HCFO-1233zdE - HFO-1234zeE - HFO-1234zeZ | | | | | | | |
|---|---|---|---|---|---|---|---|
| Organics 0.9 1233zdE + 0.05 1234zeE + 0.05 1234zeZ | | Organics 0.051233zdE + 0.9 1234zeE + 0.05 1234zeZ | | Organics 0.05 1233zdE + 0.05 1234zeE + 0.9 1234zeZ | | Organics 0.4 1233zdE + 0.3 1234zeE + 0.3 1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.5 | 0 | 4.5 | 0 | 1.9 | 0 | 2.6 |
| 0.05 | 2.6 | 0.05 | 5.5 | 0.05 | 3.0 | 0.05 | 3.7 |

-continued

| | | | | | | | |
|---|---|---|---|---|---|---|---|
| 0.1 | 2.6 | 0.1 | 5.5 | 0.1 | 3.0 | 0.1 | 3.6 |
| 0.15 | 2.6 | 0.15 | 5.5 | 0.15 | 3.0 | 0.15 | 3.6 |
| 0.2 | 2.6 | 0.2 | 5.5 | 0.2 | 3.0 | 0.2 | 3.6 |
| 0.25 | 2.6 | 0.25 | 5.5 | 0.25 | 3.0 | 0.25 | 3.6 |
| 0.3 | 2.6 | 0.3 | 5.5 | 0.3 | 3.0 | 0.3 | 3.6 |
| 0.35 | 2.6 | 0.35 | 5.5 | 0.35 | 3.0 | 0.35 | 3.6 |
| 0.4 | 2.6 | 0.4 | 5.5 | 0.4 | 3.0 | 0.4 | 3.6 |
| 0.45 | 2.6 | 0.45 | 5.5 | 0.45 | 3.0 | 0.45 | 3.6 |
| 0.5 | 2.6 | 0.5 | 5.5 | 0.5 | 3.0 | 0.5 | 3.6 |
| 0.55 | 2.6 | 0.55 | 5.4 | 0.55 | 3.0 | 0.55 | 3.6 |
| 0.6 | 2.6 | 0.6 | 5.4 | 0.6 | 3.0 | 0.6 | 3.6 |
| 0.65 | 2.6 | 0.65 | 5.3 | 0.65 | 3.0 | 0.65 | 3.6 |
| 0.7 | 2.6 | 0.7 | 5.1 | 0.7 | 3.0 | 0.7 | 3.5 |
| 0.75 | 2.6 | 0.75 | 4.9 | 0.75 | 3.0 | 0.75 | 3.4 |
| 0.8 | 2.5 | 0.8 | 4.6 | 0.8 | 2.9 | 0.8 | 3.2 |
| 0.85 | 2.3 | 0.85 | 4.1 | 0.85 | 2.7 | 0.85 | 2.9 |
| 0.9 | 2.0 | 0.9 | 3.4 | 0.9 | 2.3 | 0.9 | 2.5 |
| 0.95 | 1.7 | 0.95 | 2.5 | 0.95 | 1.9 | 0.95 | 2.0 |
| 1 | 1.2 | 1 | 1.2 | 1 | 1.2 | 1 | 1.2 |

HF - HCFO-1233zdE - HFO-1234zeE - HFO-1243zf

| Organics 0.9 F1233zdE + 0.05 F1234zeE + 0.05 F1243zf | | Organics 0.05 F1233zdE + 0.9 F1234zeE + 0.05 F1243zf | | Organics 0.05 F1233zdE + 0.05 F1234zeE + 0.9 F1243zf | | Organics 0.4 F1233zdE + 0.3 F1234zeE + 0.3 F1243zf | |
|---|---|---|---|---|---|---|---|
| HF HF | PRESSURE PRES bar | HF HF | PRESSURE PRES bar | HF HF | PRESSURE PRES bar | HF HF | PRESSURE PRES bar |
| 0 | 1.8 | 0 | 4.8 | 0 | 5.6 | 0 | 3.9 |
| 0.05 | 2.9 | 0.05 | 5.7 | 0.05 | 6.6 | 0.05 | 5.0 |
| 0.1 | 2.9 | 0.1 | 5.7 | 0.1 | 6.6 | 0.1 | 5.0 |
| 0.15 | 2.9 | 0.15 | 5.7 | 0.15 | 6.6 | 0.15 | 5.0 |
| 0.2 | 2.9 | 0.2 | 5.7 | 0.2 | 6.6 | 0.2 | 5.0 |
| 0.25 | 2.9 | 0.25 | 5.7 | 0.25 | 6.6 | 0.25 | 5.0 |
| 0.3 | 2.9 | 0.3 | 5.7 | 0.3 | 6.6 | 0.3 | 5.0 |
| 0.35 | 2.9 | 0.35 | 5.7 | 0.35 | 6.6 | 0.35 | 5.0 |
| 0.4 | 2.9 | 0.4 | 5.7 | 0.4 | 6.6 | 0.4 | 4.9 |
| 0.45 | 2.9 | 0.45 | 5.7 | 0.45 | 6.6 | 0.45 | 4.9 |
| 0.5 | 2.9 | 0.5 | 5.7 | 0.5 | 6.6 | 0.5 | 4.9 |
| 0.55 | 2.9 | 0.55 | 5.6 | 0.55 | 6.5 | 0.55 | 4.9 |
| 0.6 | 2.9 | 0.6 | 5.6 | 0.6 | 6.5 | 0.6 | 4.9 |
| 0.65 | 2.9 | 0.65 | 5.5 | 0.65 | 6.5 | 0.65 | 4.9 |
| 0.7 | 2.8 | 0.7 | 5.3 | 0.7 | 6.4 | 0.7 | 4.8 |
| 0.75 | 2.8 | 0.75 | 5.1 | 0.75 | 6.2 | 0.75 | 4.6 |
| 0.8 | 2.7 | 0.8 | 4.8 | 0.8 | 5.9 | 0.8 | 4.3 |
| 0.85 | 2.5 | 0.85 | 4.3 | 0.85 | 5.4 | 0.85 | 3.9 |
| 0.9 | 2.2 | 0.9 | 3.6 | 0.9 | 4.6 | 0.9 | 3.3 |
| 0.95 | 1.8 | 0.95 | 2.6 | 0.95 | 3.3 | 0.95 | 2.5 |
| 1 | 1.2 | 1 | 1.2 | 1 | 1.2 | 1 | 1.2 |

HF - HCFO-1233zdE - HFO-1234zeZ - HFO-1243zf

| Organics 0.9 F1233zdE + 0.05 F1234zeZ + 0.05 F1243zf | | Organics 0.05 F1233zdE + 0.9 F1234zeZ + 0.05 F1243zf | | Organics 0.05 F1233zdE + 0.05 F1234zeZ + 0.9 F1243zf | | Organics 0.4 F1233zdE + 0.3 F1234zeZ + 0.3 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.6 | 0 | 2.0 | 0 | 5.5 | 0 | 3.0 |
| 0.05 | 2.7 | 0.05 | 3.1 | 0.05 | 6.4 | 0.05 | 4.1 |
| 0.1 | 2.7 | 0.1 | 3.1 | 0.1 | 6.5 | 0.1 | 4.1 |
| 0.15 | 2.7 | 0.15 | 3.1 | 0.15 | 6.5 | 0.15 | 4.1 |
| 0.2 | 2.7 | 0.2 | 3.1 | 0.2 | 6.5 | 0.2 | 4.1 |
| 0.25 | 2.7 | 0.25 | 3.1 | 0.25 | 6.5 | 0.25 | 4.1 |
| 0.3 | 2.7 | 0.3 | 3.1 | 0.3 | 6.4 | 0.3 | 4.1 |
| 0.35 | 2.7 | 0.35 | 3.1 | 0.35 | 6.4 | 0.35 | 4.1 |
| 0.4 | 2.7 | 0.4 | 3.1 | 0.4 | 6.4 | 0.4 | 4.1 |
| 0.45 | 2.7 | 0.45 | 3.1 | 0.45 | 6.4 | 0.45 | 4.1 |
| 0.5 | 2.7 | 0.5 | 3.1 | 0.5 | 6.4 | 0.5 | 4.1 |
| 0.55 | 2.7 | 0.55 | 3.1 | 0.55 | 6.4 | 0.55 | 4.1 |
| 0.6 | 2.7 | 0.6 | 3.1 | 0.6 | 6.4 | 0.6 | 4.1 |
| 0.65 | 2.7 | 0.65 | 3.1 | 0.65 | 6.3 | 0.65 | 4.0 |
| 0.7 | 2.7 | 0.7 | 3.1 | 0.7 | 6.3 | 0.7 | 4.0 |

-continued

| | | | | | | | |
|---|---|---|---|---|---|---|---|
| 0.75 | 2.7 | 0.75 | 3.1 | 0.75 | 6.1 | 0.75 | 3.9 |
| 0.8 | 2.6 | 0.8 | 3.0 | 0.8 | 5.8 | 0.8 | 3.7 |
| 0.85 | 2.4 | 0.85 | 2.7 | 0.85 | 5.3 | 0.85 | 3.4 |
| 0.9 | 2.1 | 0.9 | 2.4 | 0.9 | 4.5 | 0.9 | 2.9 |
| 0.95 | 1.7 | 0.95 | 1.9 | 0.95 | 3.2 | 0.95 | 2.2 |
| 1 | 1.2 | 1 | 1.2 | 1 | 1.2 | 1 | 1.2 |

HF - HFO-1234yf - HCFO-1233zdE - HFC-245cb

| Organics 0.9 F1234yf + 0.05 F1233zdE + 0.05 F245cb | | Organics 0.4 F1234yf + 0.3 F1233zdE + 0.3 F245cb | | Organics 0.05 F1234yf + 0.9 F1233zdE + 0.05 F245cb | | Organics 0.05 F1234yf + 0.05 F1233zdE + 0.9 F245cb | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 4.6 | 0 | 1.8 | 0 | 4.6 |
| 0.05 | 7.4 | 0.05 | 5.7 | 0.05 | 2.9 | 0.05 | 5.8 |
| 0.1 | 7.4 | 0.1 | 5.7 | 0.1 | 2.9 | 0.1 | 5.8 |
| 0.15 | 7.4 | 0.15 | 5.7 | 0.15 | 2.9 | 0.15 | 5.8 |
| 0.2 | 7.4 | 0.2 | 5.7 | 0.2 | 2.9 | 0.2 | 5.8 |
| 0.25 | 7.4 | 0.25 | 5.7 | 0.25 | 2.9 | 0.25 | 5.8 |
| 0.3 | 7.4 | 0.3 | 5.7 | 0.3 | 2.9 | 0.3 | 5.8 |
| 0.35 | 7.4 | 0.35 | 5.7 | 0.35 | 2.9 | 0.35 | 5.8 |
| 0.4 | 7.4 | 0.4 | 5.7 | 0.4 | 2.9 | 0.4 | 5.8 |
| 0.45 | 7.4 | 0.45 | 5.7 | 0.45 | 2.9 | 0.45 | 5.8 |
| 0.5 | 7.4 | 0.5 | 5.7 | 0.5 | 2.9 | 0.5 | 5.8 |
| 0.55 | 7.4 | 0.55 | 5.7 | 0.55 | 2.9 | 0.55 | 5.8 |
| 0.6 | 7.4 | 0.6 | 5.7 | 0.6 | 2.9 | 0.6 | 5.8 |
| 0.65 | 7.4 | 0.65 | 5.8 | 0.65 | 2.9 | 0.65 | 5.8 |
| 0.7 | 7.4 | 0.7 | 5.8 | 0.7 | 2.9 | 0.7 | 5.8 |
| 0.75 | 7.3 | 0.75 | 5.8 | 0.75 | 2.9 | 0.75 | 5.8 |
| 0.8 | 7.0 | 0.8 | 5.6 | 0.8 | 2.8 | 0.8 | 5.8 |
| 0.85 | 6.4 | 0.85 | 5.1 | 0.85 | 2.6 | 0.85 | 5.7 |
| 0.9 | 5.4 | 0.9 | 4.4 | 0.9 | 2.3 | 0.9 | 4.9 |
| 0.95 | 2.7 | 0.95 | 3.1 | 0.95 | 1.8 | 0.95 | 3.5 |
| 1 | 1.2 | 1 | 1.2 | 1 | 1.2 | 1 | 1.2 |

HF - HCFO-1233xf - HFO-1234yf - HCFO-1233zdE

| Organics 0.9 F1233xf + 0.05 F1234yf + 0.05 F1233zdE | | Organics 0.05 F1233xf + 0.9 F1234yf + 0.05 F1233zdE | | Organics 0.05 F1233xf + 0.05 F1234yf + 0.9 F1233zdE | | Organics 0.4 F1233xf + 0.3 F1234yf + 0.3 F1233zdE | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 6.3 | 0 | 1.7 | 0 | 3.2 |
| 0.05 | 3.0 | 0.05 | 7.3 | 0.05 | 2.8 | 0.05 | 4.3 |
| 0.1 | 3.0 | 0.1 | 7.3 | 0.1 | 2.8 | 0.1 | 4.3 |
| 0.15 | 3.0 | 0.15 | 7.3 | 0.15 | 2.8 | 0.15 | 4.3 |
| 0.2 | 2.9 | 0.2 | 7.3 | 0.2 | 2.8 | 0.2 | 4.3 |
| 0.25 | 2.9 | 0.25 | 7.3 | 0.25 | 2.8 | 0.25 | 4.3 |
| 0.3 | 2.9 | 0.3 | 7.3 | 0.3 | 2.8 | 0.3 | 4.3 |
| 0.35 | 2.9 | 0.35 | 7.3 | 0.35 | 2.8 | 0.35 | 4.3 |
| 0.4 | 2.9 | 0.4 | 7.3 | 0.4 | 2.8 | 0.4 | 4.3 |
| 0.45 | 2.9 | 0.45 | 7.3 | 0.45 | 2.7 | 0.45 | 4.3 |
| 0.5 | 2.9 | 0.5 | 7.3 | 0.5 | 2.7 | 0.5 | 4.3 |
| 0.55 | 2.9 | 0.55 | 7.3 | 0.55 | 2.7 | 0.55 | 4.3 |
| 0.6 | 2.9 | 0.6 | 7.3 | 0.6 | 2.7 | 0.6 | 4.3 |
| 0.65 | 2.9 | 0.65 | 7.3 | 0.65 | 2.7 | 0.65 | 4.3 |
| 0.7 | 2.9 | 0.7 | 7.3 | 0.7 | 2.7 | 0.7 | 4.3 |
| 0.75 | 2.9 | 0.75 | 7.1 | 0.75 | 2.7 | 0.75 | 4.2 |
| 0.8 | 2.8 | 0.8 | 6.8 | 0.8 | 2.6 | 0.8 | 4.0 |
| 0.85 | 2.6 | 0.85 | 6.2 | 0.85 | 2.4 | 0.85 | 3.7 |
| 0.9 | 2.3 | 0.9 | 5.3 | 0.9 | 2.1 | 0.9 | 3.1 |
| 0.95 | 1.8 | 0.95 | 3.7 | 0.95 | 1.7 | 0.95 | 2.3 |
| 1 | 1.2 | 1 | 1.2 | 1 | 1.2 | 1 | 1.2 |

-continued

| HF - HFO-1234yf - HFO-1234zeE - HCFO-1233zdE | | | | | | | |
|---|---|---|---|---|---|---|---|
| Organics 0.9 F1234yf + 0.05 F1234zeE + 0.05 F1233zdE | | Organics 0.05 F1234yf + 0.9 F1234zeE + 0.05 F1233zdE | | Organics 0.05 F1234yf + 0.05 F1234zeE + 0.9 F1233zdE | | Organics 0.4 F1234yf + 0.3 F1234zeE + 0.3 F1233zdE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 4.8 | 0 | 1.8 | 0 | 4.7 |
| 0.05 | 7.4 | 0.05 | 5.8 | 0.05 | 2.9 | 0.05 | 5.7 |
| 0.1 | 7.4 | 0.1 | 5.8 | 0.1 | 2.9 | 0.1 | 5.7 |
| 0.15 | 7.4 | 0.15 | 5.8 | 0.15 | 2.9 | 0.15 | 5.7 |
| 0.2 | 7.4 | 0.2 | 5.8 | 0.2 | 2.9 | 0.2 | 5.7 |
| 0.25 | 7.4 | 0.25 | 5.8 | 0.25 | 2.9 | 0.25 | 5.7 |
| 0.3 | 7.4 | 0.3 | 5.8 | 0.3 | 2.9 | 0.3 | 5.7 |
| 0.35 | 7.4 | 0.35 | 5.8 | 0.35 | 2.9 | 0.35 | 5.7 |
| 0.4 | 7.4 | 0.4 | 5.8 | 0.4 | 2.9 | 0.4 | 5.7 |
| 0.45 | 7.4 | 0.45 | 5.8 | 0.45 | 2.9 | 0.45 | 5.7 |
| 0.5 | 7.4 | 0.5 | 5.7 | 0.5 | 2.9 | 0.5 | 5.7 |
| 0.55 | 7.4 | 0.55 | 5.7 | 0.55 | 2.9 | 0.55 | 5.7 |
| 0.6 | 7.4 | 0.6 | 5.6 | 0.6 | 2.9 | 0.6 | 5.7 |
| 0.65 | 7.4 | 0.65 | 5.5 | 0.65 | 2.9 | 0.65 | 5.7 |
| 0.7 | 7.4 | 0.7 | 5.4 | 0.7 | 2.9 | 0.7 | 5.6 |
| 0.75 | 7.2 | 0.75 | 5.1 | 0.75 | 2.9 | 0.75 | 5.4 |
| 0.8 | 6.9 | 0.8 | 4.8 | 0.8 | 2.7 | 0.8 | 5.1 |
| 0.85 | 6.9 | 0.85 | 4.3 | 0.85 | 2.5 | 0.85 | 4.7 |
| 0.9 | 5.3 | 0.9 | 3.6 | 0.9 | 2.2 | 0.9 | 3.9 |
| 0.95 | 3.7 | 0.95 | 2.6 | 0.95 | 1.8 | 0.95 | 2.8 |
| 1 | 1.2 | 1 | 1.2 | 1 | 1.2 | 1 | 1.2 |

| HF - HFO-1234yf - HFO-1234zeZ - HCFO-1233zdE | | | | | | | |
|---|---|---|---|---|---|---|---|
| Organics 0.9 F1234yf + 0.05 F1234zeZ + 0.05 F1233zdE | | Organics 0.05 F1234yf + 0.9 F1234zeZ + 0.05 F1233zdE | | Organics 0.05 F1234yf + 0.05 F1234zeZ + 0.9 F1233zdE | | Organics 0.4 F1234yf + 0.3 F1234zeZ + 0.3 F1233zdE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.3 | 0 | 2.0 | 0 | 1.7 | 0 | 3.8 |
| 0.05 | 7.3 | 0.05 | 3.2 | 0.05 | 2.8 | 0.05 | 4.8 |
| 0.1 | 7.3 | 0.1 | 3.2 | 0.1 | 2.8 | 0.1 | 4.8 |
| 0.15 | 7.3 | 0.15 | 3.2 | 0.15 | 2.8 | 0.15 | 4.8 |
| 0.2 | 7.3 | 0.2 | 3.2 | 0.2 | 2.8 | 0.2 | 4.8 |
| 0.25 | 7.3 | 0.25 | 3.2 | 0.25 | 2.8 | 0.25 | 4.8 |
| 0.3 | 7.3 | 0.3 | 3.2 | 0.3 | 2.8 | 0.3 | 4.8 |
| 0.35 | 7.3 | 0.35 | 3.1 | 0.35 | 2.8 | 0.35 | 4.8 |
| 0.4 | 7.3 | 0.4 | 3.1 | 0.4 | 2.8 | 0.4 | 4.8 |
| 0.45 | 7.3 | 0.45 | 3.1 | 0.45 | 2.8 | 0.45 | 4.8 |
| 0.5 | 7.3 | 0.5 | 3.1 | 0.5 | 2.8 | 0.5 | 4.8 |
| 0.55 | 7.3 | 0.55 | 3.1 | 0.55 | 2.8 | 0.55 | 4.8 |
| 0.6 | 7.3 | 0.6 | 3.1 | 0.6 | 2.8 | 0.6 | 4.8 |
| 0.65 | 7.3 | 0.65 | 3.1 | 0.65 | 2.8 | 0.65 | 4.8 |
| 0.7 | 7.3 | 0.7 | 3.1 | 0.7 | 2.7 | 0.7 | 4.8 |
| 0.75 | 7.1 | 0.75 | 3.1 | 0.75 | 2.7 | 0.75 | 4.7 |
| 0.8 | 6.8 | 0.8 | 3.0 | 0.8 | 2.6 | 0.8 | 4.5 |
| 0.85 | 6.2 | 0.85 | 2.8 | 0.85 | 2.4 | 0.85 | 4.1 |
| 0.9 | 5.3 | 0.9 | 2.4 | 0.9 | 2.2 | 0.9 | 3.5 |
| 0.95 | 3.7 | 0.95 | 1.9 | 0.95 | 1.7 | 0.95 | 2.8 |
| 1 | 1.2 | 1 | 1.2 | 1 | 1.2 | 1 | 1.2 |

-continued

| HF - HFO-1234yf - HCFO-1233zdE - HFO-1243zf | | | | | | | |
|---|---|---|---|---|---|---|---|
| Organics 0.9 F1234yf + 0.05 F1233zdE + 0.05 F1243zf | | Organics 0.05 F1234yf + 0.9 F1233zdE + 0.05 F1243zf | | Organics 0.05 F1234yf + 0.05 F1233zdE + 0.9 F1243zf | | Organics 0.4 F1234yf + 0.3 F1233zdE + 0.3 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 1.9 | 0 | 5.7 | 0 | 5.0 |
| 0.05 | 7.5 | 0.05 | 3.0 | 0.05 | 6.7 | 0.05 | 6.0 |
| 0.1 | 7.5 | 0.1 | 3.0 | 0.1 | 6.7 | 0.1 | 6.0 |
| 0.15 | 7.5 | 0.15 | 3.0 | 0.15 | 6.7 | 0.15 | 6.0 |
| 0.2 | 7.4 | 0.2 | 3.0 | 0.2 | 6.7 | 0.2 | 6.0 |
| 0.25 | 7.4 | 0.25 | 3.0 | 0.25 | 6.7 | 0.25 | 6.0 |
| 0.3 | 7.5 | 0.3 | 3.0 | 0.3 | 6.7 | 0.3 | 6.0 |
| 0.35 | 7.5 | 0.35 | 3.0 | 0.35 | 6.7 | 0.35 | 6.0 |
| 0.4 | 7.5 | 0.4 | 3.0 | 0.4 | 6.7 | 0.4 | 6.0 |
| 0.45 | 7.5 | 0.45 | 3.0 | 0.45 | 6.7 | 0.45 | 6.0 |
| 0.5 | 7.5 | 0.5 | 3.0 | 0.5 | 6.6 | 0.5 | 6.0 |
| 0.55 | 7.5 | 0.55 | 3.0 | 0.55 | 6.6 | 0.55 | 6.0 |
| 0.6 | 7.5 | 0.6 | 3.0 | 0.6 | 6.6 | 0.6 | 6.0 |
| 0.65 | 7.5 | 0.65 | 3.0 | 0.65 | 6.6 | 0.65 | 6.0 |
| 0.7 | 7.4 | 0.7 | 3.0 | 0.7 | 6.5 | 0.7 | 6.0 |
| 0.75 | 7.3 | 0.75 | 3.0 | 0.75 | 6.3 | 0.75 | 5.8 |
| 0.8 | 7.0 | 0.8 | 2.8 | 0.8 | 6.0 | 0.8 | 5.5 |
| 0.85 | 6.4 | 0.85 | 2.6 | 0.85 | 5.5 | 0.85 | 5.1 |
| 0.9 | 5.4 | 0.9 | 2.3 | 0.9 | 4.7 | 0.9 | 4.3 |
| 0.95 | 3.7 | 0.95 | 1.8 | 0.95 | 3.3 | 0.95 | 3.1 |
| 1 | 1.2 | 1 | 1.2 | 1 | 1.2 | 1 | 1.2 |

Example 8: Temperature and Pressure Range of Quaternary Mixtures

| | Boiling point range | |
|---|---|---|
| Quaternary | Temperature ° C. | Pressure bar abs |
| HF-HCFO-1233xf-HFC-245cb-HCFO-1233zdE | 0 to 40 | ~1.0 to ~8.7 |
| HF-HCFO-1233xf-HCFO-1233zdE-HFO-1234zeE | 0 to 40 | ~1.0 to ~8.6 |
| HF-HCFO-1233xf-HCFO-1233zdE-HFO-1234zeZ | 0 to 40 | ~0.9 to ~4.8 |
| HF-HCFO-1233xf-HCFO-1233zdE-HFO-1243zf | 0 to 40 | ~1.0 to ~9.9 |
| HF-HFC-245cb-HCFO-1233zdE-HFO-1234zeE | 0 to 40 | ~1.0 to ~8.9 |
| HF-HFC-245cb-HCFO-1233zdE-HFO-1234zeZ | 0 to 40 | ~1.0 to ~8.9 |
| HF-HFC-245cb-HCFO-1233zdE-HFO-1243zf | 0 to 40 | ~1.1 to ~10.1 |
| HF-HCFO-1233zdE-HFO-1234zeE-HFO-1234zeZ | 0 to 40 | ~1.0 to ~8.6 |
| HF-HCFO-1233zdE-HFO-1234zeE-HFO-1243zf | 0 to 40 | ~1.1 to ~10.1 |
| HF-HCFO-1233zdE-HFO-1234zeZ-HFO-1243zf | 0 to 40 | ~1.0 to ~9.9 |
| HF-HFO-1234yf-HFC-245cb-HCFO-1233zdE | 0 to 40 | ~1.1 to ~11.3 |
| HF-HCFO-1233xf-HFO-1234yf-HCFO-1233zdE | 0 to 40 | ~1.0 to ~11.1 |
| HF-HFO-1234yf-HFO-1234zeE-HCFO-1233zdE | 0 to 40 | ~1.1 to ~11.3 |
| HF-HFO-1234yf-HFO-1234zeZ-HCFO-1233zdE | 0 to 40 | ~1.0 to ~11.0 |
| HF-HFO-1234yf-HCFO-1233zdE-HFO-1243zf | 0 to 40 | ~1.2 to ~11.3 |

Example 9: Decantation Range of Quaternary Mixtures

| | Decantation ranges Mass percentage of HF | | |
|---|---|---|---|
| Quaternary | Isotherm 0° C. | Isotherm 25° C. | Isotherm 40° C. |
| HF-HCFO-1233xf-HFC-245cb-HCFO-1233zdE | 5-80 | 5-75 | 5-70 |
| HF-HCFO-1233xf-HCFO-1233zdE-HFO-1234zeE | 5-75 | 5-65 | 5-55 |
| HF-HCFO-1233xf-HCFO-1233zdE-HFO-1234zeZ | 5-80 | 5-75 | 5-65 |
| HF-HCFO-1233xf-HCFO-1233zdE-HFO-1243zf | 5-75 | 5-70 | 10-60 |
| HF-HFC-245cb-HCFO-1233zdE-HFO-1234zeE | 5-75 | 5-70 | 10-65 |
| HF-HFC-245cb-HCFO-1233zdE-HFO-1234zeZ | 5-80 | 5-75 | 5-70 |
| HF-HFC-245cb-HCFO-1233zdE-HFO-1243zf | 5-75 | 5-70 | 15-65 |
| HF-HCFO-1233zdE-HFO-1234zeE-HFO-1234zeZ | 5-75 | 5-65 | 10-55 |
| HF-HCFO-1233zdE-HFO-1234zeE-HFO-1243zf | 5-70 | 10-60 | * |
| HF-HCFO-1233zdE-HFO-1234zeZ-HFO-1243zf | 5-75 | 5-70 | 10-55 |
| HF-HFO-1234yf-HFC-245cb-HCFO-1233zdE | 5-75 | 5-75 | 15-70 |
| HF-HCFO-1233xf-HFO-1234yf-HCFO-1233zdE | 5-75 | 5-70 | 10-60 |
| HF-HFO-1234yf-HFO-1234zeE-HCFO-1233zdE | 5-70 | 10-60 | * |
| HF-HFO-1234yf-HFO-1234zeZ-HCFO-1233zdE | 5-75 | 5-70 | 10-60 |
| HF-HFO-1234yf-HCFO-1233zdE-HFO-1243zf | 5-75 | 10-65 | * |

Example 10: Penternary Mixtures, Isotherm at 25° C.

| HF-HCFO-1233xf-HFC-245cb-HCFO-1233zdE-HFO-1234zeE | | | | | | | | | |
|---|---|---|---|---|---|---|---|---|---|
| Organics 0.9 F1233xf + 0.033 F1233zdE + 0.033 F245cb + 0.034 F1234zeZ | | Organics 0.033 F1233xf + 0.9 F1233zdE + 0.033 F245cb + 0.034 F1234zeZ | | Organics 0.033 F1233xf + 0.033 F1233zdE + 0.9 F245cb + 0.034 F1234zeZ | | Organics 0.034 F1233xf + 0.033 F1233zdE + 0.033 F245cb + 0.9 F1234zeZ | | Organics 0.25 F1233xf + 0.25 F1233zdE + 0.25 F245cb + 0.25 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 1.6 | 0 | 4.4 | 0 | 4.7 | 0 | 3.2 |
| 0.05 | 2.9 | 0.05 | 2.7 | 0.05 | 5.6 | 0.05 | 5.6 | 0.05 | 4.3 |
| 0.1 | 2.9 | 0.1 | 2.7 | 0.1 | 5.6 | 0.1 | 5.6 | 0.1 | 4.3 |
| 0.15 | 2.9 | 0.15 | 2.7 | 0.15 | 5.6 | 0.15 | 5.6 | 0.15 | 4.3 |
| 0.2 | 2.9 | 0.2 | 2.7 | 0.2 | 5.6 | 0.2 | 5.6 | 0.2 | 4.3 |
| 0.25 | 2.9 | 0.25 | 2.7 | 0.25 | 5.6 | 0.25 | 5.6 | 0.25 | 4.3 |
| 0.3 | 2.9 | 0.3 | 2.7 | 0.3 | 5.6 | 0.3 | 5.6 | 0.3 | 4.3 |
| 0.35 | 2.9 | 0.35 | 2.7 | 0.35 | 5.6 | 0.35 | 5.6 | 0.35 | 4.3 |
| 0.4 | 2.9 | 0.4 | 2.7 | 0.4 | 5.6 | 0.4 | 5.6 | 0.4 | 4.3 |
| 0.45 | 2.9 | 0.45 | 2.7 | 0.45 | 5.6 | 0.45 | 5.6 | 0.45 | 4.3 |
| 0.5 | 2.9 | 0.5 | 2.7 | 0.5 | 5.6 | 0.5 | 5.6 | 0.5 | 4.3 |
| 0.55 | 2.9 | 0.55 | 2.7 | 0.55 | 5.6 | 0.55 | 5.6 | 0.55 | 4.3 |
| 0.6 | 2.9 | 0.6 | 2.7 | 0.6 | 5.6 | 0.6 | 5.5 | 0.6 | 4.3 |
| 0.65 | 2.9 | 0.65 | 2.7 | 0.65 | 5.6 | 0.65 | 5.4 | 0.65 | 4.3 |
| 0.7 | 2.9 | 0.7 | 2.7 | 0.7 | 5.7 | 0.7 | 5.2 | 0.7 | 4.3 |
| 0.75 | 2.9 | 0.75 | 2.7 | 0.75 | 5.7 | 0.75 | 5.0 | 0.75 | 4.2 |
| 0.8 | 2.7 | 0.8 | 2.6 | 0.8 | 5.7 | 0.8 | 4.7 | 0.8 | 4.0 |
| 0.85 | 2.5 | 0.85 | 2.4 | 0.85 | 5.6 | 0.85 | 4.2 | 0.85 | 3.7 |
| 0.9 | 2.2 | 0.9 | 2.1 | 0.9 | 4.8 | 0.9 | 3.5 | 0.9 | 3.2 |
| 0.95 | 1.8 | 0.95 | 1.7 | 0.95 | 3.4 | 0.95 | 2.5 | 0.95 | 2.4 |
| 1 | 1.2 | 1 | 1.2 | 1 | 1.2 | 1 | 1.2 | 1 | 1.2 |

| HF-HCFO-1233xf-HFC-245cb-HCFO-1233zdE-HFO-1234zeE | | | | | | | | | |
|---|---|---|---|---|---|---|---|---|---|
| Organics 0.9 F1233xf + 0.033 F1233zdE + 0.033 F245cb + 0.034 F1234zeZ | | Organics 0.033 F1233xf + 0.9 F1233zdE + 0.033 F245cb + 0.034 F1234zeZ | | Organics 0.033 F1233xf + 0.033 F1233zdE + 0.9 F245cb + 0.034 F1234zeZ | | Organics 0.034 F1233xf + 0.033 F1233zdE + 0.033 F245cb + 0.9 F1234zeZ | | Organics 0.25 F1233xf + 0.25 F1233zdE + 0.25 F245cb + 0.25 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 1.5 | 0 | 4.3 | 0 | 1.9 | 0 | 2.3 |
| 0.05 | 2.8 | 0.05 | 2.6 | 0.05 | 5.5 | 0.05 | 3.0 | 0.05 | 3.5 |
| 0.1 | 2.8 | 0.1 | 2.6 | 0.1 | 5.5 | 0.1 | 3.0 | 0.1 | 3.5 |
| 0.15 | 2.8 | 0.15 | 2.6 | 0.15 | 5.5 | 0.15 | 3.0 | 0.15 | 3.5 |
| 0.2 | 2.8 | 0.2 | 2.6 | 0.2 | 5.5 | 0.2 | 3.0 | 0.2 | 3.5 |
| 0.25 | 2.8 | 0.25 | 2.6 | 0.25 | 5.5 | 0.25 | 3.0 | 0.25 | 3.5 |
| 0.3 | 2.8 | 0.3 | 2.6 | 0.3 | 5.5 | 0.3 | 3.0 | 0.3 | 3.5 |
| 0.35 | 2.8 | 0.35 | 2.6 | 0.35 | 5.5 | 0.35 | 3.0 | 0.35 | 3.5 |
| 0.4 | 2.8 | 0.4 | 2.6 | 0.4 | 5.5 | 0.4 | 3.0 | 0.4 | 3.5 |
| 0.45 | 2.8 | 0.45 | 2.6 | 0.45 | 5.5 | 0.45 | 3.0 | 0.45 | 3.5 |
| 0.5 | 2.8 | 0.5 | 2.6 | 0.5 | 5.5 | 0.5 | 3.0 | 0.5 | 3.5 |
| 0.55 | 2.8 | 0.55 | 2.6 | 0.55 | 5.5 | 0.55 | 3.0 | 0.55 | 3.5 |
| 0.6 | 2.8 | 0.6 | 2.6 | 0.6 | 5.5 | 0.6 | 3.0 | 0.6 | 3.5 |
| 0.65 | 2.8 | 0.65 | 2.6 | 0.65 | 5.5 | 0.65 | 3.0 | 0.65 | 3.6 |
| 0.7 | 2.8 | 0.7 | 2.6 | 0.7 | 5.5 | 0.7 | 3.0 | 0.7 | 3.6 |
| 0.75 | 2.8 | 0.75 | 2.6 | 0.75 | 5.5 | 0.75 | 3.0 | 0.75 | 3.6 |
| 0.8 | 2.7 | 0.8 | 2.5 | 0.8 | 5.5 | 0.8 | 2.9 | 0.8 | 3.5 |
| 0.85 | 2.5 | 0.85 | 2.3 | 0.85 | 5.5 | 0.85 | 2.7 | 0.85 | 3.3 |
| 0.9 | 2.2 | 0.9 | 2.1 | 0.9 | 4.8 | 0.9 | 2.4 | 0.9 | 2.8 |
| 0.95 | 1.8 | 0.95 | 1.7 | 0.95 | 3.4 | 0.95 | 1.9 | 0.95 | 2.2 |
| 1 | 1.2 | 1 | 1.2 | 1 | 1.2 | 1 | 1.2 | 1 | 1.2 |

-continued

| HF-HCFO-1233xf-HFC-245cb-HCFO-1233zdE-HFO-1243zf | | | | | | | | | |
|---|---|---|---|---|---|---|---|---|---|
| Organics 0.9 F1233xf + 0.033 F1233zdE + 0.033 F245cb + 0.034 F1243zf | | Organics 0.033 F1233xf + 0.9 F1233zdE + 0.033 F245cb + 0.034 F1234zf | | Organics 0.033 F1233xf + 0.033 F1233zdE + 0.9 F245cb + 0.034 F1234zf | | Organics 0.034 F1233xf + 0.033 F1233zdE + 0.033 F245cb + 0.9 F1234zf | | Organics 0.25 F1233xf + 0.25 F1233zdE + 0.25 F245cb + 0.25 F1234zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 1.6 | 0 | 4.5 | 0 | 5.6 | 0 | 3.5 |
| 0.05 | 3.0 | 0.05 | 2.8 | 0.05 | 5.7 | 0.05 | 6.5 | 0.05 | 4.6 |
| 0.1 | 3.0 | 0.1 | 2.8 | 0.1 | 5.7 | 0.1 | 6.5 | 0.1 | 4.6 |
| 0.15 | 3.0 | 0.15 | 2.8 | 0.15 | 5.7 | 0.15 | 6.5 | 0.15 | 4.6 |
| 0.2 | 3.0 | 0.2 | 2.8 | 0.2 | 5.7 | 0.2 | 6.5 | 0.2 | 4.6 |
| 0.25 | 3.0 | 0.25 | 2.8 | 0.25 | 5.7 | 0.25 | 6.5 | 0.25 | 4.6 |
| 0.3 | 3.0 | 0.3 | 2.8 | 0.3 | 5.7 | 0.3 | 6.5 | 0.3 | 4.6 |
| 0.35 | 2.9 | 0.35 | 2.8 | 0.35 | 5.7 | 0.35 | 6.5 | 0.35 | 4.6 |
| 0.4 | 2.9 | 0.4 | 2.8 | 0.4 | 5.7 | 0.4 | 6.5 | 0.4 | 4.6 |
| 0.45 | 2.9 | 0.45 | 2.7 | 0.45 | 5.7 | 0.45 | 6.5 | 0.45 | 4.6 |
| 0.5 | 2.9 | 0.5 | 2.7 | 0.5 | 5.7 | 0.5 | 6.5 | 0.5 | 4.6 |
| 0.55 | 2.9 | 0.55 | 2.7 | 0.55 | 5.7 | 0.55 | 6.5 | 0.55 | 4.6 |
| 0.6 | 2.9 | 0.6 | 2.7 | 0.6 | 5.7 | 0.6 | 6.5 | 0.6 | 4.6 |
| 0.65 | 2.9 | 0.65 | 2.7 | 0.65 | 5.7 | 0.65 | 6.4 | 0.65 | 4.6 |
| 0.7 | 2.9 | 0.7 | 2.7 | 0.7 | 5.7 | 0.7 | 6.4 | 0.7 | 4.7 |
| 0.75 | 2.9 | 0.75 | 2.7 | 0.75 | 5.7 | 0.75 | 6.2 | 0.75 | 4.6 |
| 0.8 | 2.9 | 0.8 | 2.6 | 0.8 | 5.7 | 0.8 | 5.9 | 0.8 | 4.4 |
| 0.85 | 2.8 | 0.85 | 2.4 | 0.85 | 5.6 | 0.85 | 5.4 | 0.85 | 4.1 |
| 0.9 | 2.3 | 0.9 | 2.2 | 0.9 | 4.6 | 0.9 | 4.6 | 0.9 | 3.5 |
| 0.95 | 1.6 | 0.95 | 1.8 | 0.95 | 3.4 | 0.95 | 3.3 | 0.95 | 2.6 |
| 1 | 1.2 | 1 | 1.2 | 1 | 1.2 | 1 | 1.2 | 1 | 1.2 |

| HF-HCFO-1233xf-HCFO-1233xdE-HFO-1234zeE-HFO-1234zeZ | | | | | | | | | |
|---|---|---|---|---|---|---|---|---|---|
| Organics 0.9 F1233xf + 0.033 F1234zeE + 0.033 F1233zdE + 0.034 F1234zeZ | | Organics 0.033 F1233xf + 0.9 F1234zeE + 0.033 F1233zdE + 0.034 F1234zeZ | | Organics 0.033 F1233xf + 0.033 F1234zeE + 0.9 F1233zdE + 0.034 F1234zeZ | | Organics 0.034 F1233xf + 0.033 F1234zeE + 0.033 F1233zdE + 0.9 F1234zeZ | | Organics 0.25 F1233xf + 0.25 F1234zeE + 0.25 F1233zdE + 0.25 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 4.6 | 0 | 1.5 | 0 | 1.9 | 0 | 2.4 |
| 0.05 | 2.8 | 0.05 | 5.5 | 0.05 | 2.6 | 0.05 | 3.0 | 0.05 | 3.5 |
| 0.1 | 2.8 | 0.1 | 5.5 | 0.1 | 2.6 | 0.1 | 3.0 | 0.1 | 3.5 |
| 0.15 | 2.8 | 0.15 | 5.5 | 0.15 | 2.6 | 0.15 | 3.0 | 0.15 | 3.5 |
| 0.2 | 2.8 | 0.2 | 5.5 | 0.2 | 2.6 | 0.2 | 3.0 | 0.2 | 3.5 |
| 0.25 | 2.8 | 0.25 | 5.5 | 0.25 | 2.6 | 0.25 | 3.0 | 0.25 | 3.5 |
| 0.3 | 2.8 | 0.3 | 5.5 | 0.3 | 2.6 | 0.3 | 3.0 | 0.3 | 3.5 |
| 0.35 | 2.8 | 0.35 | 5.5 | 0.35 | 2.6 | 0.35 | 3.0 | 0.35 | 3.5 |
| 0.4 | 2.8 | 0.4 | 5.5 | 0.4 | 2.6 | 0.4 | 3.0 | 0.4 | 3.5 |
| 0.45 | 2.8 | 0.45 | 5.5 | 0.45 | 2.6 | 0.45 | 3.0 | 0.45 | 3.5 |
| 0.5 | 2.8 | 0.5 | 5.5 | 0.5 | 2.6 | 0.5 | 3.0 | 0.5 | 3.5 |
| 0.55 | 2.8 | 0.55 | 5.4 | 0.55 | 2.6 | 0.55 | 3.0 | 0.55 | 3.4 |
| 0.6 | 2.8 | 0.6 | 5.4 | 0.6 | 2.6 | 0.6 | 3.0 | 0.6 | 3.4 |
| 0.65 | 2.8 | 0.65 | 5.3 | 0.65 | 2.6 | 0.65 | 3.0 | 0.65 | 3.4 |
| 0.7 | 2.8 | 0.7 | 5.1 | 0.7 | 2.5 | 0.7 | 3.0 | 0.7 | 3.4 |
| 0.75 | 2.7 | 0.75 | 4.9 | 0.75 | 2.5 | 0.75 | 3.0 | 0.75 | 3.3 |
| 0.8 | 2.6 | 0.8 | 4.6 | 0.8 | 2.4 | 0.8 | 2.8 | 0.8 | 3.1 |
| 0.85 | 2.4 | 0.85 | 4.1 | 0.85 | 2.3 | 0.85 | 2.6 | 0.85 | 2.9 |
| 0.9 | 2.1 | 0.9 | 3.4 | 0.9 | 2.0 | 0.9 | 2.3 | 0.9 | 2.5 |
| 0.95 | 1.7 | 0.95 | 2.5 | 0.95 | 1.7 | 0.95 | 1.9 | 0.95 | 1.9 |
| 1 | 1.2 | 1 | 1.2 | 1 | 1.2 | 1 | 1.2 | 1 | 1.2 |

-continued

HF-HCFO-1233xf-HCFO-1233zdE-HFO-1234zeE-HFO-1234zf

| Organics 0.9 F1233xf + 0.033 F1234zeE + 0.033 F1233zdE + 0.034 F1243zf | | Organics 0.033 F1233xf + 0.9 F1234zeE + 0.033 F1233zdE + 0.034 F1243zf | | Organics 0.033 F1233xf + 0.033 F1234zeE + 0.9 F1233zdE + 0.034 F1243zf | | Organics 0.034 F1233xf + 0.033 F1234zeE + 0.033 F1233zdE + 0.9 F1243zf | | Organics 0.25 F1233xf + 0.25 F1234zeE + 0.25 F1233zdE + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 4.7 | 0 | 1.7 | 0 | 5.6 | 0 | 3.6 |
| 0.05 | 3.0 | 0.05 | 5.7 | 0.05 | 2.8 | 0.05 | 6.5 | 0.05 | 4.7 |
| 0.1 | 3.0 | 0.1 | 5.7 | 0.1 | 2.8 | 0.1 | 6.5 | 0.1 | 4.7 |
| 0.15 | 3.0 | 0.15 | 5.7 | 0.15 | 2.8 | 0.15 | 6.5 | 0.15 | 4.7 |
| 0.2 | 3.0 | 0.2 | 5.7 | 0.2 | 2.8 | 0.2 | 6.5 | 0.2 | 4.7 |
| 0.25 | 3.0 | 0.25 | 5.7 | 0.25 | 2.8 | 0.25 | 6.5 | 0.25 | 4.6 |
| 0.3 | 2.9 | 0.3 | 5.7 | 0.3 | 2.7 | 0.3 | 6.5 | 0.3 | 4.6 |
| 0.35 | 2.9 | 0.35 | 5.7 | 0.35 | 2.7 | 0.35 | 6.5 | 0.35 | 4.6 |
| 0.4 | 2.9 | 0.4 | 5.7 | 0.4 | 2.7 | 0.4 | 6.5 | 0.4 | 4.6 |
| 0.45 | 2.9 | 0.45 | 5.7 | 0.45 | 2.7 | 0.45 | 6.5 | 0.45 | 4.6 |
| 0.5 | 2.9 | 0.5 | 5.6 | 0.5 | 2.7 | 0.5 | 6.5 | 0.5 | 4.6 |
| 0.55 | 2.9 | 0.55 | 5.6 | 0.55 | 2.7 | 0.55 | 6.5 | 0.55 | 4.6 |
| 0.6 | 2.9 | 0.6 | 5.5 | 0.6 | 2.7 | 0.6 | 6.5 | 0.6 | 4.6 |
| 0.65 | 2.9 | 0.65 | 5.4 | 0.65 | 2.7 | 0.65 | 6.4 | 0.65 | 4.5 |
| 0.7 | 2.9 | 0.7 | 5.3 | 0.7 | 2.7 | 0.7 | 6.3 | 0.7 | 4.5 |
| 0.75 | 2.9 | 0.75 | 5.0 | 0.75 | 2.7 | 0.75 | 6.2 | 0.75 | 4.3 |
| 0.8 | 2.7 | 0.8 | 4.7 | 0.8 | 2.6 | 0.8 | 5.9 | 0.8 | 4.1 |
| 0.85 | 2.5 | 0.85 | 4.2 | 0.85 | 2.4 | 0.85 | 5.4 | 0.85 | 3.7 |
| 0.9 | 2.2 | 0.9 | 3.5 | 0.9 | 2.1 | 0.9 | 4.6 | 0.9 | 3.1 |
| 0.95 | 1.6 | 0.95 | 2.5 | 0.95 | 1.7 | 0.95 | 3.3 | 0.95 | 2.3 |
| 1 | 1.2 | 1 | 1.2 | 1 | 1.2 | 1 | 1.2 | 1 | 1.2 |

HF-HCFO-1233xf-HCFO-1233zdE-HFO-1234zeZ-HFO-1243zf

| Organics 0.9 F1233xf + 0.033 F1234zeZ + 0.033 F1233zdE + 0.034 F1243zf | | Organics 0.033 F1233xf + 0.9 F1234zeZ + 0.033 F1233zdE + 0.034 F1243zf | | Organics 0.033 F1233xf + 0.033 F1234zeZ + 0.9 F1233zdE + 0.034 F1243zf | | Organics 0.034 F1233xf + 0.033 F1234zeZ + 0.033 F1233zdE + 0.9 F1243zf | | Organics 0.25 F1233xf + 0.25 F1234zeE + 0.25 F1233zdE + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 1.9 | 0 | 1.5 | 0 | 5.5 | 0 | 2.8 |
| 0.05 | 2.8 | 0.05 | 3.0 | 0.05 | 2.6 | 0.05 | 6.4 | 0.05 | 3.9 |
| 0.1 | 2.8 | 0.1 | 3.0 | 0.1 | 2.6 | 0.1 | 6.5 | 0.1 | 3.9 |
| 0.15 | 2.8 | 0.15 | 3.0 | 0.15 | 2.6 | 0.15 | 6.5 | 0.15 | 3.9 |
| 0.2 | 2.8 | 0.2 | 3.0 | 0.2 | 2.6 | 0.2 | 6.5 | 0.2 | 3.9 |
| 0.25 | 2.8 | 0.25 | 3.0 | 0.25 | 2.6 | 0.25 | 6.5 | 0.25 | 3.9 |
| 0.3 | 2.8 | 0.3 | 3.0 | 0.3 | 2.6 | 0.3 | 6.5 | 0.3 | 3.9 |
| 0.35 | 2.8 | 0.35 | 3.0 | 0.35 | 2.6 | 0.35 | 6.5 | 0.35 | 3.9 |
| 0.4 | 2.8 | 0.4 | 3.0 | 0.4 | 2.6 | 0.4 | 6.5 | 0.4 | 3.9 |
| 0.45 | 2.8 | 0.45 | 3.0 | 0.45 | 2.6 | 0.45 | 6.5 | 0.45 | 3.9 |
| 0.5 | 2.8 | 0.5 | 3.0 | 0.5 | 2.6 | 0.5 | 6.5 | 0.5 | 3.9 |
| 0.55 | 2.8 | 0.55 | 3.0 | 0.55 | 2.6 | 0.55 | 6.5 | 0.55 | 3.9 |
| 0.6 | 2.8 | 0.6 | 3.0 | 0.6 | 2.6 | 0.6 | 6.5 | 0.6 | 3.9 |
| 0.65 | 2.8 | 0.65 | 3.0 | 0.65 | 2.6 | 0.65 | 6.4 | 0.65 | 3.8 |
| 0.7 | 2.8 | 0.7 | 3.0 | 0.7 | 2.6 | 0.7 | 6.3 | 0.7 | 3.8 |
| 0.75 | 2.8 | 0.75 | 3.0 | 0.75 | 2.6 | 0.75 | 6.1 | 0.75 | 3.7 |
| 0.8 | 2.7 | 0.8 | 2.9 | 0.8 | 2.5 | 0.8 | 5.8 | 0.8 | 3.6 |
| 0.85 | 2.5 | 0.85 | 2.7 | 0.85 | 2.3 | 0.85 | 5.3 | 0.85 | 3.3 |
| 0.9 | 2.2 | 0.9 | 2.4 | 0.9 | 2.1 | 0.9 | 4.5 | 0.9 | 2.8 |
| 0.95 | 1.8 | 0.95 | 1.9 | 0.95 | 1.7 | 0.95 | 3.2 | 0.95 | 2.2 |
| 1 | 1.2 | 1 | 1.2 | 1 | 1.2 | 1 | 1.2 | 1 | 1.2 |

-continued

| HF-HFC-245cb-HCFO-1233zdE-HFO-1234zeE-HFO-1234zeZ | | | | | | | | | |
|---|---|---|---|---|---|---|---|---|---|
| Organics 0.9 F245cb + 0.033 F1234zeE + 0.033 F1233zdE + 0.034 F1234zeZ | | Organics 0.033 F245cb + 0.9 F1234zeE + 0.033 F1233zdE + 0.034 F1243zeZ | | Organics 0.033 F245cb + 0.033 F1234zeE + 0.9 F1233zdE + 0.034 F1243zeZ | | Organics 0.034 F245cb + 0.033 F1234zeE + 0.033 F1233zdE + 0.9 F1243zeZ | | Organics 0.25 F245cb + 0.25 F1234zeE + 0.25 F1233zdE + 0.25 F1243zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.4 | 0 | 4.7 | 0 | 1.6 | 0 | 2.0 | 0 | 3.2 |
| 0.05 | 5.6 | 0.05 | 5.6 | 0.05 | 2.7 | 0.05 | 3.1 | 0.05 | 4.3 |
| 0.1 | 5.6 | 0.1 | 5.6 | 0.1 | 2.7 | 0.1 | 3.1 | 0.1 | 4.3 |
| 0.15 | 5.6 | 0.15 | 5.6 | 0.15 | 2.7 | 0.15 | 3.1 | 0.15 | 4.3 |
| 0.2 | 5.6 | 0.2 | 5.6 | 0.2 | 2.7 | 0.2 | 3.1 | 0.2 | 4.3 |
| 0.25 | 5.6 | 0.25 | 5.6 | 0.25 | 2.7 | 0.25 | 3.1 | 0.25 | 4.3 |
| 0.3 | 5.6 | 0.3 | 5.6 | 0.3 | 2.7 | 0.3 | 3.1 | 0.3 | 4.3 |
| 0.35 | 5.6 | 0.35 | 5.6 | 0.35 | 2.7 | 0.35 | 3.1 | 0.35 | 4.3 |
| 0.4 | 5.6 | 0.4 | 5.6 | 0.4 | 2.7 | 0.4 | 3.1 | 0.4 | 4.3 |
| 0.45 | 5.6 | 0.45 | 5.6 | 0.45 | 2.7 | 0.45 | 3.1 | 0.45 | 4.3 |
| 0.5 | 5.6 | 0.5 | 5.6 | 0.5 | 2.7 | 0.5 | 3.1 | 0.5 | 4.3 |
| 0.55 | 5.6 | 0.55 | 5.6 | 0.55 | 2.7 | 0.55 | 3.1 | 0.55 | 4.3 |
| 0.6 | 5.6 | 0.6 | 5.5 | 0.6 | 2.7 | 0.6 | 3.1 | 0.6 | 4.3 |
| 0.65 | 5.6 | 0.65 | 5.4 | 0.65 | 2.7 | 0.65 | 3.1 | 0.65 | 4.3 |
| 0.7 | 5.7 | 0.7 | 5.2 | 0.7 | 2.7 | 0.7 | 3.1 | 0.7 | 4.3 |
| 0.75 | 5.7 | 0.75 | 5.0 | 0.75 | 2.7 | 0.75 | 3.1 | 0.75 | 4.3 |
| 0.8 | 5.7 | 0.8 | 4.7 | 0.8 | 2.6 | 0.8 | 3.0 | 0.8 | 4.1 |
| 0.85 | 5.6 | 0.85 | 4.2 | 0.85 | 2.4 | 0.85 | 2.7 | 0.85 | 3.7 |
| 0.9 | 4.8 | 0.9 | 3.5 | 0.9 | 2.1 | 0.9 | 2.4 | 0.9 | 3.2 |
| 0.95 | 3.4 | 0.95 | 2.5 | 0.95 | 1.7 | 0.95 | 1.9 | 0.95 | 2.4 |
| 1 | 1.2 | 1 | 1.2 | 1 | 1.2 | 1 | 1.2 | 1 | 1.2 |

| HF-HCFO-1233xf-HCFO-1233zdE-HFO-1234zeE-HFO-1243zf | | | | | | | | | |
|---|---|---|---|---|---|---|---|---|---|
| Organics 0.9 F1233xf + 0.033 F1234zeZ + 0.033 F1233zdE + 0.034 F1243zf | | Organics 0.033 F1233xf + 0.9 F1234zeZ + 0.033 F1233zdE + 0.034 F1243zf | | Organics 0.033 F1233xf + 0.033 F1234zeZ + 0.9 F1233zdE + 0.034 F1243zf | | Organics 0.034 F1233xf + 0.033 F1234zeZ + 0.033 F1233zdE + 0.9 F1243zf | | Organics 0.25 F1233xf + 0.25 F1234zeZ + 0.25 F1233zdE + 0.25 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 1.9 | 0 | 1.5 | 0 | 5.5 | 0 | 2.8 |
| 0.05 | 2.8 | 0.05 | 3.0 | 0.05 | 2.6 | 0.05 | 6.4 | 0.05 | 3.9 |
| 0.1 | 2.8 | 0.1 | 3.0 | 0.1 | 2.6 | 0.1 | 6.5 | 0.1 | 3.9 |
| 0.15 | 2.8 | 0.15 | 3.0 | 0.15 | 2.6 | 0.15 | 6.5 | 0.15 | 3.9 |
| 0.2 | 2.8 | 0.2 | 3.0 | 0.2 | 2.6 | 0.2 | 6.5 | 0.2 | 3.9 |
| 0.25 | 2.8 | 0.25 | 3.0 | 0.25 | 2.6 | 0.25 | 6.5 | 0.25 | 3.9 |
| 0.3 | 2.8 | 0.3 | 3.0 | 0.3 | 2.6 | 0.3 | 6.5 | 0.3 | 3.9 |
| 0.35 | 2.8 | 0.35 | 3.0 | 0.35 | 2.6 | 0.35 | 6.5 | 0.35 | 3.9 |
| 0.4 | 2.8 | 0.4 | 3.0 | 0.4 | 2.6 | 0.4 | 6.5 | 0.4 | 3.9 |
| 0.45 | 2.8 | 0.45 | 3.0 | 0.45 | 2.6 | 0.45 | 6.4 | 0.45 | 3.9 |
| 0.5 | 2.8 | 0.5 | 3.0 | 0.5 | 2.6 | 0.5 | 6.4 | 0.5 | 3.9 |
| 0.55 | 2.8 | 0.55 | 3.0 | 0.55 | 2.6 | 0.55 | 6.4 | 0.55 | 3.9 |
| 0.6 | 2.8 | 0.6 | 3.0 | 0.6 | 2.6 | 0.6 | 6.4 | 0.6 | 3.9 |
| 0.65 | 2.8 | 0.65 | 3.0 | 0.65 | 2.6 | 0.65 | 6.4 | 0.65 | 3.8 |
| 0.7 | 2.8 | 0.7 | 3.0 | 0.7 | 2.6 | 0.7 | 6.3 | 0.7 | 3.8 |
| 0.75 | 2.8 | 0.75 | 3.0 | 0.75 | 2.6 | 0.75 | 6.1 | 0.75 | 3.7 |
| 0.8 | 2.7 | 0.8 | 2.9 | 0.8 | 2.5 | 0.8 | 5.8 | 0.8 | 3.6 |
| 0.85 | 2.5 | 0.85 | 2.7 | 0.85 | 2.3 | 0.85 | 5.3 | 0.85 | 3.3 |
| 0.9 | 2.2 | 0.9 | 2.4 | 0.9 | 2.1 | 0.9 | 4.5 | 0.9 | 2.8 |
| 0.95 | 1.8 | 0.95 | 1.9 | 0.95 | 1.7 | 0.95 | 3.2 | 0.95 | 2.2 |
| 1 | 1.2 | 1 | 1.2 | 1 | 1.2 | 1 | 1.2 | 1 | 1.2 |

-continued

| HF-HFC-245cb-HCFO-1233zdE-HFO-1234zeE-HFO-1234zeZ | | | | | | | | | |
|---|---|---|---|---|---|---|---|---|---|
| Organics 0.9 F245cb + 0.033 F1234zeE + 0.033 F1233zdE + 0.034 F1234zeZ | | Organics 0.033 F245cb + 0.9 F1234zeE + 0.033 F1233zdE + 0.034 F1234zeZ | | Organics 0.033 F245cb + 0.033 F1234zeE + 0.9 F1233zdE + 0.034 F1234zeZ | | Organics 0.034 F245cb + 0.033 F1234zeE + 0.033 F1233zdE + 0.9 F1234zeZ | | Organics 0.25 F245cb + 0.25 F1234zeE + 0.25 F1233zdE + 0.25 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.4 | 0 | 4.7 | 0 | 1.6 | 0 | 2.0 | 0 | 3.2 |
| 0.05 | 5.6 | 0.05 | 5.6 | 0.05 | 2.7 | 0.05 | 3.1 | 0.05 | 4.3 |
| 0.1 | 5.6 | 0.1 | 5.6 | 0.1 | 2.7 | 0.1 | 3.1 | 0.1 | 4.3 |
| 0.15 | 5.6 | 0.15 | 5.6 | 0.15 | 2.7 | 0.15 | 3.1 | 0.15 | 4.3 |
| 0.2 | 5.6 | 0.2 | 5.6 | 0.2 | 2.7 | 0.2 | 3.1 | 0.2 | 4.3 |
| 0.25 | 5.6 | 0.25 | 5.6 | 0.25 | 2.7 | 0.25 | 3.1 | 0.25 | 4.3 |
| 0.3 | 5.6 | 0.3 | 5.6 | 0.3 | 2.7 | 0.3 | 3.1 | 0.3 | 4.3 |
| 0.35 | 5.6 | 0.35 | 5.6 | 0.35 | 2.7 | 0.35 | 3.1 | 0.35 | 4.3 |
| 0.4 | 5.6 | 0.4 | 5.6 | 0.4 | 2.7 | 0.4 | 3.1 | 0.4 | 4.3 |
| 0.45 | 5.6 | 0.45 | 5.6 | 0.45 | 2.7 | 0.45 | 3.1 | 0.45 | 4.3 |
| 0.5 | 5.6 | 0.5 | 5.6 | 0.5 | 2.7 | 0.5 | 3.1 | 0.5 | 4.3 |
| 0.55 | 5.6 | 0.55 | 5.6 | 0.55 | 2.7 | 0.55 | 3.1 | 0.55 | 4.3 |
| 0.6 | 5.6 | 0.6 | 5.5 | 0.6 | 2.7 | 0.6 | 3.1 | 0.6 | 4.3 |
| 0.65 | 5.6 | 0.65 | 5.4 | 0.65 | 2.7 | 0.65 | 3.1 | 0.65 | 4.3 |
| 0.7 | 5.7 | 0.7 | 5.2 | 0.7 | 2.7 | 0.7 | 3.1 | 0.7 | 4.3 |
| 0.75 | 5.7 | 0.75 | 5.0 | 0.75 | 2.7 | 0.75 | 3.1 | 0.75 | 4.3 |
| 0.8 | 5.7 | 0.8 | 4.7 | 0.8 | 2.6 | 0.8 | 3.0 | 0.8 | 4.1 |
| 0.85 | 5.6 | 0.85 | 4.2 | 0.85 | 2.4 | 0.85 | 2.7 | 0.85 | 3.7 |
| 0.9 | 4.8 | 0.9 | 3.5 | 0.9 | 2.1 | 0.9 | 2.4 | 0.9 | 3.2 |
| 0.95 | 3.4 | 0.95 | 2.5 | 0.95 | 1.7 | 0.95 | 1.9 | 0.95 | 2.4 |
| 1 | 1.2 | 1 | 1.2 | 1 | 1.2 | 1 | 1.2 | 1 | 1.2 |

| HF-HFC-245cb-HCFO-1233zdE-HFO-1234zeE-HFO-1243zf | | | | | | | | | |
|---|---|---|---|---|---|---|---|---|---|
| Organics 0.9 F245cb + 0.033 F1234zeE + 0.033 F1233zdE + 0.034 F1243zf | | Organics 0.033 F245cb + 0.9 F1234zeE + 0.033 F1233zdE + 0.034 F1243zf | | Organics 0.033 F245cb + 0.033 F1234zeE + 0.9 F1233zdE + 0.034 F1243zf | | Organics 0.034 F245cb + 0.033 F1234zeE + 0.033 F1233zdE + 0.9 F1243zf | | Organics 0.25 F245cb + 0.25 F1234zeE + 0.25 F1233zdE + 0.25 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.6 | 0 | 4.8 | 0 | 1.8 | 0 | 5.7 | 0 | 4.3 |
| 0.05 | 5.8 | 0.05 | 5.8 | 0.05 | 2.9 | 0.05 | 6.6 | 0.05 | 5.4 |
| 0.1 | 5.8 | 0.1 | 5.8 | 0.1 | 2.9 | 0.1 | 6.6 | 0.1 | 5.4 |
| 0.15 | 5.8 | 0.15 | 5.8 | 0.15 | 2.9 | 0.15 | 6.6 | 0.15 | 5.4 |
| 0.2 | 5.8 | 0.2 | 5.8 | 0.2 | 2.9 | 0.2 | 6.6 | 0.2 | 5.4 |
| 0.25 | 5.8 | 0.25 | 5.8 | 0.25 | 2.9 | 0.25 | 6.6 | 0.25 | 5.4 |
| 0.3 | 5.8 | 0.3 | 5.8 | 0.3 | 2.9 | 0.3 | 6.6 | 0.3 | 5.4 |
| 0.35 | 5.8 | 0.35 | 5.8 | 0.35 | 2.9 | 0.35 | 6.6 | 0.35 | 5.4 |
| 0.4 | 5.8 | 0.4 | 5.8 | 0.4 | 2.9 | 0.4 | 6.6 | 0.4 | 5.4 |
| 0.45 | 5.8 | 0.45 | 5.8 | 0.45 | 2.9 | 0.45 | 6.6 | 0.45 | 5.4 |
| 0.5 | 5.8 | 0.5 | 5.7 | 0.5 | 2.9 | 0.5 | 6.6 | 0.5 | 5.4 |
| 0.55 | 5.8 | 0.55 | 5.7 | 0.55 | 2.9 | 0.55 | 6.6 | 0.55 | 5.4 |
| 0.6 | 5.8 | 0.6 | 5.6 | 0.6 | 2.9 | 0.6 | 6.6 | 0.6 | 5.4 |
| 0.65 | 5.8 | 0.65 | 5.5 | 0.65 | 2.8 | 0.65 | 6.5 | 0.65 | 5.4 |
| 0.7 | 5.8 | 0.7 | 5.4 | 0.7 | 2.8 | 0.7 | 6.4 | 0.7 | 5.4 |
| 0.75 | 5.8 | 0.75 | 5.2 | 0.75 | 2.8 | 0.75 | 6.3 | 0.75 | 5.2 |
| 0.8 | 5.8 | 0.8 | 4.6 | 0.8 | 2.7 | 0.8 | 6.0 | 0.8 | 5.0 |
| 0.85 | 5.7 | 0.85 | 4.3 | 0.85 | 2.5 | 0.85 | 5.5 | 0.85 | 4.5 |
| 0.9 | 4.9 | 0.9 | 3.6 | 0.9 | 2.2 | 0.9 | 4.7 | 0.9 | 3.9 |
| 0.95 | 3.5 | 0.95 | 2.6 | 0.95 | 1.8 | 0.95 | 3.3 | 0.95 | 2.8 |
| 1 | 1.2 | 1 | 1.2 | 1 | 1.2 | 1 | 1.2 | 1 | 1.2 |

-continued

| HF-HFC-245cb-HCFO-1233zdE-HFO-1234zeZ-HFO-1243zf | | | | | | | | | |
|---|---|---|---|---|---|---|---|---|---|
| Organics 0.9 F245cb + 0.033 F1234zeZ + 0.033 F1233zdE + 0.034 F1243zf | | Organics 0.033 F245cb + 0.9 F1234zeZ + 0.033 F1233zdE + 0.034 F1243zf | | Organics 0.033 F245cb + 0.033 F1234zeZ + 0.9 F1233zdE + 0.034 F1243zf | | Organics 0.034 F245cb + 0.033 F1234zeZ + 0.033 F1233zdE + 0.9 F1243zf | | Organics 0.25 F245cb + 0.25 F1234zeZ + 0.25 F1233zdE + 0.25 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.5 | 0 | 2.0 | 0 | 1.7 | 0 | 5.6 | 0 | 3.5 |
| 0.05 | 5.7 | 0.05 | 3.2 | 0.05 | 2.8 | 0.05 | 6.5 | 0.05 | 4.6 |
| 0.1 | 5.7 | 0.1 | 3.2 | 0.1 | 2.8 | 0.1 | 6.5 | 0.1 | 4.6 |
| 0.15 | 5.7 | 0.15 | 3.2 | 0.15 | 2.8 | 0.15 | 6.5 | 0.15 | 4.6 |
| 0.2 | 5.7 | 0.2 | 3.2 | 0.2 | 2.8 | 0.2 | 6.5 | 0.2 | 4.6 |
| 0.25 | 5.7 | 0.25 | 3.2 | 0.25 | 2.8 | 0.25 | 6.5 | 0.25 | 4.6 |
| 0.3 | 5.7 | 0.3 | 3.2 | 0.3 | 2.8 | 0.3 | 6.5 | 0.3 | 4.6 |
| 0.35 | 5.7 | 0.35 | 3.2 | 0.35 | 2.8 | 0.35 | 6.5 | 0.35 | 4.6 |
| 0.4 | 5.7 | 0.4 | 3.2 | 0.4 | 2.8 | 0.4 | 6.5 | 0.4 | 4.6 |
| 0.45 | 5.7 | 0.45 | 3.2 | 0.45 | 2.8 | 0.45 | 6.5 | 0.45 | 4.6 |
| 0.5 | 5.7 | 0.5 | 3.2 | 0.5 | 2.8 | 0.5 | 6.5 | 0.5 | 4.7 |
| 0.55 | 5.7 | 0.55 | 3.2 | 0.55 | 2.8 | 0.55 | 6.5 | 0.55 | 4.7 |
| 0.6 | 5.7 | 0.6 | 3.2 | 0.6 | 2.8 | 0.6 | 6.5 | 0.6 | 4.7 |
| 0.65 | 5.7 | 0.65 | 3.2 | 0.65 | 2.8 | 0.65 | 6.4 | 0.65 | 4.7 |
| 0.7 | 5.7 | 0.7 | 3.2 | 0.7 | 2.8 | 0.7 | 6.4 | 0.7 | 4.7 |
| 0.75 | 5.7 | 0.75 | 3.1 | 0.75 | 2.8 | 0.75 | 6.2 | 0.75 | 4.7 |
| 0.8 | 5.7 | 0.8 | 3.0 | 0.8 | 2.6 | 0.8 | 5.9 | 0.8 | 4.5 |
| 0.85 | 5.6 | 0.85 | 2.8 | 0.85 | 2.4 | 0.85 | 5.4 | 0.85 | 4.1 |
| 0.9 | 4.8 | 0.9 | 2.5 | 0.9 | 2.2 | 0.9 | 4.6 | 0.9 | 3.5 |
| 0.95 | 3.4 | 0.95 | 1.9 | 0.95 | 1.8 | 0.95 | 3.3 | 0.95 | 2.6 |
| 1 | 1.2 | 1 | 1.2 | 1 | 1.2 | 1 | 1.2 | 1 | 1.2 |

| HF-HCFO-1233zdE-HFO-1234zeE-HFO-1234zeZ-HFO-1243zf | | | | | | | | | |
|---|---|---|---|---|---|---|---|---|---|
| Organics 0.9 F1234zeE + 0.033 F1234zeZ + 0.033 F1233zdE + 0.034 F1243zf | | Organics 0.033 F1234zeE + 0.9 F1234zeZ + 0.033 F1233zdE + 0.034 F1243zf | | Organics 0.033 F1234zeE + 0.033 F1234zeZ + 0.9 F1233zdE + 0.034 F1243zf | | Organics 0.034 F1234zeE + 0.033 F1234zeZ + 0.033 F1233zdE + 0.9 F1243zf | | Organics 0.25 F1234zeE + 0.25 F1234zeZ + 0.25 F1233zdE + 0.25 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.7 | 0 | 2.1 | 0 | 1.7 | 0 | 5.6 | 0 | 3.6 |
| 0.05 | 5.7 | 0.05 | 3.2 | 0.05 | 2.8 | 0.05 | 6.5 | 0.05 | 4.7 |
| 0.1 | 5.7 | 0.1 | 3.2 | 0.1 | 2.8 | 0.1 | 6.6 | 0.1 | 4.7 |
| 0.15 | 5.7 | 0.15 | 3.2 | 0.15 | 2.8 | 0.15 | 6.5 | 0.15 | 4.7 |
| 0.2 | 5.7 | 0.2 | 3.2 | 0.2 | 2.8 | 0.2 | 6.5 | 0.2 | 4.7 |
| 0.25 | 5.7 | 0.25 | 3.2 | 0.25 | 2.8 | 0.25 | 6.5 | 0.25 | 4.7 |
| 0.3 | 5.7 | 0.3 | 3.2 | 0.3 | 2.8 | 0.3 | 6.5 | 0.3 | 4.6 |
| 0.35 | 5.7 | 0.35 | 3.1 | 0.35 | 2.8 | 0.35 | 6.5 | 0.35 | 4.6 |
| 0.4 | 5.7 | 0.4 | 3.1 | 0.4 | 2.8 | 0.4 | 6.5 | 0.4 | 4.6 |
| 0.45 | 5.7 | 0.45 | 3.1 | 0.45 | 2.7 | 0.45 | 6.5 | 0.45 | 4.6 |
| 0.5 | 5.6 | 0.5 | 3.1 | 0.5 | 2.7 | 0.5 | 6.5 | 0.5 | 4.6 |
| 0.55 | 5.6 | 0.55 | 3.1 | 0.55 | 2.7 | 0.55 | 6.5 | 0.55 | 4.6 |
| 0.6 | 5.5 | 0.6 | 3.1 | 0.6 | 2.7 | 0.6 | 6.5 | 0.6 | 4.6 |
| 0.65 | 5.4 | 0.65 | 3.1 | 0.65 | 2.7 | 0.65 | 6.4 | 0.65 | 4.6 |
| 0.7 | 5.3 | 0.7 | 3.1 | 0.7 | 2.7 | 0.7 | 6.3 | 0.7 | 4.5 |
| 0.75 | 5.0 | 0.75 | 3.1 | 0.75 | 2.7 | 0.75 | 6.2 | 0.75 | 4.3 |
| 0.8 | 4.7 | 0.8 | 3.0 | 0.8 | 2.6 | 0.8 | 5.9 | 0.8 | 4.1 |
| 0.85 | 4.2 | 0.85 | 2.7 | 0.85 | 2.4 | 0.85 | 5.4 | 0.85 | 3.7 |
| 0.9 | 3.5 | 0.9 | 2.4 | 0.9 | 2.1 | 0.9 | 4.6 | 0.9 | 3.2 |
| 0.95 | 2.5 | 0.95 | 1.9 | 0.95 | 1.7 | 0.95 | 3.3 | 0.95 | 2.4 |
| 1 | 1.2 | 1 | 1.2 | 1 | 1.2 | 1 | 1.2 | 1 | 1.2 |

-continued

| HF-HCFO-1233xf-HFO-1234yf-HFO-1234zeZ-HCFO-1233zdE | | | | | | | | | |
|---|---|---|---|---|---|---|---|---|---|
| Organics 0.9 F1233xf + 0.033 F1234zeE + 0.033 F1233zdE + 0.034 F1234yf | | Organics 0.033 F1233xf + 0.9 F1234zeE + 0.033 F1233zdE + 0.034 F1234yf | | Organics 0.033 F1233xf + 0.033 F1234zeE + 0.9 F1233zdE + 0.034 F1234yf | | Organics 0.034 F1233xf + 0.033 F1234zeE + 0.033 F1233zdE + 0.9 F1234yf | | Organics 0.25 F1233xf + 0.25 F1234zeE + 0.25 F1233zdE + 0.25 F1234yf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 4.7 | 0 | 1.7 | 0 | 6.4 | 0 | 3.8 |
| 0.05 | 3.0 | 0.05 | 5.7 | 0.05 | 2.8 | 0.05 | 2.8 | 0.05 | 4.8 |
| 0.1 | 3.0 | 0.1 | 5.7 | 0.1 | 2.8 | 0.1 | 2.8 | 0.1 | 4.8 |
| 0.15 | 3.0 | 0.15 | 5.7 | 0.15 | 2.8 | 0.15 | 2.8 | 0.15 | 4.8 |
| 0.2 | 3.0 | 0.2 | 5.7 | 0.2 | 2.8 | 0.2 | 2.8 | 0.2 | 4.8 |
| 0.25 | 3.0 | 0.25 | 5.7 | 0.25 | 2.8 | 0.25 | 2.8 | 0.25 | 4.8 |
| 0.3 | 3.0 | 0.3 | 5.7 | 0.3 | 2.8 | 0.3 | 2.8 | 0.3 | 4.8 |
| 0.35 | 3.0 | 0.35 | 5.7 | 0.35 | 2.8 | 0.35 | 2.8 | 0.35 | 4.8 |
| 0.4 | 3.0 | 0.4 | 5.7 | 0.4 | 2.8 | 0.4 | 2.8 | 0.4 | 4.8 |
| 0.45 | 3.0 | 0.45 | 5.7 | 0.45 | 2.8 | 0.45 | 2.8 | 0.45 | 4.8 |
| 0.5 | 3.0 | 0.5 | 5.7 | 0.5 | 2.8 | 0.5 | 2.8 | 0.5 | 4.8 |
| 0.55 | 3.0 | 0.55 | 5.6 | 0.55 | 2.8 | 0.55 | 2.8 | 0.55 | 4.8 |
| 0.6 | 3.0 | 0.6 | 5.5 | 0.6 | 2.8 | 0.6 | 2.8 | 0.6 | 4.8 |
| 0.65 | 2.9 | 0.65 | 5.4 | 0.65 | 2.7 | 0.65 | 2.8 | 0.65 | 4.8 |
| 0.7 | 2.9 | 0.7 | 5.3 | 0.7 | 2.7 | 0.7 | 2.8 | 0.7 | 4.7 |
| 0.75 | 2.9 | 0.75 | 5.1 | 0.75 | 2.7 | 0.75 | 7.2 | 0.75 | 4.6 |
| 0.8 | 2.6 | 0.8 | 4.7 | 0.8 | 2.6 | 0.8 | 6.9 | 0.8 | 4.3 |
| 0.85 | 2.6 | 0.85 | 4.2 | 0.85 | 2.4 | 0.85 | 6.3 | 0.85 | 3.9 |
| 0.9 | 2.3 | 0.9 | 3.6 | 0.9 | 2.1 | 0.9 | 5.3 | 0.9 | 3.3 |
| 0.95 | 1.8 | 0.95 | 2.6 | 0.95 | 1.7 | 0.95 | 3.7 | 0.95 | 2.4 |
| 1 | 1.2 | 1 | 1.2 | 1 | 1.2 | 1 | 1.2 | 1 | 1.2 |

| HF-HCFO-1233xf-HFO-1234yf-HFO-1234zeZ-HCFO-1233zdE | | | | | | | | | |
|---|---|---|---|---|---|---|---|---|---|
| Organics 0.9 F1233xf + 0.033 F1234zeE + 0.033 F1233zdE + 0.034 F1234yf | | Organics 0.033 F1233xf + 0.9 F1234zeE + 0.033 F1233zdE + 0.034 F1234yf | | Organics 0.033 F1233xf + 0.033 F1234zeE + 0.9 F1233zdE + 0.034 F1234yf | | Organics 0.034 F1233xf + 0.033 F1234zeE + 0.033 F1233zdE + 0.9 F1234yf | | Organics 0.25 F1233xf + 0.25 F1234zeE + 0.25 F1233zdE + 0.25 F1234yf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 2.0 | 0 | 1.6 | 0 | 6.3 | 0 | 3.0 |
| 0.05 | 2.9 | 0.05 | 3.1 | 0.05 | 2.7 | 0.05 | 7.3 | 0.05 | 4.1 |
| 0.1 | 2.9 | 0.1 | 3.1 | 0.1 | 2.7 | 0.1 | 7.3 | 0.1 | 4.1 |
| 0.15 | 2.9 | 0.15 | 3.1 | 0.15 | 2.7 | 0.15 | 7.3 | 0.15 | 4.1 |
| 0.2 | 2.9 | 0.2 | 3.1 | 0.2 | 2.7 | 0.2 | 7.3 | 0.2 | 4.1 |
| 0.25 | 2.9 | 0.25 | 3.1 | 0.25 | 2.7 | 0.25 | 7.3 | 0.25 | 4.1 |
| 0.3 | 2.9 | 0.3 | 3.1 | 0.3 | 2.7 | 0.3 | 7.3 | 0.3 | 4.1 |
| 0.35 | 2.9 | 0.35 | 3.1 | 0.35 | 2.7 | 0.35 | 7.3 | 0.35 | 4.1 |
| 0.4 | 2.9 | 0.4 | 3.1 | 0.4 | 2.7 | 0.4 | 7.3 | 0.4 | 4.1 |
| 0.45 | 2.9 | 0.45 | 3.1 | 0.45 | 2.7 | 0.45 | 7.3 | 0.45 | 4.1 |
| 0.5 | 2.9 | 0.5 | 3.1 | 0.5 | 2.7 | 0.5 | 7.3 | 0.5 | 4.1 |
| 0.55 | 2.9 | 0.55 | 3.1 | 0.55 | 2.7 | 0.55 | 7.3 | 0.55 | 4.1 |
| 0.6 | 2.9 | 0.6 | 3.1 | 0.6 | 2.7 | 0.6 | 7.3 | 0.6 | 4.1 |
| 0.65 | 2.9 | 0.65 | 3.1 | 0.65 | 2.7 | 0.65 | 7.3 | 0.65 | 4.1 |
| 0.7 | 2.9 | 0.7 | 3.1 | 0.7 | 2.7 | 0.7 | 7.3 | 0.7 | 4.0 |
| 0.75 | 2.8 | 0.75 | 3.1 | 0.75 | 2.6 | 0.75 | 7.1 | 0.75 | 4.0 |
| 0.8 | 2.7 | 0.8 | 2.9 | 0.8 | 2.5 | 0.8 | 6.8 | 0.8 | 3.8 |
| 0.85 | 2.5 | 0.85 | 2.7 | 0.85 | 2.4 | 0.85 | 6.2 | 0.85 | 3.5 |
| 0.9 | 2.2 | 0.9 | 2.4 | 0.9 | 2.1 | 0.9 | 5.3 | 0.9 | 3.0 |
| 0.95 | 1.6 | 0.95 | 1.9 | 0.95 | 1.7 | 0.95 | 3.7 | 0.95 | 2.3 |
| 1 | 1.2 | 1 | 1.2 | 1 | 1.2 | 1 | 1.2 | 1 | 1.2 |

-continued

| HF-HCFO-1233xf-HFO-1234yf-HCFO-1233zdE-HFO-1243zf | | | | | | | | | |
|---|---|---|---|---|---|---|---|---|---|
| Organics 0.9 F1233xf + 0.033 F1243zf + 0.033 F1233zdE + 0.034 F1234yf | | Organics 0.033 F1233xf + 0.9 F1243zf + 0.033 F1233zdE + 0.034 F1234yf | | Organics 0.033 F1233xf + 0.033 F1243zf + 0.9 F1233zdE + 0.034 F1234yf | | Organics 0.034 F1233xf + 0.033 F1243zf + 0.033 F1233zdE + 0.9 F1234yf | | Organics 0.25 F1233xf + 0.25 F1243zf + 0.25 F1233zdE + 0.25 F1234yf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 5.6 | 0 | 1.7 | 0 | 6.4 | 0 | 4.1 |
| 0.05 | 3.0 | 0.05 | 6.6 | 0.05 | 2.8 | 0.05 | 7.4 | 0.05 | 5.2 |
| 0.1 | 3.0 | 0.1 | 6.6 | 0.1 | 2.8 | 0.1 | 7.4 | 0.1 | 5.2 |
| 0.15 | 3.0 | 0.15 | 6.6 | 0.15 | 2.8 | 0.15 | 7.4 | 0.15 | 5.2 |
| 0.2 | 3.0 | 0.2 | 6.6 | 0.2 | 2.8 | 0.2 | 7.4 | 0.2 | 5.2 |
| 0.25 | 3.0 | 0.25 | 6.6 | 0.25 | 2.8 | 0.25 | 7.4 | 0.25 | 5.2 |
| 0.3 | 3.0 | 0.3 | 6.6 | 0.3 | 2.8 | 0.3 | 7.4 | 0.3 | 5.2 |
| 0.35 | 3.0 | 0.35 | 6.6 | 0.35 | 2.8 | 0.35 | 7.4 | 0.35 | 5.2 |
| 0.4 | 3.0 | 0.4 | 6.6 | 0.4 | 2.8 | 0.4 | 7.4 | 0.4 | 5.2 |
| 0.45 | 3.0 | 0.45 | 6.6 | 0.45 | 2.8 | 0.45 | 7.4 | 0.45 | 5.2 |
| 0.5 | 3.0 | 0.5 | 6.6 | 0.5 | 2.8 | 0.5 | 7.4 | 0.5 | 5.1 |
| 0.55 | 3.0 | 0.55 | 6.6 | 0.55 | 2.8 | 0.55 | 7.4 | 0.55 | 5.1 |
| 0.6 | 3.0 | 0.6 | 6.5 | 0.6 | 2.8 | 0.6 | 7.4 | 0.6 | 5.1 |
| 0.65 | 3.0 | 0.65 | 6.5 | 0.65 | 2.8 | 0.65 | 7.4 | 0.65 | 5.1 |
| 0.7 | 3.0 | 0.7 | 6.4 | 0.7 | 2.8 | 0.7 | 7.4 | 0.7 | 5.1 |
| 0.75 | 3.0 | 0.75 | 6.2 | 0.75 | 2.8 | 0.75 | 7.2 | 0.75 | 4.9 |
| 0.8 | 2.8 | 0.8 | 6.0 | 0.8 | 2.7 | 0.8 | 6.9 | 0.8 | 4.7 |
| 0.85 | 2.6 | 0.85 | 5.5 | 0.85 | 2.5 | 0.85 | 6.3 | 0.85 | 4.3 |
| 0.9 | 2.3 | 0.9 | 4.6 | 0.9 | 2.2 | 0.9 | 5.3 | 0.9 | 3.7 |
| 0.95 | 1.8 | 0.95 | 3.3 | 0.95 | 1.8 | 0.95 | 3.7 | 0.95 | 2.7 |
| 1 | 1.2 | 1 | 1.2 | 1 | 1.2 | 1 | 1.2 | 1 | 1.2 |

| HF-HFO-1234yf-HFO-1234zeE-HFO-1234zeZ-HCFO-1233zdE | | | | | | | | | |
|---|---|---|---|---|---|---|---|---|---|
| Organics 0.9 F1234yf + 0.033 F1233zdE + 0.033 F1234zeE + 0.034 F1234zeZ | | Organics 0.033 F1234yf + 0.9 F1233zdE + 0.033 F1234zeE + 0.034 F1234zeZ | | Organics 0.033 F1234yf + 0.033 F1233zdE + 0.9 F1234zeE + 0.034 F1234zeZ | | Organics 0.034 F1234yf + 0.033 F1233zdE + 0.033 F1234zeE + 0.9 F1234zeZ | | Organics 0.25 F1234yf + 0.25 F1233zf + 0.25 F1234zeE + 0.25 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 1.7 | 0 | 4.7 | 0 | 2.1 | 0 | 3.6 |
| 0.05 | 7.4 | 0.05 | 2.8 | 0.05 | 5.7 | 0.05 | 3.2 | 0.05 | 4.8 |
| 0.1 | 7.4 | 0.1 | 2.8 | 0.1 | 5.7 | 0.1 | 3.2 | 0.1 | 4.8 |
| 0.15 | 7.4 | 0.15 | 2.8 | 0.15 | 5.7 | 0.15 | 3.2 | 0.15 | 4.8 |
| 0.2 | 7.4 | 0.2 | 2.8 | 0.2 | 5.7 | 0.2 | 3.2 | 0.2 | 4.8 |
| 0.25 | 7.4 | 0.25 | 2.8 | 0.25 | 5.7 | 0.25 | 3.2 | 0.25 | 4.8 |
| 0.3 | 7.4 | 0.3 | 2.8 | 0.3 | 5.7 | 0.3 | 3.2 | 0.3 | 4.8 |
| 0.35 | 7.4 | 0.35 | 2.8 | 0.35 | 5.7 | 0.35 | 3.2 | 0.35 | 4.8 |
| 0.4 | 7.4 | 0.4 | 2.8 | 0.4 | 5.7 | 0.4 | 3.2 | 0.4 | 4.8 |
| 0.45 | 7.4 | 0.45 | 2.8 | 0.45 | 5.7 | 0.45 | 3.2 | 0.45 | 4.8 |
| 0.5 | 7.4 | 0.5 | 2.8 | 0.5 | 5.7 | 0.5 | 3.2 | 0.5 | 4.8 |
| 0.55 | 7.4 | 0.55 | 2.8 | 0.55 | 5.6 | 0.55 | 3.2 | 0.55 | 4.8 |
| 0.6 | 7.4 | 0.6 | 2.8 | 0.6 | 5.5 | 0.6 | 3.2 | 0.6 | 4.8 |
| 0.65 | 7.4 | 0.65 | 2.7 | 0.65 | 5.4 | 0.65 | 3.2 | 0.65 | 4.8 |
| 0.7 | 7.4 | 0.7 | 2.7 | 0.7 | 5.3 | 0.7 | 3.2 | 0.7 | 4.7 |
| 0.75 | 7.2 | 0.75 | 2.7 | 0.75 | 5.1 | 0.75 | 3.1 | 0.75 | 4.6 |
| 0.8 | 6.9 | 0.8 | 2.6 | 0.8 | 4.7 | 0.8 | 3.0 | 0.8 | 4.3 |
| 0.85 | 6.3 | 0.85 | 2.4 | 0.85 | 4.2 | 0.85 | 2.8 | 0.85 | 4.0 |
| 0.9 | 5.3 | 0.9 | 2.1 | 0.9 | 3.6 | 0.9 | 2.4 | 0.9 | 3.4 |
| 0.95 | 3.7 | 0.95 | 1.7 | 0.95 | 2.6 | 0.95 | 1.9 | 0.95 | 2.5 |
| 1 | 1.2 | 1 | 1.2 | 1 | 1.2 | 1 | 1.2 | 1 | 1.2 |

-continued

HF-HFO-1234yf-HFO-1234zeE-HCFO-1233zdE-HFO-1243zf

| Organics 0.9 F1234yf + 0.033 F1233zdE + 0.033 F1234zeE + 0.034 F1243zf | | Organics 0.033 F1234yf + 0.9 F1233zdE + 0.033 F1234zeE + 0.034 F1234zf | | Organics 0.033 F1234yf + 0.033 F1233zdE + 0.9 F1234zeE + 0.034 F1234zf | | Organics 0.034 F1234yf + 0.033 F1233zdE + 0.033 F1234zeE + 0.9 F1234zf | | Organics 0.25 F1234yf + 0.25 F1233zdE + 0.25 F1234zeE + 0.25 F1234zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 1.9 | 0 | 4.9 | 0 | 5.7 | 0 | 4.8 |
| 0.05 | 7.5 | 0.05 | 3.0 | 0.05 | 5.8 | 0.05 | 6.7 | 0.05 | 5.8 |
| 0.1 | 7.5 | 0.1 | 3.0 | 0.1 | 5.9 | 0.1 | 6.7 | 0.1 | 5.9 |
| 0.15 | 7.5 | 0.15 | 3.0 | 0.15 | 5.8 | 0.15 | 6.7 | 0.15 | 5.9 |
| 0.2 | 7.5 | 0.2 | 3.0 | 0.2 | 5.8 | 0.2 | 6.7 | 0.2 | 5.9 |
| 0.25 | 7.5 | 0.25 | 3.0 | 0.25 | 5.8 | 0.25 | 6.7 | 0.25 | 5.9 |
| 0.3 | 7.5 | 0.3 | 3.0 | 0.3 | 5.8 | 0.3 | 6.7 | 0.3 | 5.9 |
| 0.35 | 7.5 | 0.35 | 2.9 | 0.35 | 5.8 | 0.35 | 6.7 | 0.35 | 5.9 |
| 0.4 | 7.5 | 0.4 | 2.9 | 0.4 | 5.8 | 0.4 | 6.7 | 0.4 | 5.9 |
| 0.45 | 7.5 | 0.45 | 2.9 | 0.45 | 5.8 | 0.45 | 6.7 | 0.45 | 5.9 |
| 0.5 | 7.5 | 0.5 | 2.9 | 0.5 | 5.8 | 0.5 | 6.7 | 0.5 | 5.8 |
| 0.55 | 7.5 | 0.55 | 2.9 | 0.55 | 5.8 | 0.55 | 6.6 | 0.55 | 5.8 |
| 0.6 | 7.5 | 0.6 | 2.9 | 0.6 | 5.7 | 0.6 | 6.6 | 0.6 | 5.8 |
| 0.65 | 7.5 | 0.65 | 2.9 | 0.65 | 5.6 | 0.65 | 6.6 | 0.65 | 5.8 |
| 0.7 | 7.5 | 0.7 | 2.9 | 0.7 | 5.4 | 0.7 | 6.5 | 0.7 | 5.7 |
| 0.75 | 7.3 | 0.75 | 2.9 | 0.75 | 5.2 | 0.75 | 6.3 | 0.75 | 5.5 |
| 0.8 | 7.0 | 0.8 | 2.7 | 0.8 | 4.9 | 0.8 | 6.0 | 0.8 | 5.2 |
| 0.85 | 6.4 | 0.85 | 2.5 | 0.85 | 4.4 | 0.85 | 5.5 | 0.85 | 4.8 |
| 0.9 | 5.4 | 0.9 | 2.2 | 0.9 | 3.6 | 0.9 | 4.7 | 0.9 | 4.0 |
| 0.95 | 3.7 | 0.95 | 1.8 | 0.95 | 2.6 | 0.95 | 3.3 | 0.95 | 2.9 |
| 1 | 1.2 | 1 | 1.2 | 1 | 1.2 | 1 | 1.2 | 1 | 1.2 |

HF-HFO-1234yf-HFO-1234zeZ-HCFO-1233zdE-HFO-1243zf

| Organics 0.9 F1234yf + 0.033 F1233zdE + 0.033 F1234zeZ+ 0.034 F1243zf | | Organics 0.033 F1234yf + 0.9 F1233zdE + 0.033 F1234zeZ + 0.034 F1234zf | | Organics 0.033 F1234yf + 0.033 F1233zdE + 0.9 F1234zeZ + 0.034 F1234zf | | Organics 0.034 F1234yf + 0.033 F1233zdE + 0.033 F1234zeZ + 0.9 F1234zeZ | | Organics 0.25 F1234yf + 0.25 F1233zdE + 0.25 F1234zeZ + 0.25 F1234zeZ | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 1.7 | 0 | 2.1 | 0 | 5.6 | 0 | 4.1 |
| 0.05 | 7.4 | 0.05 | 2.9 | 0.05 | 3.2 | 0.05 | 6.6 | 0.05 | 5.2 |
| 0.1 | 7.4 | 0.1 | 2.9 | 0.1 | 3.2 | 0.1 | 6.6 | 0.1 | 5.2 |
| 0.15 | 7.4 | 0.15 | 2.9 | 0.15 | 3.2 | 0.15 | 6.6 | 0.15 | 5.2 |
| 0.2 | 7.4 | 0.2 | 2.9 | 0.2 | 3.2 | 0.2 | 6.6 | 0.2 | 5.2 |
| 0.25 | 7.4 | 0.25 | 2.8 | 0.25 | 3.2 | 0.25 | 6.6 | 0.25 | 5.2 |
| 0.3 | 7.4 | 0.3 | 2.8 | 0.3 | 3.2 | 0.3 | 6.6 | 0.3 | 5.2 |
| 0.35 | 7.4 | 0.35 | 2.8 | 0.35 | 3.2 | 0.35 | 6.6 | 0.35 | 5.1 |
| 0.4 | 7.4 | 0.4 | 2.8 | 0.4 | 3.2 | 0.4 | 6.6 | 0.4 | 5.1 |
| 0.45 | 7.4 | 0.45 | 2.8 | 0.45 | 3.2 | 0.45 | 6.6 | 0.45 | 5.1 |
| 0.5 | 7.4 | 0.5 | 2.8 | 0.5 | 3.2 | 0.5 | 6.6 | 0.5 | 5.1 |
| 0.55 | 7.4 | 0.55 | 2.8 | 0.55 | 3.2 | 0.55 | 6.6 | 0.55 | 5.1 |
| 0.6 | 7.4 | 0.6 | 2.8 | 0.6 | 3.2 | 0.6 | 6.5 | 0.6 | 5.1 |
| 0.65 | 7.4 | 0.65 | 2.8 | 0.65 | 3.2 | 0.65 | 6.5 | 0.65 | 5.1 |
| 0.7 | 7.4 | 0.7 | 2.8 | 0.7 | 3.2 | 0.7 | 6.4 | 0.7 | 5.1 |
| 0.75 | 7.2 | 0.75 | 2.8 | 0.75 | 3.2 | 0.75 | 6.2 | 0.75 | 5.0 |
| 0.8 | 6.9 | 0.8 | 2.7 | 0.8 | 3.0 | 0.8 | 5.9 | 0.8 | 4.7 |
| 0.85 | 6.3 | 0.85 | 2.5 | 0.85 | 2.8 | 0.85 | 5.5 | 0.85 | 4.3 |
| 0.9 | 5.3 | 0.9 | 2.2 | 0.9 | 2.5 | 0.9 | 4.6 | 0.9 | 3.7 |
| 0.95 | 3.7 | 0.95 | 1.8 | 0.95 | 2.0 | 0.95 | 3.3 | 0.95 | 2.7 |
| 1 | 1.2 | 1 | 1.2 | 1 | 1.2 | 1 | 1.2 | 1 | 1.2 |

-continued

| HF-HFO-1234yf-HFC-245cb-HFO-1234zeE-HCFO-1233zdE | | | | | | | | | |
|---|---|---|---|---|---|---|---|---|---|
| Organics 0.9 F1234yf + 0.033 F1234zeE + 0.033 F245cb + 0.034 F1233zdE | | Organics 0.033 F1234yf + 0.9 F1234zeE + 0.033 F245cb + 0.034 F1233zdE | | Organics 0.033 F1234yf + 0.033 F1234zeE + 0.9 F245cb + 0.034 F1233zdE | | Organics 0.034 F1234yf + 0.033 F1234zeE + 0.033 F245cb + 0.9 F1233zdE | | Organics 0.25 F1234yf + 0.25 F1234zeE + 0.25 F245cb + 0.25 F1233zdE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 4.8 | 0 | 4.6 | 0 | 1.8 | 0 | 4.5 |
| 0.05 | 7.5 | 0.05 | 5.8 | 0.05 | 5.8 | 0.05 | 2.9 | 0.05 | 5.6 |
| 0.1 | 7.5 | 0.1 | 5.8 | 0.1 | 5.8 | 0.1 | 2.9 | 0.1 | 5.6 |
| 0.15 | 7.5 | 0.15 | 5.8 | 0.15 | 5.8 | 0.15 | 2.9 | 0.15 | 5.6 |
| 0.2 | 7.5 | 0.2 | 5.8 | 0.2 | 5.8 | 0.2 | 2.9 | 0.2 | 5.6 |
| 0.25 | 7.5 | 0.25 | 5.8 | 0.25 | 5.8 | 0.25 | 2.9 | 0.25 | 5.6 |
| 0.3 | 7.5 | 0.3 | 5.8 | 0.3 | 5.8 | 0.3 | 2.9 | 0.3 | 5.6 |
| 0.35 | 7.5 | 0.35 | 5.8 | 0.35 | 5.8 | 0.35 | 2.9 | 0.35 | 5.6 |
| 0.4 | 7.5 | 0.4 | 5.8 | 0.4 | 5.8 | 0.4 | 2.9 | 0.4 | 5.6 |
| 0.45 | 7.5 | 0.45 | 5.8 | 0.45 | 5.8 | 0.45 | 2.9 | 0.45 | 5.6 |
| 0.5 | 7.5 | 0.5 | 5.8 | 0.5 | 5.8 | 0.5 | 2.9 | 0.5 | 5.6 |
| 0.55 | 7.5 | 0.55 | 5.7 | 0.55 | 5.8 | 0.55 | 2.9 | 0.55 | 5.6 |
| 0.6 | 7.5 | 0.6 | 5.7 | 0.6 | 5.8 | 0.6 | 2.9 | 0.6 | 5.6 |
| 0.65 | 7.5 | 0.65 | 5.6 | 0.65 | 5.8 | 0.65 | 2.9 | 0.65 | 5.6 |
| 0.7 | 7.5 | 0.7 | 5.4 | 0.7 | 5.8 | 0.7 | 2.9 | 0.7 | 5.6 |
| 0.75 | 7.3 | 0.75 | 5.2 | 0.75 | 5.8 | 0.75 | 2.9 | 0.75 | 5.5 |
| 0.8 | 7.0 | 0.8 | 4.9 | 0.8 | 5.8 | 0.8 | 2.7 | 0.8 | 5.2 |
| 0.85 | 6.4 | 0.85 | 4.4 | 0.85 | 5.7 | 0.85 | 2.5 | 0.85 | 4.8 |
| 0.9 | 5.4 | 0.9 | 3.6 | 0.9 | 4.9 | 0.9 | 2.2 | 0.9 | 4.1 |
| 0.95 | 3.7 | 0.95 | 2.6 | 0.95 | 3.5 | 0.95 | 1.6 | 0.95 | 2.9 |
| 1 | 1.2 | 1 | 1.2 | 1 | 1.2 | 1 | 1.2 | 1 | 1.2 |

| HF-HFO-1234yf-HFC-245cb-HFO-1234zeE-HCFO-1233zdE | | | | | | | | | |
|---|---|---|---|---|---|---|---|---|---|
| Organics 0.9 F1234yf + 0.033 F1234zeZ + 0.033 F245cb + 0.034 F1233zdE | | Organics 0.033 F1234yf + 0.9 F1234zeZ + 0.033 F245cb + 0.034 F1233zdE | | Organics 0.033 F1234yf + 0.033 F1234zeZ + 0.9 F245cb + 0.034 F1233zdE | | Organics 0.034 F1234yf + 0.033 F1234zeZ + 0.033 F245cb + 0.9 F1233zdE | | Organics 0.25 F1234yf + 0.25 F1234zeZ + 0.25 F245cb + 0.25 F1233zdE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 2.1 | 0 | 4.5 | 0 | 1.7 | 0 | 3.7 |
| 0.05 | 7.4 | 0.05 | 3.2 | 0.05 | 5.7 | 0.05 | 2.8 | 0.05 | 4.8 |
| 0.1 | 7.4 | 0.1 | 3.2 | 0.1 | 5.7 | 0.1 | 2.8 | 0.1 | 4.8 |
| 0.15 | 7.4 | 0.15 | 3.2 | 0.15 | 5.7 | 0.15 | 2.8 | 0.15 | 4.8 |
| 0.2 | 7.4 | 0.2 | 3.2 | 0.2 | 5.7 | 0.2 | 2.8 | 0.2 | 4.8 |
| 0.25 | 7.4 | 0.25 | 3.2 | 0.25 | 5.7 | 0.25 | 2.8 | 0.25 | 4.8 |
| 0.3 | 7.4 | 0.3 | 3.2 | 0.3 | 5.7 | 0.3 | 2.8 | 0.3 | 4.8 |
| 0.35 | 7.4 | 0.35 | 3.2 | 0.35 | 5.7 | 0.35 | 2.8 | 0.35 | 4.8 |
| 0.4 | 7.4 | 0.4 | 3.2 | 0.4 | 5.7 | 0.4 | 2.8 | 0.4 | 4.8 |
| 0.45 | 7.4 | 0.45 | 3.2 | 0.45 | 5.7 | 0.45 | 2.8 | 0.45 | 4.8 |
| 0.5 | 7.4 | 0.5 | 3.2 | 0.5 | 5.7 | 0.5 | 2.8 | 0.5 | 4.8 |
| 0.55 | 7.4 | 0.55 | 3.2 | 0.55 | 5.7 | 0.55 | 2.8 | 0.55 | 4.8 |
| 0.6 | 7.4 | 0.6 | 3.2 | 0.6 | 5.7 | 0.6 | 2.8 | 0.6 | 4.9 |
| 0.65 | 7.4 | 0.65 | 3.2 | 0.65 | 5.7 | 0.65 | 2.8 | 0.65 | 4.9 |
| 0.7 | 7.4 | 0.7 | 3.2 | 0.7 | 5.7 | 0.7 | 2.8 | 0.7 | 4.9 |
| 0.75 | 7.2 | 0.75 | 3.2 | 0.75 | 5.7 | 0.75 | 2.8 | 0.75 | 4.9 |
| 0.8 | 6.9 | 0.8 | 3.0 | 0.8 | 5.7 | 0.8 | 2.7 | 0.8 | 4.7 |
| 0.85 | 6.4 | 0.85 | 2.8 | 0.85 | 5.7 | 0.85 | 2.5 | 0.85 | 4.3 |
| 0.9 | 5.4 | 0.9 | 2.5 | 0.9 | 4.9 | 0.9 | 2.2 | 0.9 | 3.7 |
| 0.95 | 3.7 | 0.95 | 2.0 | 0.95 | 3.5 | 0.95 | 1.8 | 0.95 | 2.7 |
| 1 | 1.2 | 1 | 1.2 | 1 | 1.2 | 1 | 1.2 | 1 | 1.2 |

-continued

HF-HFO-1234yf-HFC-245cb-HCFO-1233zdE-HFO-1243zf

| Organics 0.9 F1234yf + 0.033 F1233zdE + 0.033 F245cb + 0.034 F1234zf | | Organics 0.033 F1234yf + 0.9 F1233zdE + 0.033 F245cb + 0.034 F1243zf | | Organics 0.033 F1234yf + 0.033 F1233zdE + 0.9 F245cb + 0.034 F1243zf | | Organics 0.034 F1234yf + 0.033 F1233zdE + 0.033 F245cb + 0.9 F1243zf | | Organics 0.25 F1234yf + 0.25 F1233zdE + 0.25 F245cb + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 1.8 | 0 | 4.7 | 0 | 5.7 | 0 | 4.8 |
| 0.05 | 7.5 | 0.05 | 2.9 | 0.05 | 5.8 | 0.05 | 6.7 | 0.05 | 5.9 |
| 0.1 | 7.5 | 0.1 | 2.9 | 0.1 | 5.8 | 0.1 | 6.7 | 0.1 | 5.9 |
| 0.15 | 7.5 | 0.15 | 2.9 | 0.15 | 5.8 | 0.15 | 6.7 | 0.15 | 5.9 |
| 0.2 | 7.5 | 0.2 | 2.9 | 0.2 | 5.8 | 0.2 | 6.7 | 0.2 | 5.9 |
| 0.25 | 7.5 | 0.25 | 2.9 | 0.25 | 5.8 | 0.25 | 6.7 | 0.25 | 5.9 |
| 0.3 | 7.5 | 0.3 | 2.9 | 0.3 | 5.8 | 0.3 | 6.7 | 0.3 | 5.9 |
| 0.35 | 7.5 | 0.35 | 2.9 | 0.35 | 5.8 | 0.35 | 6.7 | 0.35 | 5.9 |
| 0.4 | 7.5 | 0.4 | 2.9 | 0.4 | 5.8 | 0.4 | 6.7 | 0.4 | 5.9 |
| 0.45 | 7.5 | 0.45 | 2.9 | 0.45 | 5.8 | 0.45 | 6.7 | 0.45 | 5.9 |
| 0.5 | 7.5 | 0.5 | 2.9 | 0.5 | 5.8 | 0.5 | 6.7 | 0.5 | 5.9 |
| 0.55 | 7.5 | 0.55 | 2.9 | 0.55 | 5.8 | 0.55 | 6.7 | 0.55 | 5.9 |
| 0.6 | 7.5 | 0.6 | 2.9 | 0.6 | 5.8 | 0.6 | 6.6 | 0.6 | 5.9 |
| 0.65 | 7.5 | 0.65 | 2.9 | 0.65 | 5.8 | 0.65 | 6.6 | 0.65 | 5.9 |
| 0.7 | 7.5 | 0.7 | 2.9 | 0.7 | 5.8 | 0.7 | 6.5 | 0.7 | 5.9 |
| 0.75 | 7.3 | 0.75 | 2.9 | 0.75 | 5.8 | 0.75 | 6.3 | 0.75 | 5.8 |
| 0.8 | 7.0 | 0.8 | 2.8 | 0.8 | 5.8 | 0.8 | 6.1 | 0.8 | 5.6 |
| 0.85 | 6.5 | 0.85 | 2.6 | 0.85 | 5.8 | 0.85 | 5.6 | 0.85 | 5.1 |
| 0.9 | 5.4 | 0.9 | 2.3 | 0.9 | 5.0 | 0.9 | 4.7 | 0.9 | 4.4 |
| 0.95 | 3.6 | 0.95 | 1.6 | 0.95 | 3.5 | 0.95 | 3.4 | 0.95 | 3.1 |
| 1 | 1.2 | 1 | 1.2 | 1 | 1.2 | 1 | 1.2 | 1 | 1.2 |

HF-HCFO-1233xf-HFC-245cb-HCFO-1233zdE-HFO-1243yf

| Organics 0.9 F1233xf + 0.033 F1233zdE + 0.033 F245cb + 0.034 F1234yf | | Organics 0.033 F1233xf + 0.9 F1233zdE + 0.033 F245cb + 0.034 F1234yf | | Organics 0.033 F1233xf + 0.033 F1233zdE + 0.9 F245cb + 0.034 F1234yf | | Organics 0.034 F1233xf + 0.033 F1233zdE + 0.033 F245cb + 0.9 F1234yf | | Organics 0.25 F1233xf + 0.25 F1233zdE + 0.25 F245cb + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 1.7 | 0 | 4.5 | 0 | 6.4 | 0 | 3.7 |
| 0.05 | 3.0 | 0.05 | 2.8 | 0.05 | 5.7 | 0.05 | 7.4 | 0.05 | 4.8 |
| 0.1 | 3.0 | 0.1 | 2.8 | 0.1 | 5.7 | 0.1 | 7.4 | 0.1 | 4.8 |
| 0.15 | 3.0 | 0.15 | 2.8 | 0.15 | 5.7 | 0.15 | 7.4 | 0.15 | 4.8 |
| 0.2 | 3.0 | 0.2 | 2.8 | 0.2 | 5.7 | 0.2 | 7.4 | 0.2 | 4.8 |
| 0.25 | 3.0 | 0.25 | 2.8 | 0.25 | 5.7 | 0.25 | 7.4 | 0.25 | 4.8 |
| 0.3 | 3.0 | 0.3 | 2.8 | 0.3 | 5.7 | 0.3 | 7.4 | 0.3 | 4.8 |
| 0.35 | 3.0 | 0.35 | 2.8 | 0.35 | 5.7 | 0.35 | 7.4 | 0.35 | 4.8 |
| 0.4 | 3.0 | 0.4 | 2.8 | 0.4 | 5.7 | 0.4 | 7.4 | 0.4 | 4.8 |
| 0.45 | 3.0 | 0.45 | 2.8 | 0.45 | 5.7 | 0.45 | 7.4 | 0.45 | 4.8 |
| 0.5 | 3.0 | 0.5 | 2.8 | 0.5 | 5.7 | 0.5 | 7.4 | 0.5 | 4.8 |
| 0.55 | 3.0 | 0.55 | 2.8 | 0.55 | 5.7 | 0.55 | 7.4 | 0.55 | 4.8 |
| 0.6 | 3.0 | 0.6 | 2.8 | 0.6 | 5.7 | 0.6 | 7.4 | 0.6 | 4.8 |
| 0.65 | 3.0 | 0.65 | 2.8 | 0.65 | 5.7 | 0.65 | 7.4 | 0.65 | 4.9 |
| 0.7 | 3.0 | 0.7 | 2.8 | 0.7 | 5.7 | 0.7 | 7.4 | 0.7 | 4.9 |
| 0.75 | 3.0 | 0.75 | 2.8 | 0.75 | 5.7 | 0.75 | 7.2 | 0.75 | 4.9 |
| 0.8 | 2.8 | 0.8 | 2.7 | 0.8 | 5.7 | 0.8 | 6.9 | 0.8 | 4.7 |
| 0.85 | 2.6 | 0.85 | 2.5 | 0.85 | 5.7 | 0.85 | 6.4 | 0.85 | 4.3 |
| 0.9 | 2.3 | 0.9 | 2.2 | 0.9 | 4.9 | 0.9 | 5.4 | 0.9 | 3.7 |
| 0.95 | 1.8 | 0.95 | 1.8 | 0.95 | 3.5 | 0.95 | 3.7 | 0.95 | 2.7 |
| 1 | 1.2 | 1 | 1.2 | 1 | 1.2 | 1 | 1.2 | 1 | 1.2 |

Example 11: Temperature and Pressure Range of Penternary Mixtures

| System with 5 compounds | Boiling point range Temperature ° C. | Boiling point range Pressure bar abs |
|---|---|---|
| HF-HCFO-1233xf-HFC-245cb-HCFO-1233zdE-HFO-1234zeE | 0 to 40 | ~1.0 to ~8.9 |
| HF-HCFO-1233xf-HFC-245cb-HCFO-1233zdE-HFO-1234zeZ | 0 to 40 | ~1.0 to ~8.8 |
| HF-HCFO-1233xf-HFC-245cb-HCFO-1233zdE-HFO-1243zf | 0 to 40 | ~1.0 to ~10.0 |
| HF-HCFO-1233xf-HFO-1234yf-HCFO-1233zdE-HFO-1243zf | 0 to 40 | ~1.0 to ~11.2 |
| HF-HCFO-1233xf-HCFO-1233zdE-HFO-1234zeE-HFO-1234zeZ | 0 to 40 | ~0.9 to ~8.6 |
| HF-HCFO-1233xf-HCFO-1233zdE-HFO-1234zeE-HFO-1243zf | 0 to 40 | ~1.0 to ~10.1 |
| HF-HCFO-1233xf-HCFO-1233zdE-HFO-1234zeZ-HFO-1243zf | 0 to 40 | ~1.0 to ~9.9 |
| HF-HFC-245cb-HCFO-1233zdE-HFO-1234zeE-HFO-1234zeZ | 0 to 40 | ~1.0 to ~8.9 |
| HF-HFC-245cb-HCFO-1233zdE-HFO-1234zeE-HFO-1243zf | 0 to 40 | ~1.1 to ~10.2 |
| HF-HFC-245cb-HCFO-1233zdE-HFO-1234zeZ-HFO-1243zf | 0 to 40 | ~1.0 to ~10.1 |
| HF-HCFO-1233zdE-HFO-1234zeE-HFO-1234zeZ-HFO-1243zf | 0 to 40 | ~1.0 to ~10.1 |
| HF-HCFO-1233xf-HFC-245cb-HCFO-1233zdE-HFO-1234yf | 0 to 40 | ~1.0 to ~11.2 |
| HF-HCFO-1233xf-HFO-1234yf-HFO-1234zeE-HCFO-1233zdE | 0 to 40 | ~1.0 to ~11.2 |
| HF-HCFO-1233xf-HFO-1234yf-HFO-1234zeZ-HCFO-1233zdE | 0 to 40 | ~1.0 to ~11.1 |
| HF-HFO-1234yf-HFO-1234zeE-HFO-1234zeZ-HCFO-1233zdE | 0 to 40 | ~1.0 to ~11.2 |
| HF-HFO-1234yf-HFO-1234zeE-HCFO-1233zdE-HFO-1243zf | 0 to 40 | ~1.0 to ~11.4 |
| HF-HFO-1234yf-HFO-1234zeZ-HCFO-1233zdE-HFO-1243zf | 0 to 40 | ~1.1 to ~11.2 |
| HF-HFO-1234yf-HFC-245cb-HFO-1234zeE-HCFO-1233zdE | 0 to 40 | ~1.1 to ~11.4 |
| HF-HFO-1234yf-HFC-245cb-HFO-1234zeZ-HCFO-1233zdE | 0 to 40 | ~1.0 to ~11.2 |
| HF-HFO-1234yf-HFC-245cb-HCFO-1233zdE-HFO-1243zf | 0 to 40 | ~1.1 to ~11.4 |

Example 12: Decantation Range of Penternary Mixtures

| System with 5 compounds | Decantation ranges Mass percentage of HF | | |
|---|---|---|---|
| | Isotherm 0° C. | Isotherm 25° C. | Isotherm 40° C. |
| HF-HCFO-1233xf-HFC-245cb-HCFO-1233zdE-HFO-1234zeE | 5-75 | 5-70 | 10-60 |
| HF-HCFO-1233xf-HFC-245cb-HCFO-1233zdE-HFO-1234zeZ | 5-80 | 5-75 | 5-70 |
| HF-HCFO-1233xf-HFC-245cb-HCFO-1233zdE-HFO-1243zf | 5-75 | 5-70 | 5-65 |
| HF-HCFO-1233xf-HCFO-1233zdE-HFO-1234zeE-HFO-1234zeZ | 5-75 | 5-70 | 5-60 |
| HF-HCFO-1233xf-HCFO-1233zdE-HFO-1234zeE-HFO-1243zf | 5-75 | 5-65 | 15-45 |
| HF-HCFO-1233xf-HCFO-1233zdE-HFO-1234zeZ-HFO-1243zf | 5-75 | 5-70 | 10-60 |
| HF-HFC-245cb-HCFO-1233zdE-HFO-1234zeE-HFO-1234zeZ | 5-75 | 5-70 | 10-60 |
| HF-HFC-245cb-HCFO-1233zdE-HFO-1234zeE-HFO-1243zf | 5-75 | 10-65 | * |
| HF-HFC-245cb-HCFO-1233zdE-HFO-1234zeZ-HFO-1243zf | 5-75 | 5-70 | 10-60 |
| HF-HCFO-1233zdE-HFO-1234zeE-HFO-1234zeZ-HFO-1243zf | 5-75 | 5-65 | 15-50 |
| HF-HCFO-1233xf-HFC-245cb-HCFO-1233zdE-HFO-1234yf | 5-75 | 5-75 | 10-65 |
| HF-HCFO-1233xf-HFO-1234yf-HFO-1234zeE-HCFO-1233zdE | 5-75 | 5-65 | 10-50 |
| HF-HCFO-1233xf-HFO-1234yf-HFO-1234zeZ-HCFO-1233zdE | 5-75 | 5-70 | 10-60 |
| HF-HCFO-1233xf-HFO-1234yf-HCFO-1233zdE-HFO-1243zf | 5-75 | 5-65 | 15-45 |
| HF-HFO-1234yf-HFO-1234zeE-HFO-1234zeZ-HCFO-1233zdE | 5-75 | 5-65 | 15-45 |
| HF-HFO-1234yf-HFO-1234zeE-HCFO-1233zdE-HFO-1243zf | 5-70 | 10-60 | * |
| HF-HFO-1234yf-HFO-1234zeZ-HCFO-1233zdE-HFO-1243zf | 5-75 | 10-65 | 15-45 |
| HF-HFO-1234yf-HFC-245cb-HFO-1234zeE-HCFO-1233zdE | 5-75 | 10-70 | * |
| HF-HFO-1234yf-HFC-245cb-HFO-1234zeZ-HCFO-1233zdE | 5-75 | 5-75 | 10-65 |
| HF-HFO-1234yf-HFC-245cb-HCFO-1233zdE-HFO-1243zf | 5-75 | 10-70 | * |

Example 13: System with Six Compounds, Isotherm at 25° C.

| HF-HCFO-1233xf-HFC-245cb-HFO-1234zeE-HFO-1234zeZ-HCFO-1233zdE | | | | | | | | | | | |
|---|---|---|---|---|---|---|---|---|---|---|---|
| Organics 0.2 F1233xf + 0.2 F245cb + 0.2 F123zdE 0.2 F1234zeE + 0.2 F1234zeZ | | Organics 0.96 F1233xf + 0.01 F245cb + 0.01F1233zdE + 0.01 F1234zeE + 0.01 F1234zeZ | | Organics 0.01 F1233xf + 0.96 F245cb + 0.01 F1233zdE + 0.01 F1234zeE + 0.01 F1234zeZ | | Organics 0.01 F1233xf + 0.01 F245cb + 0.96 F1233zdE + 0.01 F1234zeE + 0.01 F1234zeZ | | Organics 0.01 F1233xf + 0.01 F245cb + 0.01 F1233zdE + 0.96 F1234zeE + 0.01 F1234zeZ | | Organics 0.01 F1233xf + 0.01 F245cb + 0.01 F1233zdE + 0.01 F1234zeE + 0.96 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.9 | 0 | 1.6 | 0 | 4.6 | 0 | 1.4 | 0 | 4.8 | 0 | 1.9 |
| 0.05 | 4.0 | 0.05 | 2.7 | 0.05 | 5.7 | 0.05 | 2.5 | 0.05 | 5.7 | 0.05 | 3.0 |
| 0.1 | 4.0 | 0.1 | 2.7 | 0.1 | 5.7 | 0.1 | 2.5 | 0.1 | 5.8 | 0.1 | 3.0 |
| 0.15 | 4.0 | 0.15 | 2.7 | 0.15 | 5.7 | 0.15 | 2.5 | 0.15 | 5.8 | 0.15 | 3.0 |
| 0.2 | 4.0 | 0.2 | 2.7 | 0.2 | 5.7 | 0.2 | 2.5 | 0.2 | 5.8 | 0.2 | 3.0 |
| 0.25 | 4.0 | 0.25 | 2.7 | 0.25 | 5.7 | 0.25 | 2.5 | 0.25 | 5.8 | 0.25 | 3.0 |
| 0.3 | 4.0 | 0.3 | 2.7 | 0.3 | 5.7 | 0.3 | 2.5 | 0.3 | 5.8 | 0.3 | 3.0 |
| 0.35 | 4.0 | 0.35 | 2.7 | 0.35 | 5.7 | 0.35 | 2.5 | 0.35 | 5.7 | 0.35 | 3.0 |
| 0.4 | 4.0 | 0.4 | 2.7 | 0.4 | 5.7 | 0.4 | 2.5 | 0.4 | 5.7 | 0.4 | 3.0 |
| 0.45 | 4.0 | 0.45 | 2.7 | 0.45 | 5.7 | 0.45 | 2.5 | 0.45 | 5.7 | 0.45 | 3.0 |
| 0.5 | 4.0 | 0.5 | 2.7 | 0.5 | 5.7 | 0.5 | 2.5 | 0.5 | 5.7 | 0.5 | 3.0 |
| 0.55 | 4.0 | 0.55 | 27 | 0.55 | 57 | 0.55 | 2.5 | 0.55 | 5.6 | 0.55 | 3.0 |
| 0.6 | 4.0 | 0.6 | 2.7 | 0.6 | 5.7 | 0.6 | 2.5 | 0.6 | 5.6 | 0.6 | 3.0 |
| 0.65 | 4.0 | 0.65 | 2.7 | 0.65 | 5.7 | 0.65 | 2.5 | 0.65 | 5.5 | 0.65 | 3.0 |
| 0.7 | 4.0 | 0.7 | 2.7 | 0.7 | 5.8 | 0.7 | 2.5 | 0.7 | 5.3 | 0.7 | 3.0 |
| 0.75 | 4.0 | 0.75 | 2.7 | 0.75 | 5.8 | 0.75 | 2.5 | 0.75 | 5.1 | 0.75 | 3.0 |
| 0.8 | 3.8 | 0.8 | 2.6 | 0.8 | 5.8 | 0.8 | 2.4 | 0.0 | 4.7 | 0.8 | 2.8 |
| 0.85 | 3.5 | 0.85 | 2.4 | 0.85 | 5.8 | 0.85 | 2.2 | 0.85 | 4.3 | 0.85 | 2.6 |
| 0.9 | 3.0 | 0.9 | 2.1 | 0.9 | 5.0 | 0.9 | 2.0 | 0.9 | 3.6 | 0.9 | 2.3 |
| 0.95 | 2.3 | 0.95 | 1.7 | 0.95 | 3.5 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

| HF-HCFO-1233xf-HFC-245cb-HFO-1234zeE-HCFO-1233zdZ-HFO-1234zf | | | | | | | | | | | |
|---|---|---|---|---|---|---|---|---|---|---|---|
| Organics 0.2 F1233xf + 0.2 F245cb + 0.2 F1243zf + 0.2 F1234zeE + 0.2 F1233zdE | | Organics 0.96 F1233xf + 0.01 F245cb + 0.01 F1243zf + 0.01 F1234zeE + 0.01 F1233zdE | | Organics 0.01 F1233xf + 0.96 F245cb + 0.01 F1243zf + 0.01 F1234zeE + 0.01 F1233zdE | | Organics 0.01 F1233xf + 0.01 F245cb + 0.96 F1243zf + 0.01 F1234zeE + 0.01 F1233zdE | | Organics 0.01 F1233xf + 0.01 F245cb + 0.01 F1243zf + 0.96 F1234zeE + 0.01 F1233zdE | | Organics 0.01 F1233xf + 0.01 F245cb + 0.01 F1243zf + 0.01 F1234zeE + 0.96 F1233zdE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.8 | 0 | 1.7 | 0 | 4.6 | 0 | 5.6 | 0 | 4.8 | 0 | 1.5 |
| 0.05 | 4.9 | 0.05 | 2.8 | 0.05 | 5.8 | 0.05 | 6.7 | 0.05 | 5.8 | 0.05 | 2.6 |
| 0.1 | 4.9 | 0.1 | 2.8 | 0.1 | 5.8 | 0.1 | 6.7 | 0.1 | 5.8 | 0.1 | 2.6 |
| 0.15 | 4.9 | 0.15 | 2.8 | 0.15 | 5.8 | 0.15 | 6.7 | 0.15 | 5.8 | 0.15 | 2.6 |
| 0.2 | 4.9 | 0.2 | 2.8 | 0.2 | 5.8 | 0.2 | 6.7 | 0.2 | 5.8 | 0.2 | 2.6 |
| 0.25 | 4.9 | 0.25 | 2.8 | 0.25 | 5.8 | 0.25 | 6.7 | 0.25 | 5.8 | 0.25 | 2.6 |

-continued

| | | | | | | | | | | | |
|---|---|---|---|---|---|---|---|---|---|---|---|
| 0.3 | 4.9 | 0.3 | 2.8 | 0.3 | 5.8 | 0.3 | 6.7 | 0.3 | 5.8 | 0.3 | 2.6 |
| 0.35 | 4.9 | 0.35 | 2.8 | 0.35 | 5.8 | 0.35 | 6.7 | 0.35 | 5.8 | 0.35 | 2.6 |
| 0.4 | 4.9 | 0.4 | 2.8 | 0.4 | 5.8 | 0.4 | 6.7 | 0.4 | 5.8 | 0.4 | 2.6 |
| 0.45 | 4.9 | 0.45 | 2.8 | 0.45 | 5.8 | 0.45 | 6.7 | 0.45 | 5.8 | 0.45 | 2.6 |
| 0.5 | 4.9 | 0.5 | 2.8 | 0.5 | 5.8 | 0.5 | 6.7 | 0.5 | 5.7 | 0.5 | 2.6 |
| 0.55 | 4.9 | 0.55 | 2.8 | 0.55 | 5.8 | 0.55 | 6.7 | 0.55 | 5.7 | 0.55 | 2.6 |
| 0.6 | 4.9 | 0.6 | 2.8 | 0.6 | 5.8 | 0.6 | 6.6 | 0.6 | 5.6 | 0.6 | 2.6 |
| 0.65 | 4.9 | 0.65 | 2.8 | 0.65 | 5.8 | 0.65 | 6.6 | 0.65 | 5.5 | 0.65 | 2.5 |
| 0.7 | 4.9 | 0.7 | 2.8 | 0.7 | 5.8 | 0.7 | 6.5 | 0.7 | 5.4 | 0.7 | 2.5 |
| 0.75 | 4.7 | 0.75 | 2.8 | 0.75 | 5.8 | 0.75 | 6.3 | 0.75 | 5.1 | 0.75 | 2.5 |
| 0.8 | 4.5 | 0.8 | 2.6 | 0.8 | 5.8 | 0.8 | 6.0 | 0.8 | 4.8 | 0.8 | 2.4 |
| 0.85 | 4.1 | 0.85 | 2.4 | 0.85 | 5.8 | 0.85 | 5.6 | 0.85 | 4.3 | 0.85 | 2.3 |
| 0.9 | 3.5 | 0.9 | 2.2 | 0.9 | 5.0 | 0.9 | 4.7 | 0.9 | 3.6 | 0.9 | 2.0 |
| 0.95 | 2.6 | 0.95 | 1.7 | 0.95 | 3.5 | 0.95 | 3.3 | 0.95 | 2.6 | 0.95 | 1.7 |
| 1 | 1.2 | 1 | 1.2 | 1 | 1.2 | 1 | 1.2 | 1 | 1.2 | 1 | 1.2 |

HF-HCFO-1233xf-HFC-245cb-HFO-1234zeZ-HCFO-1233zdE-HFO-1234zf

| Organics 0.2 F1233xf + 0.2 F245cb + 0.2 F1243zf + 0.2 F1234zeZ + 0.2 F1233zdE | | Organics 0.96 F1233xf + 0.01 F245cb + 0.01 F1243zf + 0.01 F1234zeZ + 0.01 F1233zdE | | Organics 0.01 F1233xf + 0.96 F245cb + 0.01 F1243zf + 0.01 F1234zeZ + 0.01 F1233zdE | | Organics 0.01 F1233xf + 0.01 F245cb + 0.96 F1243zf + 0.01 F1234zeZ + 0.01 F1233zdE | | Organics 0.01 F1233xf + 0.01 F245cb + 0.01 F1243zf + 0.96 F1234zeZ + 0.01 F1233zdE | | Organics 0.01 F1233xf + 0.01 F245cb + 0.01 F1243zf + 0.01 F1234zeZ + 0.96 F1233zdE | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.2 | 0 | 1.6 | 0 | 4.6 | 0 | 5.7 | 0 | 1.9 | 0 | 1.4 |
| 0.05 | 4.3 | 0.05 | 2.7 | 0.05 | 5.7 | 0.05 | 6.7 | 0.05 | 3.0 | 0.05 | 2.5 |
| 0.1 | 4.3 | 0.1 | 2.7 | 0.1 | 5.7 | 0.1 | 6.7 | 0.1 | 3.0 | 0.1 | 2.5 |
| 0.15 | 4.3 | 0.15 | 2.7 | 0.15 | 5.7 | 0.15 | 6.7 | 0.15 | 3.0 | 0.15 | 2.5 |
| 0.2 | 4.3 | 0.2 | 2.7 | 0.2 | 5.7 | 0.2 | 6.7 | 0.2 | 3.0 | 0.2 | 2.5 |
| 0.25 | 4.3 | 0.25 | 2.7 | 0.25 | 5.7 | 0.25 | 6.7 | 0.25 | 3.0 | 0.25 | 2.5 |
| 0.3 | 4.3 | 0.3 | 2.7 | 0.3 | 5.7 | 0.3 | 6.7 | 0.3 | 3.0 | 0.3 | 2.5 |
| 0.35 | 4.3 | 0.35 | 2.7 | 0.35 | 5.7 | 0.35 | 6.7 | 0.35 | 3.0 | 0.35 | 2.5 |
| 0.4 | 4.3 | 0.4 | 2.7 | 0.4 | 5.8 | 0.4 | 6.7 | 0.4 | 3.0 | 0.4 | 2.5 |
| 0.45 | 4.3 | 0.45 | 2.7 | 0.45 | 5.8 | 0.45 | 6.7 | 0.45 | 3.0 | 0.45 | 2.5 |
| 0.5 | 4.3 | 0.5 | 2.7 | 0.5 | 5.8 | 0.5 | 6.7 | 0.5 | 3.0 | 0.5 | 2.5 |
| 0.55 | 4.3 | 0.55 | 2.7 | 0.55 | 5.8 | 0.55 | 6.7 | 0.55 | 3.0 | 0.55 | 2.5 |
| 0.6 | 4.3 | 0.6 | 2.7 | 0.6 | 5.8 | 0.6 | 6.6 | 0.6 | 3.0 | 0.6 | 2.5 |
| 0.65 | 4.3 | 0.65 | 2.7 | 0.65 | 5.8 | 0.65 | 6.6 | 0.65 | 3.0 | 0.65 | 2.5 |
| 0.7 | 4.3 | 0.7 | 2.7 | 0.7 | 5.8 | 0.7 | 6.6 | 0.7 | 3.0 | 0.7 | 2.5 |
| 0.75 | 4.3 | 0.75 | 2.7 | 0.75 | 5.8 | 0.75 | 6.3 | 0.75 | 3.0 | 0.75 | 2.5 |
| 0.8 | 4.1 | 0.8 | 2.6 | 0.8 | 5.8 | 0.8 | 6.0 | 0.8 | 2.9 | 0.8 | 2.4 |
| 0.85 | 3.6 | 0.85 | 2.4 | 0.85 | 5.8 | 0.85 | 5.5 | 0.85 | 2.7 | 0.85 | 2.3 |
| 0.9 | 3.3 | 0.9 | 2.1 | 0.9 | 5.0 | 0.9 | 4.7 | 0.9 | 2.3 | 0.9 | 2.0 |
| 0.95 | 2.4 | 0.95 | 1.7 | 0.95 | 3.5 | 0.95 | 3.3 | 0.95 | 1.9 | 0.95 | 1.7 |
| 1 | 1.2 | 1 | 1.2 | 1 | 1.2 | 1 | 1.2 | 1 | 1.2 | 1 | 1.2 |

-continued

HF-HCFO-1233xf-HFO-1234zeE-HFO-1234zeZ-HCFO-1233zdE-HFO-1243zf

| Organics 0.2 F1233xf + 0.2 F1243zf + 0.2 F1233zdE 0.2 F1234zeE + 0.2 F1234zeZ | | Organics 0.09 F1233xf + 0.01 F1243zf + 0.01 F1233zdE + 0.01 F1234zeE + 0.01 F1234zeZ | | Organics 0.01 F1233xf + 0.96 F1243zf + 0.01 F1233zdE + 0.01 F1234zeE + 0.01 F1234zeZ | | Organics 0.01 F1233xf + 0.01 F1243zf + 0.96 F1233zdE + 0.01 F1234zeE + 0.01 F1234zeZ | | Organics 0.01 F1233xf + 0.01 F1243zf + 0.01 F1233zdE + 0.96 F1234zeE + 0.01 F1234zeZ | | Organics 0.01 F1233xf + 0.01 F1243zf + 0.01 F1233zdE + 0.01 F1234zeE + 0.96 F1234zeZ | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.2 | 0 | 1.6 | 0 | 5.7 | 0 | 4.6 | 0 | 4.8 | 0 | 1.9 |
| 0.05 | 4.3 | 0.05 | 2.7 | 0.05 | 6.7 | 0.05 | 5.7 | 0.05 | 5.7 | 0.05 | 3.0 |
| 0.1 | 4.3 | 0.1 | 2.7 | 0.1 | 6.7 | 0.1 | 5.8 | 0.1 | 5.8 | 0.1 | 3.0 |
| 0.15 | 4.3 | 0.15 | 2.7 | 0.15 | 6.7 | 0.15 | 5.8 | 0.15 | 5.8 | 0.15 | 3.0 |
| 0.2 | 4.3 | 0.2 | 2.7 | 0.2 | 6.7 | 0.2 | 5.8 | 0.2 | 5.8 | 0.2 | 3.0 |
| 0.25 | 4.3 | 0.25 | 2.7 | 0.25 | 6.7 | 0.25 | 5.8 | 0.25 | 5.8 | 0.25 | 3.0 |
| 0.3 | 4.3 | 0.3 | 2.7 | 0.3 | 6.7 | 0.3 | 5.8 | 0.3 | 5.8 | 0.3 | 3.0 |
| 0.35 | 4.3 | 0.35 | 2.7 | 0.35 | 6.7 | 0.35 | 5.8 | 0.35 | 5.8 | 0.35 | 3.0 |
| 0.4 | 4.3 | 0.4 | 2.7 | 0.4 | 6.7 | 0.4 | 5.8 | 0.4 | 5.8 | 0.4 | 3.0 |
| 0.45 | 4.3 | 0.45 | 2.7 | 0.45 | 6.7 | 0.45 | 5.7 | 0.45 | 5.7 | 0.45 | 3.0 |
| 0.5 | 4.3 | 0.5 | 2.7 | 0.5 | 6.7 | 0.5 | 5.7 | 0.5 | 5.7 | 0.5 | 3.0 |
| 0.55 | 4.2 | 0.55 | 2.7 | 0.55 | 6.7 | 0.55 | 5.7 | 0.55 | 5.7 | 0.55 | 3.0 |
| 0.6 | 4.2 | 0.6 | 2.7 | 0.6 | 6.6 | 0.6 | 5.6 | 0.6 | 5.6 | 0.6 | 3.0 |
| 0.65 | 4.2 | 0.65 | 2.7 | 0.65 | 6.6 | 0.65 | 5.5 | 0.65 | 5.5 | 0.65 | 3.0 |
| 0.7 | 4.2 | 0.7 | 2.7 | 0.7 | 6.5 | 0.7 | 5.3 | 0.7 | 5.3 | 0.7 | 3.0 |
| 0.75 | 4.0 | 0.75 | 2.7 | 0.75 | 6.3 | 0.75 | 5.1 | 0.75 | 5.1 | 0.75 | 3.0 |
| 0.8 | 3.8 | 0.8 | 2.6 | 0.8 | 6.0 | 0.8 | 4.7 | 0.8 | 4.7 | 0.8 | 2.8 |
| 0.85 | 3.5 | 0.85 | 2.4 | 0.85 | 5.5 | 0.85 | 4.3 | 0.85 | 4.3 | 0.85 | 2.6 |
| 0.9 | 3.0 | 0.9 | 2.1 | 0.9 | 4.7 | 0.9 | 3.6 | 0.9 | 3.6 | 0.9 | 2.3 |
| 0.95 | 2.2 | 0.95 | 1.7 | 0.95 | 3.3 | 0.95 | 2.6 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF-HFC-245cb-HFO-1234zeE-HFO-1234zeZ-HCFO-1233zdE-HFO-1243zf

| Organics 0.2 F245cb + 0.2 F1243zf + 0.2 F1233zdE 0.2 F1234zeE + 0.2 F1234zeZ | | Organics 0.96 F245cb + 0.01 F1243zf + 0.01 F1233zdE + 0.01 F1234zeE + 0.01 F1234zeZ | | Organics 0.0.1 F245cb + 0.96 F1243zf + 0.01 F1233zdE + 0.01 F1234zeE + 0.01 F1234zeZ | | Organics 0.0.1 F245cb + 0.01 F1243zf + 0.96 F1233zdE + 0.01 F1234zeE + 0.01 F1234zeZ | | Organics 0.0.1 F245cb + 0.01 F1243zf + 0.01 F1233zdE + 0.96 F1234zeE + 0.01 F1234zeZ | | Organics 0.0.1 F245cb + 0.01 F1243zf + 0.01 F1233zdE + 0.01 F1234zeE + 0.96 F1234zeZ | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.9 | 0 | 4.6 | 0 | 5.8 | 0 | 1.51 | 0 | 4.8 | 0 | 1.9 |
| 0.05 | 4.9 | 0.05 | 5.8 | 0.05 | 6.7 | 0.05 | 2.6 | 0.05 | 5.8 | 0.05 | 3.0 |
| 0.1 | 4.9 | 0.1 | 5.8 | 0.1 | 6.7 | 0.1 | 2.6 | 0.1 | 5.8 | 0.1 | 3.0 |
| 0.15 | 4.9 | 0.15 | 5.8 | 0.15 | 6.7 | 0.15 | 2.6 | 0.15 | 5.8 | 0.15 | 3.0 |
| 0.2 | 4.9 | 0.2 | 5.8 | 0.2 | 6.7 | 0.2 | 2.6 | 0.2 | 5.8 | 0.2 | 3.0 |
| 0.25 | 4.9 | 0.25 | 5.8 | 0.25 | 6.7 | 0.25 | 2.6 | 0.25 | 5.8 | 0.25 | 3.0 |
| 0.3 | 4.9 | 0.3 | 5.8 | 0.3 | 6.7 | 0.3 | 2.6 | 0.3 | 5.8 | 0.3 | 3.0 |

-continued

| | | | | | | | | | | | |
|---|---|---|---|---|---|---|---|---|---|---|---|
| 0.35 | 4.9 | 0.35 | 5.8 | 0.35 | 6.7 | 0.35 | 2.6 | 0.35 | 5.8 | 0.35 | 3.0 |
| 0.4 | 4.9 | 0.4 | 5.8 | 0.4 | 6.7 | 0.4 | 2.6 | 0.4 | 5.8 | 0.4 | 3.0 |
| 0.45 | 4.9 | 0.45 | 5.8 | 0.45 | 6.7 | 0.45 | 2.6 | 0.45 | 5.8 | 0.45 | 3.0 |
| 0.5 | 4.9 | 0.5 | 5.8 | 0.5 | 6.7 | 0.5 | 2.6 | 0.5 | 5.7 | 0.5 | 3.0 |
| 0.55 | 4.9 | 0.55 | 5.8 | 0.55 | 6.7 | 0.55 | 2.6 | 0.55 | 5.7 | 0.55 | 3.0 |
| 0.6 | 4.9 | 0.6 | 5.8 | 0.6 | 6.6 | 0.6 | 2.6 | 0.6 | 5.6 | 0.6 | 3.0 |
| 0.65 | 4.9 | 0.65 | 5.8 | 0.65 | 6.6 | 0.65 | 2.6 | 0.65 | 5.5 | 0.65 | 3.0 |
| 0.7 | 4.9 | 0.7 | 5.8 | 0.7 | 6.5 | 0.7 | 2.6 | 0.7 | 5.4 | 0.7 | 3.0 |
| 0.75 | 4.9 | 0.75 | 5.8 | 0.75 | 6.3 | 0.75 | 2.5 | 0.75 | 5.1 | 0.75 | 3.0 |
| 0.8 | 4.5 | 0.8 | 5.8 | 0.8 | 6.0 | 0.8 | 2.4 | 0.8 | 4.8 | 0.8 | 2.9 |
| 0.85 | 4.2 | 0.85 | 5.8 | 0.85 | 5.6 | 0.85 | 2.3 | 0.85 | 4.3 | 0.85 | 2.7 |
| 0.9 | 3.5 | 0.9 | 5.0 | 0.9 | 4.7 | 0.9 | 2.0 | 0.9 | 3.5 | 0.9 | 2.4 |
| 0.95 | 2.6 | 0.95 | 3.5 | 0.95 | 3.4 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF-HCFO-1233xf-HFO-1234yf-HFC-245cb-HFO-1234zeE-HCFO-1233zdE

| Organics 0.2 F1233xf + 0.2 F1234yf + 0.2 F245cb 0.2 F1234zeE + 0.2 F1233zdE | | Organics 0.96 F1233xf + 0.01 F1234yf + 0.01 F245cb + 0.01 F1234zeE + 0.01 F1233zdE | | Organics 0.96 F1233xf + 0.96 F1234yf + 0.01 F245cb + 0.01 F1234zeE + 0.01 F1233zdE | | Organics 0.01 F1233xf + 0.01 F1234yf + 0.96 F245cb + 0.01 F1234zeE + 0.01 F1233zdE | | Organics 0.01 F1233xf + 0.01 F1234yf + 0.01 F245cb + 0.96 F1234zeE + 0.01 F1233zdE | | Organics 0.01 F1233xf + 0.01 F1234yf + 0.01 F245cb + 0.01 F1234zeE + 0.96 F1233zdE | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.9 | 0 | 1.7 | 0 | 6.7 | 0 | 4.6 | 0 | 4.8 | 0 | 1.5 |
| 0.05 | 5.0 | 0.05 | 2.8 | 0.05 | 7.6 | 0.05 | 5.8 | 0.05 | 5.8 | 0.05 | 2.6 |
| 0.1 | 5.0 | 0.1 | 2.8 | 0.1 | 7.6 | 0.1 | 5.8 | 0.1 | 5.8 | 0.1 | 2.6 |
| 0.15 | 5.0 | 0.15 | 2.8 | 0.15 | 7.6 | 0.15 | 5.8 | 0.15 | 5.8 | 0.15 | 2.6 |
| 0.2 | 5.0 | 0.2 | 2.8 | 0.2 | 7.6 | 0.2 | 5.8 | 0.2 | 5.8 | 0.2 | 2.6 |
| 0.25 | 5.0 | 0.25 | 2.8 | 0.25 | 7.6 | 0.25 | 5.8 | 0.25 | 5.8 | 0.25 | 2.6 |
| 0.3 | 5.0 | 0.3 | 2.8 | 0.3 | 7.6 | 0.3 | 5.8 | 0.3 | 5.8 | 0.3 | 2.6 |
| 0.35 | 5.0 | 0.35 | 2.8 | 0.35 | 7.6 | 0.35 | 5.8 | 0.35 | 5.8 | 0.35 | 2.6 |
| 0.4 | 5.0 | 0.4 | 2.8 | 0.4 | 7.6 | 0.4 | 5.8 | 0.4 | 5.8 | 0.4 | 2.6 |
| 0.45 | 5.0 | 0.45 | 2.8 | 0.45 | 7.6 | 0.45 | 5.8 | 0.45 | 5.8 | 0.45 | 2.6 |
| 0.5 | 5.0 | 0.5 | 2.8 | 0.5 | 7.6 | 0.5 | 5.8 | 0.5 | 5.7 | 0.5 | 2.6 |
| 0.55 | 5.0 | 0.55 | 2.8 | 0.55 | 7.6 | 0.55 | 5.8 | 0.55 | 5.7 | 0.55 | 2.6 |
| 0.6 | 5.0 | 0.6 | 2.8 | 0.6 | 7.6 | 0.6 | 5.8 | 0.6 | 5.6 | 0.6 | 2.6 |
| 0.65 | 5.0 | 0.65 | 2.8 | 0.65 | 7.6 | 0.65 | 5.8 | 0.65 | 5.5 | 0.65 | 2.6 |
| 0.7 | 5.1 | 0.7 | 2.8 | 0.7 | 7.6 | 0.7 | 5.8 | 0.7 | 5.4 | 0.7 | 2.6 |
| 0.75 | 5.0 | 0.75 | 2.8 | 0.75 | 7.5 | 0.75 | 5.8 | 0.75 | 5.1 | 0.75 | 2.6 |
| 0.8 | 4.7 | 0.8 | 2.6 | 0.8 | 7.1 | 0.8 | 5.8 | 0.8 | 4.8 | 0.8 | 2.4 |
| 0.85 | 4.3 | 0.85 | 2.5 | 0.85 | 6.5 | 0.85 | 5.8 | 0.85 | 4.3 | 0.85 | 2.3 |
| 0.9 | 3.7 | 0.9 | 2.2 | 0.9 | 5.5 | 0.9 | 5.0 | 0.9 | 3.6 | 0.9 | 2.0 |
| 0.95 | 2.7 | 0.95 | 1.8 | 0.95 | 3.8 | 0.95 | 3.5 | 0.95 | 2.6 | 0.95 | 1.7 |
| 1 | 1.2 | 1 | 1.2 | 1 | 1.2 | 1 | 1.2 | 1 | 1.2 | 1 | 1.2 |

-continued

HF-HCFO-1233xf-HFO-1234yf-HFC-246cb-HFO-1234zeZ-HCFO-1233zdE

| Organics 0.2 F1233xf + 0.2 F1234yf + 0.2 F245cb 0.2 F1234zeZ + 0.2 F1233zdE | | Organics 0.96 F1233xf + 0.01 F1234yf + 0.01 F245cb + 0.01 F1234zeZ + 0.01 F1233zdE | | Organics 0.01 F1233xf + 0.96 F1234yf + 0.01 F245cb + 0.01 F1234zeZ + 0.01 F1233zdE | | Organics 0.01 F1233xf + 0.01 F1234yf + 0.96 F245cb + 0.01 F1234zeZ + 0.01 F1233zdE | | Organics 0.01 F1233xf + 0.01 F1234yf + 0.01 F245cb + 0.96 F1234zeZ + 0.01 F1233zdE | | Organics 0.01 F1233xf + 0.01 F1234yf + 0.01 F245cb + 0.01 F1234zeZ + 0.96 F1233zdE | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.3 | 0 | 1.6 | 0 | 6.6 | 0 | 4.6 | 0 | 1.9 | 0 | 1.4 |
| 0.05 | 4.4 | 0.05 | 2.8 | 0.05 | 7.6 | 0.05 | 5.8 | 0.05 | 3.0 | 0.05 | 2.5 |
| 0.1 | 4.4 | 0.1 | 2.8 | 0.1 | 7.6 | 0.1 | 5.8 | 0.1 | 3.0 | 0.1 | 2.5 |
| 0.15 | 4.4 | 0.15 | 2.8 | 0.15 | 7.6 | 0.15 | 5.8 | 0.15 | 3.0 | 0.15 | 2.5 |
| 0.2 | 4.4 | 0.2 | 2.8 | 0.2 | 7.6 | 0.2 | 5.8 | 0.2 | 3.0 | 0.2 | 2.5 |
| 0.25 | 4.4 | 0.25 | 2.8 | 0.25 | 7.6 | 0.25 | 5.8 | 0.25 | 3.0 | 0.25 | 2.5 |
| 0.3 | 4.4 | 0.3 | 2.8 | 0.3 | 7.6 | 0.3 | 5.8 | 0.3 | 3.0 | 0.3 | 2.5 |
| 0.35 | 4.4 | 0.35 | 2.8 | 0.35 | 7.6 | 0.35 | 5.8 | 0.35 | 3.0 | 0.35 | 2.5 |
| 0.4 | 4.4 | 0.4 | 2.8 | 0.4 | 7.6 | 0.4 | 5.8 | 0.4 | 3.0 | 0.4 | 2.5 |
| 0.45 | 4.4 | 0.45 | 2.8 | 0.45 | 7.6 | 0.45 | 5.8 | 0.45 | 3.0 | 0.45 | 2.5 |
| 0.5 | 4.4 | 0.5 | 2.8 | 0.5 | 7.6 | 0.5 | 5.8 | 0.5 | 3.0 | 0.5 | 2.5 |
| 0.55 | 4.4 | 0.55 | 2.8 | 0.55 | 7.6 | 0.55 | 5.8 | 0.55 | 3.0 | 0.55 | 2.5 |
| 0.6 | 4.4 | 0.6 | 2.8 | 0.6 | 7.6 | 0.6 | 5.8 | 0.6 | 3.0 | 0.6 | 2.5 |
| 0.65 | 4.5 | 0.65 | 2.8 | 0.65 | 7.6 | 0.65 | 5.8 | 0.65 | 3.0 | 0.65 | 2.5 |
| 0.7 | 4.5 | 0.7 | 2.8 | 0.7 | 7.6 | 0.7 | 5.8 | 0.7 | 3.0 | 0.7 | 2.5 |
| 0.75 | 4.3 | 0.75 | 2.8 | 0.75 | 7.4 | 0.75 | 5.8 | 0.75 | 3.0 | 0.75 | 2.5 |
| 0.8 | 4.3 | 0.8 | 2.8 | 0.8 | 7.1 | 0.8 | 5.8 | 0.8 | 2.9 | 0.8 | 2.4 |
| 0.85 | 4.0 | 0.85 | 2.8 | 0.85 | 6.5 | 0.85 | 5.8 | 0.85 | 2.7 | 0.85 | 2.3 |
| 0.9 | 3.4 | 0.9 | 2.8 | 0.9 | 5.5 | 0.9 | 5.0 | 0.9 | 2.3 | 0.9 | 2.0 |
| 0.95 | 2.5 | 0.95 | 1.7 | 0.95 | 3.8 | 0.95 | 3.5 | 0.95 | 1.9 | 0.95 | 1.7 |
| 1 | 1.2 | 1 | 1.2 | 1 | 1.2 | 1 | 1.2 | 1 | 1.2 | 1 | 1.2 |

HF-HCFO-1233xf-HFO-1234yf-HFC-245cb-HCFO-1233zdE-HFO-1243zf

| Organics 0.2 F1233xf + 0.2 F1234yf + 0.2 F245cb 0.2 F1233zdE + 0.2 F1243zf | | Organics 0.96 F1233xf + 0.01 F1234yf + 0.01 F245cb + 0.01 F1233zdE + 0.01 F1243zf | | Organics 0.01 F1233xf + 0.96 F1234yf + 0.01 F245cb + 0.01 F1233zdE + 0.01 F1243zf | | Organics 0.01 F1233xf + 0.01 F1234yf + 0.96 F245cb + 0.01 F1233zdE + 0.01 F1243zf | | Organics 0.01 F1233xf + 0.01 F1234yf + 0.01 F245cb + 0.96 F1233zdE + 0.01 F1243zf | | Organics 0.01 F1233xf + 0.01 F1234yf + 0.01 F245cb + 0.01 F1233zdE + 0.96 F1243zf | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.2 | 0 | 1.7 | 0 | 6.7 | 0 | 4.6 | 0 | 1.5 | 0 | 5.8 |
| 0.05 | 5.3 | 0.05 | 2.8 | 0.05 | 7.6 | 0.05 | 5.8 | 0.05 | 2.6 | 0.05 | 6.7 |
| 0.1 | 5.3 | 0.1 | 2.8 | 0.1 | 7.7 | 0.1 | 5.8 | 0.1 | 2.6 | 0.1 | 6.6 |
| 0.15 | 5.3 | 0.15 | 2.8 | 0.15 | 7.6 | 0.15 | 5.8 | 0.15 | 2.6 | 0.15 | 6.7 |
| 0.2 | 5.3 | 0.2 | 2.8 | 0.2 | 7.6 | 0.2 | 5.8 | 0.2 | 2.6 | 0.2 | 6.7 |
| 0.25 | 5.3 | 0.25 | 2.8 | 0.25 | 7.6 | 0.25 | 5.8 | 0.25 | 2.6 | 0.25 | 6.7 |
| 0.3 | 5.3 | 0.3 | 2.8 | 0.3 | 7.6 | 0.3 | 5.8 | 0.3 | 2.6 | 0.3 | 6.7 |

-continued

| | | | | | | | | | | | |
|---|---|---|---|---|---|---|---|---|---|---|---|
| 0.35 | 5.3 | 0.35 | 2.8 | 0.35 | 7.6 | 0.35 | 5.8 | 0.35 | 2.6 | 0.35 | 6.7 |
| 0.4 | 5.3 | 0.4 | 2.8 | 0.4 | 7.6 | 0.4 | 5.8 | 0.4 | 2.6 | 0.4 | 6.7 |
| 0.45 | 5.3 | 0.45 | 2.8 | 0.45 | 7.6 | 0.45 | 5.8 | 0.45 | 2.6 | 0.45 | 6.7 |
| 0.5 | 5.3 | 0.5 | 2.8 | 0.5 | 7.6 | 0.5 | 5.8 | 0.5 | 2.6 | 0.5 | 6.7 |
| 0.55 | 5.3 | 0.55 | 2.8 | 0.55 | 7.6 | 0.55 | 5.8 | 0.55 | 2.6 | 0.55 | 6.7 |
| 0.6 | 5.3 | 0.6 | 2.8 | 0.6 | 7.6 | 0.6 | 5.8 | 0.6 | 2.6 | 0.6 | 6.7 |
| 0.65 | 5.3 | 0.65 | 2.8 | 0.65 | 7.6 | 0.65 | 5.8 | 0.65 | 2.6 | 0.65 | 6.6 |
| 0.7 | 5.3 | 0.7 | 2.8 | 0.7 | 7.6 | 0.7 | 5.8 | 0.7 | 2.6 | 0.7 | 6.5 |
| 0.75 | 5.2 | 0.75 | 2.8 | 0.75 | 7.5 | 0.75 | 5.8 | 0.75 | 2.6 | 0.75 | 6.4 |
| 0.8 | 5.0 | 0.8 | 2.7 | 0.8 | 7.2 | 0.8 | 5.8 | 0.8 | 2.5 | 0.8 | 6.1 |
| 0.85 | 4.6 | 0.85 | 2.5 | 0.85 | 6.6 | 0.85 | 5.8 | 0.85 | 2.3 | 0.85 | 5.6 |
| 0.9 | 3.9 | 0.9 | 2.2 | 0.9 | 5.5 | 0.9 | 5.0 | 0.9 | 2.0 | 0.9 | 4.7 |
| 0.95 | 2.8 | 0.95 | 1.8 | 0.95 | 3.6 | 0.95 | 3.5 | 0.95 | 1.7 | 0.95 | 3.4 |
| 1 | 1.2 | 1 | 1.2 | 1 | 1.2 | 1 | 1.2 | 1 | 1.2 | 1 | 1.2 |

HF-HCFO-1233xf-HFO-1234yf-HFO-1234zeE-HFO-1234zeZ-HCFO-1233zdE

| Organics 0.2 F1233xf + 0.2 F1234yf + 0.2 F1233zdE 0.2 F1234zeE + 0.2 F1234zeZ | | Organics 0.96 F1233xf + 0.01 F1234yf + 0.01 F1233zdE + 0.01 F1234zeE + 0.01 F1234zeZ | | Organics 0.01 F1233xf + 0.96 F1234yf + 0.01 F1233zdE + 0.01 F1234zeE + 0.01 F1234zeZ | | Organics 0.01 F1233xf + 0.01 F1234yf + 0.96 F1233zdE + 0.01 F1234zeE + 0.01 F1234zeZ | | Organics 0.01 F1233xf + 0.01 F1234yf + 0.01 F1233zdE + 0.96 F1234zeE + 0.01 F1234zeZ | | Organics 0.01 F1233xf + 0.01 F1234yf + 0.01 F1233zdE + 0.01 F1234zeE + 0.96 F1234zeZ | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.4 | 0 | 1.6 | 0 | 6.6 | 0 | 1.4 | 0 | 4.8 | 0 | 1.9 |
| 0.05 | 4.4 | 0.05 | 2.8 | 0.05 | 7.6 | 0.05 | 2.5 | 0.05 | 5.8 | 0.05 | 3.0 |
| 0.1 | 4.4 | 0.1 | 2.8 | 0.1 | 7.6 | 0.1 | 2.5 | 0.1 | 5.8 | 0.1 | 3.0 |
| 0.15 | 4.4 | 0.15 | 2.8 | 0.15 | 7.6 | 0.15 | 2.5 | 0.15 | 5.8 | 0.15 | 3.0 |
| 0.2 | 4.4 | 0.2 | 2.8 | 0.2 | 7.6 | 0.2 | 2.5 | 0.2 | 5.8 | 0.2 | 3.0 |
| 0.25 | 4.4 | 0.25 | 2.8 | 0.25 | 7.6 | 0.25 | 2.5 | 0.25 | 5.8 | 0.25 | 3.0 |
| 0.3 | 4.4 | 0.3 | 2.8 | 0.3 | 7.6 | 0.3 | 2.5 | 0.3 | 5.8 | 0.3 | 3.0 |
| 0.35 | 4.4 | 0.35 | 2.8 | 0.35 | 7.6 | 0.35 | 2.5 | 0.35 | 5.8 | 0.35 | 3.0 |
| 0.4 | 4.4 | 0.4 | 2.8 | 0.4 | 7.6 | 0.4 | 2.5 | 0.4 | 5.8 | 0.4 | 3.0 |
| 0.45 | 4.4 | 0.45 | 2.7 | 0.45 | 7.6 | 0.45 | 2.5 | 0.45 | 5.7 | 0.45 | 3.0 |
| 0.5 | 4.4 | 0.5 | 2.7 | 0.5 | 7.6 | 0.5 | 2.5 | 0.5 | 5.7 | 0.5 | 3.0 |
| 0.55 | 4.4 | 0.55 | 2.7 | 0.55 | 7.6 | 0.55 | 2.5 | 0.55 | 5.7 | 0.55 | 3.0 |
| 0.6 | 4.4 | 0.6 | 2.7 | 0.6 | 7.6 | 0.6 | 2.5 | 0.6 | 5.6 | 0.6 | 3.0 |
| 0.65 | 4.4 | 0.65 | 2.7 | 0.65 | 7.6 | 0.65 | 2.5 | 0.65 | 5.5 | 0.65 | 3.0 |
| 0.7 | 4.4 | 0.7 | 2.7 | 0.7 | 7.6 | 0.7 | 2.5 | 0.7 | 5.3 | 0.7 | 3.0 |
| 0.75 | 4.2 | 0.75 | 2.7 | 0.75 | 7.4 | 0.75 | 2.5 | 0.75 | 5.1 | 0.75 | 3.0 |
| 0.8 | 4.0 | 0.8 | 2.6 | 0.8 | 7.1 | 0.8 | 2.4 | 0.8 | 4.8 | 0.8 | 2.8 |
| 0.85 | 3.6 | 0.85 | 2.4 | 0.85 | 6.5 | 0.85 | 2.2 | 0.85 | 4.3 | 0.85 | 2.6 |
| 0.9 | 3.1 | 0.9 | 2.1 | 0.9 | 5.5 | 0.9 | 2.0 | 0.9 | 3.6 | 0.9 | 2.3 |
| 0.95 | 2.3 | 0.95 | 1.7 | 0.95 | 3.8 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

-continued

HF-HCFO-1233xf-HFO-1234yf-HFO-1234zeE-HCFO-1233zdE-HFO-1243zf

| Organics 0.2 F1233xf + 0.2 F1234yf + 0.2 F1243zf + 0.2 F1234zeE + 0.2 F1233zdE | | Organics 0.96 F1233xf + 0.01 F1234yf + 0.01 F1243zf + 0.01 F1234zeE + 0.01 F1233zdE | | Organics 0.01 F1233xf + 0.96 F1234yf + 0.01 F1243zf + 0.01 F1234zeE + 0.01 F1233zdE | | Organics 0.01 F1233xf + 0.01 F1234yf + 0.96 F1243zf + 0.01 F1234zeE + 0.01 F1233zdE | | Organics 0.01 F1233xf + 0.01 F1234yf + 0.01 F1243zf + 0.96 F1234zeE + 0.01 F1233zdE | | Organics 0.01 F1233xf + 0.01 F1234yf + 0.01 F1243zf + 0.01 F1234zeE + 0.96 F1233zdE | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.3 | 0 | 1.7 | 0 | 6.7 | 0 | 5.8 | 0 | 4.8 | 0 | 1.5 |
| 0.05 | 5.3 | 0.05 | 2.8 | 0.05 | 7.6 | 0.05 | 6.7 | 0.05 | 5.8 | 0.05 | 2.6 |
| 0.1 | 5.3 | 0.1 | 2.8 | 0.1 | 7.6 | 0.1 | 6.7 | 0.1 | 5.8 | 0.1 | 2.6 |
| 0.15 | 5.3 | 0.15 | 2.8 | 0.15 | 7.6 | 0.15 | 6.7 | 0.15 | 5.8 | 0.15 | 2.6 |
| 0.2 | 5.3 | 0.2 | 2.8 | 0.2 | 7.6 | 0.2 | 6.7 | 0.2 | 5.8 | 0.2 | 2.6 |
| 0.25 | 5.3 | 0.25 | 2.8 | 0.25 | 7.6 | 0.25 | 6.7 | 0.25 | 5.8 | 0.25 | 2.6 |
| 0.3 | 5.3 | 0.3 | 2.8 | 0.3 | 7.6 | 0.3 | 6.7 | 0.3 | 5.8 | 0.3 | 2.6 |
| 0.35 | 5.3 | 0.35 | 2.8 | 0.35 | 7.6 | 0.35 | 6.7 | 0.35 | 5.8 | 0.35 | 2.6 |
| 0.4 | 5.3 | 0.4 | 2.8 | 0.4 | 7.6 | 0.4 | 6.7 | 0.4 | 5.8 | 0.4 | 2.6 |
| 0.45 | 5.3 | 0.45 | 2.8 | 0.45 | 7.6 | 0.45 | 6.7 | 0.45 | 5.8 | 0.45 | 2.6 |
| 0.5 | 5.3 | 0.5 | 2.8 | 0.5 | 7.6 | 0.5 | 6.7 | 0.5 | 5.8 | 0.5 | 2.6 |
| 0.55 | 5.3 | 0.55 | 2.8 | 0.55 | 7.6 | 0.55 | 6.7 | 0.55 | 5.7 | 0.55 | 2.6 |
| 0.6 | 5.3 | 0.6 | 2.8 | 0.6 | 7.6 | 0.6 | 6.7 | 0.6 | 5.6 | 0.6 | 2.6 |
| 0.65 | 5.2 | 0.65 | 2.8 | 0.65 | 7.6 | 0.65 | 6.6 | 0.65 | 5.5 | 0.65 | 2.6 |
| 0.7 | 5.1 | 0.7 | 2.8 | 0.7 | 7.6 | 0.7 | 6.5 | 0.7 | 5.4 | 0.7 | 2.6 |
| 0.75 | 5.0 | 0.75 | 2.8 | 0.75 | 7.5 | 0.75 | 6.3 | 0.75 | 5.1 | 0.75 | 2.6 |
| 0.8 | 4.7 | 0.8 | 2.6 | 0.8 | 7.1 | 0.8 | 6.1 | 0.8 | 4.8 | 0.8 | 2.4 |
| 0.85 | 4.3 | 0.85 | 2.5 | 0.85 | 6.5 | 0.85 | 5.6 | 0.85 | 4.3 | 0.85 | 2.3 |
| 0.9 | 3.6 | 0.9 | 2.2 | 0.9 | 5.5 | 0.9 | 4.7 | 0.9 | 3.6 | 0.9 | 2.0 |
| 0.95 | 2.6 | 0.95 | 1.8 | 0.95 | 3.8 | 0.95 | 3.4 | 0.95 | 2.6 | 0.95 | 1.7 |
| 1 | 1.2 | 1 | 1.2 | 1 | 1.2 | 1 | 1.2 | 1 | 1.2 | 1 | 1.2 |

HF-HCFO-1233xf-HFO-1234yf-HFO-1234zeZ-HCFO-1233zdE-HFO-1243zf

| Organics 0.2 F1233xf + 0.2 F1234yf + 0.2 F1243zf + 0.2 F1234zeE + 0.2 F1233zdE | | Organics 0.96 F1233xf + 0.01 F1234yf + 0.01 F1243zf + 0.01 F1234zeE + 0.01 F1233zdE | | Organics 0.01 F1233xf + 0.96 F1234yf + 0.01 F1243zf + 0.01 F1234zeE + 0.01 F1233zdE | | Organics 0.01 F1233xf + 0.01 F1234yf + 0.96 F1243zf + 0.01 F1234zeE + 0.01 F1233zdE | | Organics 0.01 F1233xf + 0.01 F1234yf + 0.01 F1243zf + 0.96 F1234zeE + 0.01 F1233zdE | | Organics 0.01 F1233xf + 0.01 F1234yf + 0.01 F1243zf + 0.01 F1234zeE + 0.96 F1233zdE | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.6 | 0 | 1.7 | 0 | 6.6 | 0 | 5.7 | 0 | 1.9 | 0 | 1.4 |
| 0.05 | 4.7 | 0.05 | 2.8 | 0.05 | 7.6 | 0.05 | 6.7 | 0.05 | 3.0 | 0.05 | 2.6 |
| 0.1 | 4.7 | 0.1 | 2.8 | 0.1 | 7.6 | 0.1 | 6.7 | 0.1 | 3.0 | 0.1 | 2.6 |
| 0.15 | 4.7 | 0.15 | 2.8 | 0.15 | 7.6 | 0.15 | 6.7 | 0.15 | 3.0 | 0.15 | 2.6 |
| 0.2 | 4.7 | 0.2 | 2.8 | 0.2 | 7.6 | 0.2 | 6.7 | 0.2 | 3.0 | 0.2 | 2.6 |
| 0.25 | 4.7 | 0.25 | 2.8 | 0.25 | 7.6 | 0.25 | 6.7 | 0.25 | 3.0 | 0.25 | 2.6 |
| 0.3 | 4.7 | 0.3 | 2.8 | 0.3 | 7.6 | 0.3 | 6.7 | 0.3 | 3.0 | 0.3 | 2.6 |

-continued

| | | | | | | | | | | | |
|---|---|---|---|---|---|---|---|---|---|---|---|
| 0.35 | 4.7 | 0.35 | 2.8 | 0.35 | 7.6 | 0.35 | 6.7 | 0.35 | 3.0 | 0.35 | 2.5 |
| 0.4 | 4.7 | 0.4 | 2.8 | 0.4 | 7.6 | 0.4 | 6.7 | 0.4 | 3.0 | 0.4 | 2.5 |
| 0.45 | 4.7 | 0.45 | 2.8 | 0.45 | 7.6 | 0.45 | 6.7 | 0.45 | 3.0 | 0.45 | 2.5 |
| 0.5 | 4.7 | 0.5 | 2.8 | 0.5 | 7.6 | 0.5 | 6.7 | 0.5 | 3.0 | 0.5 | 2.5 |
| 0.55 | 4.7 | 0.55 | 2.8 | 0.55 | 7.6 | 0.55 | 6.7 | 0.55 | 3.0 | 0.55 | 2.5 |
| 0.6 | 4.7 | 0.6 | 2.8 | 0.6 | 7.6 | 0.6 | 6.6 | 0.6 | 3.0 | 0.6 | 2.5 |
| 0.65 | 4.7 | 0.65 | 2.8 | 0.65 | 7.6 | 0.65 | 6.6 | 0.65 | 3.0 | 0.65 | 2.5 |
| 0.7 | 4.7 | 0.7 | 2.8 | 0.7 | 7.6 | 0.7 | 6.5 | 0.7 | 3.0 | 0.7 | 2.5 |
| 0.75 | 4.5 | 0.75 | 2.8 | 0.75 | 7.4 | 0.75 | 6.3 | 0.75 | 3.0 | 0.75 | 2.5 |
| 0.8 | 4.3 | 0.8 | 2.6 | 0.8 | 7.1 | 0.8 | 6.0 | 0.8 | 2.9 | 0.8 | 2.4 |
| 0.85 | 3.9 | 0.85 | 2.4 | 0.85 | 6.5 | 0.85 | 5.5 | 0.85 | 2.7 | 0.85 | 2.3 |
| 0.9 | 3.4 | 0.9 | 2.2 | 0.9 | 5.5 | 0.9 | 4.7 | 0.9 | 2.3 | 0.9 | 2.0 |
| 0.95 | 2.5 | 0.95 | 1.7 | 0.95 | 3.8 | 0.95 | 3.3 | 0.95 | 1.9 | 0.95 | 1.7 |
| 1 | 1.2 | 1 | 1.2 | 1 | 1.2 | 1 | 1.2 | 1 | 1.2 | 1 | 1.2 |

HF-HFO-1234yf-HFC-245cb-HFO-1234zeZ-HFO-1234zeZ-HCFO-1233zdE

| Organics 0.2 F1234yf + 0.2 F245cb + 0.2 F1233zdE + 0.2 F1234zeE + 0.2 F1234zdZ | | Organics 0.96 F1234yf + 0.01 F245cb + 0.01 F1233zdE + 0.01 F1234zeE + 0.01 F1234zeZ | | Organics 0.01 F1234yf + 0.96 F245cb + 0.01 F1233zdE + 0.01 F1234zeE + 0.01 F1234zeZ | | Organics 0.01 F1234yf + 0.01 F245cb + 0.96 F1233zdE + 0.01 F1234zeE + 0.01 F1234zeZ | | Organics 0.01 F1234yf + 0.01 F245cb + 0.01 F1233zdE + 0.96 F1234zeE + 0.01 F1234zeZ | | Organics 0.01 F1234yf + 0.01 F245cb + 0.01 F1233zdE + 0.01 F1234zeE + 0.96 F1234zeZ | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.9 | 0 | 6.7 | 0 | 4.6 | 0 | 1.5 | 0 | 4.6 | 0 | 1.9 |
| 0.05 | 5.0 | 0.05 | 7.6 | 0.05 | 5.8 | 0.05 | 2.6 | 0.05 | 5.8 | 0.05 | 3.0 |
| 0.1 | 5.0 | 0.1 | 7.6 | 0.1 | 5.8 | 0.1 | 2.6 | 0.1 | 5.8 | 0.1 | 3.0 |
| 0.15 | 5.0 | 0.15 | 7.6 | 0.15 | 5.8 | 0.15 | 2.6 | 0.15 | 5.8 | 0.15 | 3.0 |
| 0.2 | 5.0 | 0.2 | 7.6 | 0.2 | 5.8 | 0.2 | 2.6 | 0.2 | 5.8 | 0.2 | 3.0 |
| 0.25 | 5.0 | 0.25 | 7.6 | 0.25 | 5.8 | 0.25 | 2.6 | 0.25 | 5.8 | 0.25 | 3.0 |
| 0.3 | 5.0 | 0.3 | 7.6 | 0.3 | 5.8 | 0.3 | 2.6 | 0.3 | 5.8 | 0.3 | 3.0 |
| 0.35 | 5.0 | 0.35 | 7.6 | 0.35 | 5.8 | 0.35 | 2.6 | 0.35 | 5.8 | 0.35 | 3.0 |
| 0.4 | 5.0 | 0.4 | 7.6 | 0.4 | 5.8 | 0.4 | 2.6 | 0.4 | 5.8 | 0.4 | 3.0 |
| 0.45 | 5.0 | 0.45 | 7.6 | 0.45 | 5.8 | 0.45 | 2.6 | 0.45 | 5.8 | 0.45 | 3.0 |
| 0.5 | 5.0 | 0.5 | 7.6 | 0.5 | 5.8 | 0.5 | 2.6 | 0.5 | 5.7 | 0.5 | 3.0 |
| 0.55 | 5.0 | 0.55 | 7.6 | 0.55 | 5.8 | 0.55 | 2.6 | 0.55 | 5.7 | 0.55 | 3.0 |
| 0.6 | 5.0 | 0.6 | 7.6 | 0.6 | 5.8 | 0.6 | 2.6 | 0.6 | 5.6 | 0.6 | 3.0 |
| 0.65 | 5.0 | 0.65 | 7.6 | 0.65 | 5.8 | 0.65 | 2.6 | 0.65 | 5.5 | 0.65 | 3.0 |
| 0.7 | 5.1 | 0.7 | 7.6 | 0.7 | 5.8 | 0.7 | 2.6 | 0.7 | 5.4 | 0.7 | 3.0 |
| 0.75 | 5.0 | 0.75 | 7.5 | 0.75 | 5.8 | 0.75 | 2.6 | 0.75 | 5.1 | 0.75 | 3.0 |
| 0.8 | 4.7 | 0.8 | 7.1 | 0.8 | 5.8 | 0.8 | 2.5 | 0.8 | 4.8 | 0.8 | 2.9 |
| 0.85 | 4.3 | 0.85 | 6.5 | 0.85 | 5.8 | 0.85 | 2.3 | 0.85 | 4.3 | 0.85 | 2.7 |
| 0.9 | 3.7 | 0.9 | 5.5 | 0.9 | 5.0 | 0.9 | 2.0 | 0.9 | 3.6 | 0.9 | 2.4 |
| 0.95 | 2.7 | 0.95 | 3.8 | 0.95 | 3.5 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

-continued

| HF-HFO-1234yf-HFC-245cb-HFO-1234zeZ-HCFO-1233zeE-HFO-1243zf | | | | | | | | | | | |
|---|---|---|---|---|---|---|---|---|---|---|---|
| Organics 0.2 F1234yf + 0.2 F245cb + 0.2 F1243zf + 0.2 F1234zeE + 0.2 F1233zdE | | Organics 0.96 F1234yf + 0.01 F245cb + 0.01 F1243zf + 0.01 F1234zeE + 0.01 F1233zdE | | Organics 0.01 F1234yf + 0.96 F245cb + 0.01 F1243zf + 0.01 F1234zeE + 0.01 F1233zdE | | Organics 0.01 F1234yf + 0.01 F245cb + 0.96 F1243zf + 0.01 F1234zeE + 0.01 F1233zdE | | Organics 0.01 F1234yf + 0.01 F245cb + 0.01 F1243zf + 0.96 F1234zeE + 0.01 F1233zdE | | Organics 0.01 F1234yf + 0.01 F245cb + 0.01 F1243zf + 0.01 F1234zeE + 0.96 F1233zdE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.8 | 0 | 6.7 | 0 | 4.7 | 0 | 5.8 | 0 | 4.9 | 0 | 1.5 |
| 0.05 | 5.9 | 0.05 | 7.7 | 0.05 | 5.8 | 0.05 | 6.7 | 0.05 | 5.8 | 0.05 | 2.6 |
| 0.1 | 5.9 | 0.1 | 7.7 | 0.1 | 5.8 | 0.1 | 6.8 | 0.1 | 5.8 | 0.1 | 2.6 |
| 0.15 | 5.9 | 0.15 | 7.7 | 0.15 | 5.8 | 0.15 | 6.8 | 0.15 | 5.8 | 0.15 | 2.6 |
| 0.2 | 5.9 | 0.2 | 7.7 | 0.2 | 5.8 | 0.2 | 6.8 | 0.2 | 5.8 | 0.2 | 2.6 |
| 0.25 | 5.9 | 0.25 | 7.6 | 0.25 | 5.8 | 0.25 | 6.8 | 0.25 | 5.8 | 0.25 | 2.6 |
| 0.3 | 5.9 | 0.3 | 7.6 | 0.3 | 5.8 | 0.3 | 6.8 | 0.3 | 5.8 | 0.3 | 2.6 |
| 0.35 | 5.9 | 0.35 | 7.6 | 0.35 | 5.8 | 0.35 | 6.8 | 0.35 | 5.8 | 0.35 | 2.6 |
| 0.4 | 5.9 | 0.4 | 7.7 | 0.4 | 5.8 | 0.4 | 6.7 | 0.4 | 5.8 | 0.4 | 2.6 |
| 0.45 | 5.9 | 0.45 | 7.7 | 0.45 | 5.8 | 0.45 | 6.7 | 0.45 | 5.8 | 0.45 | 2.6 |
| 0.5 | 5.9 | 0.5 | 7.7 | 0.5 | 5.8 | 0.5 | 6.7 | 0.5 | 5.8 | 0.5 | 2.6 |
| 0.55 | 5.9 | 0.55 | 7.7 | 0.55 | 5.8 | 0.55 | 6.7 | 0.55 | 5.7 | 0.55 | 2.6 |
| 0.6 | 5.9 | 0.6 | 7.7 | 0.6 | 5.8 | 0.6 | 6.7 | 0.6 | 5.7 | 0.6 | 2.6 |
| 0.65 | 5.9 | 0.65 | 7.7 | 0.65 | 5.8 | 0.65 | 6.6 | 0.65 | 5.6 | 0.65 | 2.6 |
| 0.7 | 5.9 | 0.7 | 7.6 | 0.7 | 5.8 | 0.7 | 6.5 | 0.7 | 5.4 | 0.7 | 2.6 |
| 0.75 | 5.7 | 0.75 | 7.5 | 0.75 | 5.8 | 0.75 | 6.4 | 0.75 | 5.2 | 0.75 | 2.6 |
| 0.8 | 5.4 | 0.8 | 7.2 | 0.8 | 5.8 | 0.8 | 6.1 | 0.8 | 4.8 | 0.8 | 2.5 |
| 0.85 | 5.0 | 0.85 | 6.6 | 0.85 | 5.8 | 0.85 | 5.6 | 0.85 | 4.3 | 0.85 | 2.3 |
| 0.9 | 4.2 | 0.9 | 5.5 | 0.9 | 5.0 | 0.9 | 4.8 | 0.9 | 3.6 | 0.9 | 2.1 |
| 0.95 | 3.0 | 0.95 | 3.8 | 0.95 | 3.5 | 0.95 | 3.4 | 0.95 | 2.6 | 0.95 | 1.7 |
| 1 | 1.2 | 1 | 1.2 | 1 | 1.2 | 1 | 1.2 | 1 | 1.2 | 1 | 1.2 |

| HF-HFO-1234yf-HFC-245cb-HFO-1234zeZ-HCFO-1233zdE-HFO-1243zf | | | | | | | | | | | |
|---|---|---|---|---|---|---|---|---|---|---|---|
| Organics 0.2 F1234yf + 0.2 F245cb + 0.2 F1243zf + 0.2 F1234zeZ + 0.2 F1233zdE | | Organics 0.96 F1234yf + 0.01 F245cb + 0.01 F1243zf + 0.01 F1234zeZ + 0.01 F1233zdE | | Organics 0.01 F1234yf + 0.96 F245cb + 0.01 F1243zf + 0.01 F1234zeZ + 0.01 F1233zdE | | Organics 0.01 F1234yf + 0.01 F245cb + 0.96 F1243zf + 0.01 F1234zeZ + 0.01 F1233zdE | | Organics 0.01 F1234yf + 0.01 F245cb + 0.01 F1243zf + 0.96 F1234zeZ + 0.01 F1233zdE | | Organics 0.01 F1234yf + 0.01 F245cb + 0.01 F1243zf + 0.01 F1234zeZ + 0.96 F1233zdE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.2 | 0 | 6.7 | 0 | 4.6 | 0 | 5.8 | 0 | 1.9 | 0 | 1.5 |
| 0.05 | 5.3 | 0.05 | 7.6 | 0.05 | 5.8 | 0.05 | 6.7 | 0.05 | 3.0 | 0.05 | 2.6 |
| 0.1 | 5.3 | 0.1 | 7.6 | 0.1 | 5.8 | 0.1 | 6.7 | 0.1 | 3.0 | 0.1 | 2.6 |
| 0.15 | 5.3 | 0.15 | 7.6 | 0.15 | 5.8 | 0.15 | 6.7 | 0.15 | 3.0 | 0.15 | 2.6 |
| 0.2 | 5.3 | 0.2 | 7.6 | 0.2 | 5.8 | 0.2 | 6.7 | 0.2 | 3.0 | 0.2 | 2.6 |
| 0.25 | 5.3 | 0.25 | 7.6 | 0.25 | 5.8 | 0.25 | 6.7 | 0.25 | 3.0 | 0.25 | 2.6 |
| 0.3 | 5.3 | 0.3 | 7.6 | 0.3 | 5.8 | 0.3 | 6.7 | 0.3 | 3.0 | 0.3 | 2.6 |

-continued

| | | | | | | | | | | | |
|---|---|---|---|---|---|---|---|---|---|---|---|
| 0.35 | 5.3 | 0.35 | 7.6 | 0.35 | 5.8 | 0.35 | 6.7 | 0.35 | 3.0 | 0.35 | 2.6 |
| 0.4 | 5.3 | 0.4 | 7.6 | 0.4 | 5.8 | 0.4 | 6.7 | 0.4 | 3.0 | 0.4 | 2.6 |
| 0.45 | 5.3 | 0.45 | 7.6 | 0.45 | 5.8 | 0.45 | 6.7 | 0.45 | 3.0 | 0.45 | 2.6 |
| 0.5 | 5.3 | 0.5 | 7.6 | 0.5 | 5.8 | 0.5 | 6.7 | 0.5 | 3.0 | 0.5 | 2.6 |
| 0.55 | 5.3 | 0.55 | 7.6 | 0.55 | 5.8 | 0.55 | 6.7 | 0.55 | 3.0 | 0.55 | 2.6 |
| 0.6 | 5.3 | 0.6 | 7.6 | 0.6 | 5.8 | 0.6 | 6.7 | 0.6 | 3.0 | 0.6 | 2.6 |
| 0.65 | 5.3 | 0.65 | 7.6 | 0.65 | 5.8 | 0.65 | 6.6 | 0.65 | 3.0 | 0.65 | 2.6 |
| 0.7 | 5.3 | 0.7 | 7.6 | 0.7 | 5.8 | 0.7 | 6.5 | 0.7 | 3.0 | 0.7 | 2.6 |
| 0.75 | 5.2 | 0.75 | 7.5 | 0.75 | 5.8 | 0.75 | 6.4 | 0.75 | 3.0 | 0.75 | 2.6 |
| 0.8 | 5.0 | 0.8 | 7.2 | 0.8 | 5.8 | 0.8 | 6.1 | 0.8 | 3.0 | 0.8 | 2.5 |
| 0.85 | 4.6 | 0.85 | 6.6 | 0.85 | 5.8 | 0.85 | 5.6 | 0.85 | 2.9 | 0.85 | 2.3 |
| 0.9 | 3.9 | 0.9 | 5.5 | 0.9 | 5.0 | 0.9 | 4.7 | 0.9 | 2.7 | 0.9 | 2.0 |
| 0.95 | 2.9 | 0.95 | 3.8 | 0.95 | 3.5 | 0.95 | 3.4 | 0.95 | 2.4 | 0.95 | 1.7 |
| 1 | 1.2 | 1 | 1.2 | 1 | 1.2 | 1 | 1.2 | 1 | 1.2 | 1 | 1.2 |

| HF-HFO-1234yf-HFO-1234zeE-HFO-1234zeZ-HCFO-1233zdE-HFO-1243zf | | | | | | | | | | | |
|---|---|---|---|---|---|---|---|---|---|---|---|
| Organics 0.2 F1234yf + 0.2 F1243zf + 0.2 F1233zdE 0.2 F1234zeE + 0.2 F1234zeZ | | Organics 0.96 F1234yf + 0.01 F1243zf + 0.01 F1233zdE + 0.01 F1234zeE + 0.01 F1234zeZ | | Organics 0.01 F1234yf + 0.96 F1243zf + 0.01 F1233zdE + 0.01 F1234zeE + 0.01 F1234zeZ | | Organics 0.01 F1234yf + 0.01 F1243zf + 0.96 F1233zdE + 0.01 F1234zeE + 0.01 F1234zeZ | | Organics 0.01 F1234yf + 0.01 F1243zf + 0.01 F1233zdE + 0.96 F1234zeE + 0.01 F1234zeZ | | Organics 0.01 F1234yf + 0.01 F1243zf + 0.01 F1233zdE + 0.01 F1234zeE + 0.96 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.2 | 0 | 6.7 | 0 | 5.8 | 0 | 1.5 | 0 | 4.8 | 0 | 1.9 |
| 0.05 | 5.3 | 0.05 | 7.6 | 0.05 | 6.7 | 0.05 | 2.6 | 0.05 | 5.8 | 0.05 | 3.0 |
| 0.1 | 5.3 | 0.1 | 7.6 | 0.1 | 6.7 | 0.1 | 2.6 | 0.1 | 5.8 | 0.1 | 3.0 |
| 0.15 | 5.3 | 0.15 | 7.6 | 0.15 | 6.7 | 0.15 | 2.6 | 0.15 | 5.8 | 0.15 | 3.0 |
| 0.2 | 5.3 | 0.2 | 7.6 | 0.2 | 6.7 | 0.2 | 2.6 | 0.2 | 5.8 | 0.2 | 3.0 |
| 0.25 | 5.3 | 0.25 | 7.6 | 0.25 | 6.7 | 0.25 | 2.6 | 0.25 | 5.8 | 0.25 | 3.0 |
| 0.3 | 5.3 | 0.3 | 7.6 | 0.3 | 6.7 | 0.3 | 2.6 | 0.3 | 5.8 | 0.3 | 3.0 |
| 0.35 | 5.3 | 0.35 | 7.6 | 0.35 | 6.7 | 0.35 | 2.6 | 0.35 | 5.8 | 0.35 | 3.0 |
| 0.4 | 5.3 | 0.4 | 7.6 | 0.4 | 6.7 | 0.4 | 2.6 | 0.4 | 5.8 | 0.4 | 3.0 |
| 0.45 | 5.3 | 0.45 | 7.6 | 0.45 | 6.7 | 0.45 | 2.6 | 0.45 | 5.8 | 0.45 | 3.0 |
| 0.5 | 5.3 | 0.5 | 7.6 | 0.5 | 6.7 | 0.5 | 2.6 | 0.5 | 5.8 | 0.5 | 3.0 |
| 0.55 | 5.3 | 0.55 | 7.6 | 0.55 | 6.7 | 0.55 | 2.6 | 0.55 | 5.7 | 0.55 | 3.0 |
| 0.6 | 5.2 | 0.6 | 7.6 | 0.6 | 6.7 | 0.6 | 2.6 | 0.6 | 5.6 | 0.6 | 3.0 |
| 0.65 | 5.2 | 0.65 | 7.6 | 0.65 | 6.6 | 0.65 | 2.6 | 0.65 | 5.5 | 0.65 | 3.0 |
| 0.7 | 5.2 | 0.7 | 7.6 | 0.7 | 6.5 | 0.7 | 2.6 | 0.7 | 5.4 | 0.7 | 3.0 |
| 0.75 | 5.0 | 0.75 | 7.5 | 0.75 | 6.3 | 0.75 | 2.6 | 0.75 | 5.1 | 0.75 | 3.0 |
| 0.8 | 4.7 | 0.8 | 7.1 | 0.8 | 6.1 | 0.8 | 2.5 | 0.8 | 4.8 | 0.8 | 2.9 |
| 0.85 | 4.3 | 0.85 | 6.5 | 0.85 | 5.6 | 0.85 | 2.3 | 0.85 | 4.3 | 0.85 | 2.7 |
| 0.9 | 3.7 | 0.9 | 5.5 | 0.9 | 4.7 | 0.9 | 2.0 | 0.9 | 3.6 | 0.9 | 2.4 |
| 0.95 | 2.7 | 0.95 | 3.8 | 0.95 | 3.4 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

Example 14: Temperature and Pressure Range of Systems with 6 Compounds

| System with 6 compounds | Boiling point range Temperature ° C. | Pressure bar abs |
|---|---|---|
| HF-HCFO-1233xf-HFC-245cb-HFO-1234zeE-HFO-1234zeZ-HCFO-1233zdE | 0 to 40 | ~0.9 to ~9.0 |
| HF-HCFO-1233xf-HFC-245cb-HFO-1234zeE-HCFO-1233zdE-HFO-1243zf | 0 to 40 | ~0.9 to ~10.3 |
| HF-HCFO-1233xf-HFC-245cb-HFO-1234zeZ-HCFO-1233zdE-HFO-1243zf | 0 to 40 | ~1.0 to ~10.3 |
| HF-HCFO-1233xf-HFO-1234zeE-HFO-1234zeZ-HCFO-1233zdE-HFO-1243zf | 0 to 40 | ~0.9 to ~10.3 |
| HF-HFC-245cb-HFO-1234zeE-HFO-1234zeZ-HCFO-1233zdE-HFO-1243zf | 0 to 40 | ~0.9 to ~10.3 |
| HF-HCFO-1233xf-HFO-1234yf-HFC-245cb-HFO-1234zeE-HCFO-1233zdE | 0 to 40 | ~0.9 to ~11.6 |
| HF-HCFO-1233xf-HFO-1234yf-HFC-245cb-HFO-1234zeZ-HCFO-1233zdE | 0 to 40 | ~0.9 to ~11.5 |
| HF-HCFO-1233xf-HFO-1234yf-HFC-245cb-HCFO-1233zdE-HFO-1243zf | 0 to 40 | ~0.9 to ~11.6 |
| HF-HCFO-1233xf-HFO-1234yf-HFO-1234zeE-HFO-1234zeZ-HCFO-1233zdE | 0 to 40 | ~0.9 to ~11.5 |
| HF-HFCO-1233xf-HFO-1234yf-HFO-1234zeE-HCFO-1233zdE-HFO-1243zf | 0 to 40 | ~0.9 to ~11.6 |
| HF-HCFO-1233xf-HFO-1234yf-HFO-1234zeZ-HCFO-1233zdE-HFO-1243zf | 0 to 40 | ~0.9 to ~11.6 |
| HF-HFO-1234yf-HFC-245cb-HFO-1234zeE-HFO-1234zeZ-HCFO-1233zdE | 0 to 40 | ~0.9 to ~11.6 |
| HF-HFO-1234yf-HFC-245cb-HFO-1234zeE-HCFO-1233zdE-HFO-1243zf | 0 to 40 | ~1.0 to ~11.7 |
| HF-HFO-1234yf-HFC-245cb-HFO-1234zeZ-HCFO-1233zdE-HFO-1243zf | 0 to 40 | ~0.9 to ~11.6 |
| HF-HFO-1234yf-HFO-1234zeE-HFO-1234zeZ-HCFO-1233zdE-HFO-1243zf | 0 to 40 | ~0.9 to ~11.6 |

Example 15: Decantation Range of Systems with 6 Compounds

| System with 6 compounds | Decantation ranges Mass percentage of HF Isotherm 0° C. | Isotherm 25° C. | Isotherm 40° C. |
|---|---|---|---|
| HF-HCFO-1233xf-HFC-245cb-HFO-1234zeE-HFO-1234zeZ-HCFO-1233zdE | 5-75 | 5-70 | 10-65 |
| HF-HCFO-1233xf-HFC-245cb-HFO-1234zeE-HCFO-1233zdE-HFO-1243zf | 5-75 | 5-70 | 15-50 |
| HF-HCFO-1233xf-HFC-245cb-HFO-1234zeZ-HCFO-1233zdE-HFO-1243zf | 5-75 | 5-70 | 10-65 |
| HF-HCFO-1233xf-HFO-1234zeE-HFO-1234zeZ-HCFO-1233zdE-HFO-1243zf | 5-75 | 5-65 | 10-55 |
| HF-HFC-245cb-HFO-1234zeE-HFO-1234zeZ-HCFO-1233zdE-HFO-1243zf | 5-75 | 5-70 | 15-50 |
| HF-HCFO-1233xf-HFO-1234yf-HFC-245cb-HFO-1234zeE-HCFO-1233zdE | 5-75 | 5-70 | 15-55 |
| HF-HCFO-1233xf-HFO-1234yf-HFC-245cb-HFO-1234zeZ-HCFO-1233zdE | 5-75 | 5-75 | 10-65 |
| HF-HCFO-1233xf-HFO-1234yf-HFC-245cb-HCFO-1233zdE-HFO-1243zf | 5-75 | 5-70 | 15-55 |
| HF-HCFO-1233xf-HFO-1234yf-HFO-1234zeE-HFO-1234zeZ-HCFO-1233zdE | 5-75 | 5-65 | 10-55 |
| HF-HFCO-1233xf-HFO-1234yf-HFO-1234zeE-HCFO-1233zdE-HFO-1243zf | 5-70 | 10-75 | * |
| HF-HCFO-1233xf-HFO-1234yf-HFO-1234zeZ-HCFO-1233zdE-HFO-1243zf | 5-75 | 5-70 | 10-55 |
| HF-HFO-1234yf-HFC-245cb-HFO-1234zeE-HFO-1234zeZ-HCFO-1233zdE | 5-75 | 5-70 | 15-55 |
| HF-HFO-1234yf-HFC-245cb-HFO-1234zeE-HCFO-1233zdE-HFO-1243zf | 5-75 | 10-65 | * |
| HF-HFO-1234yf-HFC-245cb-HFO-1234zeZ-HCFO-1233zdE-HFO-1243zf | 5-75 | 10-70 | 15-55 |
| HF-HFO-1234yf-HFO-1234zeE-HFO-1234zeZ-HCFO-1233zdE-HFO-1243zf | 5-70 | 10-65 | * |

Example 16: Systems with Seven Compounds, Isotherm at 25° C.

HF - HCFO-1233xf - HFC-245cb - HCFO-1233zdE - HFO-1234zeE - HFO-1234zeZ - HFO-1243zf

| Organics 0.15 F1233xf + 0.17 F245cb + 0.17 F1233zdE + 0.17 F1234zeE + 0.17 F1234zeZ + 0.17 F1243zf | | Organics 0.95 F1233xf + 0.01 F245cb + 0.01 F1233zdE + 0.01 F1234zeE + 0.01 F1234zeZ + 0.01 F1243zf | | Organics 0.01 F1233xf + 0.95 F245cb + 0.01 F1233zdE + 0.01 F1234zeE + 0.01 F1234zeZ + 0.01 F1243zf | | Organics 0.01 F1233xf + 0.01 F245cb + 0.95 F1233zdE + 0.01 F1234zeE + 0.01 F1234zeZ + 0.01 F1243zf | | Organics 0.01 F1233xf + 0.01 F245cb + 0.01 F1233zdE + 0.95 F1234zeE + 0.01 F1234zeZ + 0.01 F1243zf | | Organics 0.01 F1233xf + 0.01 F245cb + 0.01 F1233zdE + 0.01 F1234zeE + 0.95 F1234zeZ + 0.01 F1243zf | | Organics 0.01 F1233xf + 0.01 F245cb + 0.01 F1233zdE + 0.01 F1234zeE + 0.95 F1234zeZ + 0.01 F1243zf | |
|---|---|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.5 | 0 | 1.7 | 0 | 4.6 | 0 | 1.5 | 0 | 4.8 | 0 | 5.7 | 0 | 1.9 |
| 0.05 | 4.6 | 0.05 | 2.8 | 0.05 | 5.7 | 0.05 | 2.6 | 0.05 | 5.7 | 0.05 | 6.7 | 0.05 | 3.0 |
| 0.1 | 4.6 | 0.1 | 2.8 | 0.1 | 5.7 | 0.1 | 2.6 | 0.1 | 5.8 | 0.1 | 6.7 | 0.1 | 3.0 |
| 0.15 | 4.6 | 0.15 | 2.8 | 0.15 | 5.7 | 0.15 | 2.6 | 0.15 | 5.8 | 0.15 | 6.7 | 0.15 | 3.0 |
| 0.2 | 4.6 | 0.2 | 2.8 | 0.2 | 5.7 | 0.2 | 2.6 | 0.2 | 5.8 | 0.2 | 6.7 | 0.2 | 3.0 |
| 0.25 | 4.6 | 0.25 | 2.8 | 0.25 | 5.8 | 0.25 | 2.6 | 0.25 | 5.8 | 0.25 | 6.7 | 0.25 | 3.0 |
| 0.3 | 4.6 | 0.3 | 2.8 | 0.3 | 5.8 | 0.3 | 2.6 | 0.3 | 5.8 | 0.3 | 6.7 | 0.3 | 3.0 |
| 0.35 | 4.6 | 0.35 | 2.8 | 0.35 | 5.8 | 0.35 | 2.6 | 0.35 | 5.8 | 0.35 | 6.7 | 0.35 | 3.0 |
| 0.4 | 4.6 | 0.4 | 2.8 | 0.4 | 5.8 | 0.4 | 2.6 | 0.4 | 5.8 | 0.4 | 6.7 | 0.4 | 3.0 |
| 0.45 | 4.6 | 0.45 | 2.8 | 0.45 | 5.8 | 0.45 | 2.6 | 0.45 | 5.7 | 0.45 | 6.7 | 0.45 | 3.0 |
| 0.5 | 4.6 | 0.5 | 2.8 | 0.5 | 5.8 | 0.5 | 2.6 | 0.5 | 5.7 | 0.5 | 6.7 | 0.5 | 3.0 |
| 0.55 | 4.6 | 0.55 | 2.8 | 0.55 | 5.8 | 0.55 | 2.6 | 0.55 | 5.7 | 0.55 | 6.6 | 0.55 | 3.0 |
| 0.6 | 4.6 | 0.6 | 2.8 | 0.6 | 5.8 | 0.6 | 2.6 | 0.6 | 5.6 | 0.0 | 6.6 | 0.6 | 3.0 |
| 0.65 | 4.6 | 0.65 | 2.8 | 0.65 | 5.8 | 0.65 | 2.6 | 0.65 | 5.5 | 0.65 | 6.6 | 0.65 | 3.0 |
| 0.7 | 4.6 | 0.7 | 2.8 | 0.7 | 5.8 | 0.7 | 2.6 | 0.7 | 5.3 | 0.7 | 6.5 | 0.7 | 3.0 |
| 0.75 | 4.5 | 0.75 | 2.8 | 0.75 | 5.8 | 0.75 | 2.6 | 0.75 | 5.1 | 0.75 | 6.3 | 0.75 | 3.0 |
| 0.8 | 4.2 | 0.8 | 2.6 | 0.8 | 5.8 | 0.8 | 2.4 | 0.8 | 4.8 | 0.8 | 6.0 | 0.8 | 2.9 |
| 0.85 | 3.9 | 0.85 | 2.4 | 0.85 | 5.8 | 0.85 | 2.3 | 0.85 | 4.3 | 0.85 | 5.5 | 0.85 | 2.7 |
| 0.9 | 3.3 | 0.9 | 2.2 | 0.9 | 4.9 | 0.9 | 2.0 | 0.9 | 3.6 | 0.9 | 4.7 | 0.9 | 2.4 |
| 0.95 | 2.5 | 0.95 | 1.8 | 0.95 | 3.5 | 0.95 | 1.7 | 0.95 | 2.6 | 0.95 | 3.3 | 0.95 | 1.0 |
| 1 | 1.2 | 1 | 1.2 | 1 | 1.2 | 1 | 1.2 | 1 | 1.2 | 1 | 1.2 | 1 | 1.2 |

HF - HCFO-1233xf - HFO-1234yf - HFC-245cb - HCFO-1233zdE - HFO-1234zeE - HFO-1234zeZ

| Organics 0.15 F1233xf + 0.17 F1234yf + 0.17 F245cb + 0.17 F1233zdE + 0.17 F1234zeE + 0.17 F1234zeZ | | Organics 0.01 F1233xf + 0.95 F1234yf + 0.01 F245cb + 0.01 F1233zdE + 0.01 F1234zeE + 0.01 F1234zeZ | | Organics 0.01 F1233xf + 0.01 F1234yf + 0.95 F245cb + 0.01 F1233zdE + 0.01 F1234zeE + 0.01 F1234zeZ | | Organics 0.01 F1233xf + 0.01 F1234yf + 0.01 F245cb + 0.95 F1233zdE + 0.01 F1234zeE + 0.01 F1234zeZ | | Organics 0.01 F1233xf + 0.01 F1234yf + 0.01 F245cb + 0.01 F1233zdE + 0.95 F1234zeE + 0.01 F1234zeZ | | Organics 0.01 F1233xf + 0.01 F1234yf + 0.01 F245cb + 0.01 F1233zdE + 0.01 F1234zeE + 0.95 F1234zeZ | | Organics 0.95 F1233xf + 0.01 F1234yf + 0.01 F245cb + 0.01 F1233zdE + 0.01 F1234zeE + 0.01 F1234zeZ | |
|---|---|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.6 | 0 | 6.6 | 0 | 4.6 | 0 | 1.5 | 0 | 4.8 | 0 | 1.9 | 0 | 1.7 |
| 0.05 | 4.7 | 0.05 | 7.6 | 0.05 | 5.8 | 0.05 | 2.6 | 0.05 | 5.8 | 0.05 | 3.0 | 0.05 | 2.8 |
| 0.1 | 4.7 | 0.1 | 7.6 | 0.1 | 5.8 | 0.1 | 2.6 | 0.1 | 5.8 | 0.1 | 3.0 | 0.1 | 2.8 |
| 0.15 | 4.7 | 0.15 | 7.6 | 0.15 | 5.8 | 0.15 | 2.6 | 0.15 | 5.8 | 0.15 | 3.0 | 0.15 | 2.8 |
| 0.2 | 4.7 | 0.2 | 7.6 | 0.2 | 5.8 | 0.2 | 2.6 | 0.2 | 5.8 | 0.2 | 3.0 | 0.2 | 2.8 |

-continued

| | | | | | | | | | | | | | |
|---|---|---|---|---|---|---|---|---|---|---|---|---|---|
| 0.25 | 4.7 | 0.25 | 7.6 | 0.25 | 5.8 | 0.25 | 2.6 | 0.25 | 5.8 | 0.25 | 3.0 | 0.25 | 2.8 |
| 0.3 | 4.7 | 0.3 | 7.6 | 0.3 | 5.8 | 0.3 | 2.6 | 0.3 | 5.8 | 0.3 | 3.0 | 0.3 | 2.8 |
| 0.35 | 4.7 | 0.35 | 7.6 | 0.35 | 5.8 | 0.35 | 2.6 | 0.35 | 5.8 | 0.35 | 3.0 | 0.35 | 2.8 |
| 0.4 | 4.7 | 0.4 | 7.6 | 0.4 | 5.8 | 0.4 | 2.6 | 0.4 | 5.8 | 0.4 | 3.0 | 0.4 | 2.8 |
| 0.45 | 4.7 | 0.45 | 7.6 | 0.45 | 5.8 | 0.45 | 2.6 | 0.45 | 5.7 | 0.45 | 3.0 | 0.45 | 2.8 |
| 0.5 | 4.7 | 0.5 | 7.6 | 0.5 | 5.8 | 0.5 | 2.6 | 0.5 | 5.7 | 0.5 | 3.0 | 0.5 | 2.8 |
| 0.55 | 4.7 | 0.55 | 7.6 | 0.55 | 5.8 | 0.55 | 2.6 | 0.55 | 5.7 | 0.55 | 3.0 | 0.55 | 2.8 |
| 0.6 | 4.7 | 0.6 | 7.6 | 0.6 | 5.8 | 0.6 | 2.6 | 0.6 | 5.6 | 0.6 | 3.0 | 0.6 | 2.8 |
| 0.65 | 4.7 | 0.65 | 7.6 | 0.65 | 5.8 | 0.65 | 2.6 | 0.65 | 5.5 | 0.65 | 3.0 | 0.65 | 2.8 |
| 0.7 | 4.7 | 0.7 | 7.6 | 0.7 | 5.8 | 0.7 | 2.6 | 0.7 | 5.3 | 0.7 | 3.0 | 0.7 | 2.8 |
| 0.75 | 4.8 | 0.75 | 7.4 | 0.75 | 5.5 | 0.75 | 2.6 | 0.75 | 5.1 | 0.75 | 3.0 | 0.75 | 2.8 |
| 0.8 | 4.4 | 0.8 | 7.1 | 0.8 | 5.8 | 0.8 | 2.5 | 0.8 | 4.8 | 0.8 | 2.9 | 0.8 | 2.8 |
| 0.85 | 4.1 | 0.85 | 6.5 | 0.85 | 5.8 | 0.85 | 2.3 | 0.85 | 4.3 | 0.85 | 2.7 | 0.85 | 2.5 |
| 0.9 | 3.5 | 0.9 | 5.5 | 0.9 | 5.0 | 0.9 | 2.0 | 0.9 | 3.6 | 0.9 | 2.4 | 0.9 | 2.2 |
| 0.95 | 2.5 | 0.95 | 3.8 | 0.95 | 3.5 | 0.95 | 1.7 | 0.95 | 2.6 | 0.95 | 1.9 | 0.95 | 1.8 |
| 1 | 1.2 | 1 | 1.2 | 1 | 1.2 | 1 | 1.2 | 1 | 1.2 | 1 | 1.2 | 1 | 1.2 |

HF - HCFO-1233xf - HFO-1234yf - HFC-245cb - HCFO-1233zdE - HFO-1234zeE - HFO-1243zf

| Organics 0.15 F1233xf + 0.17 F1234yf + 0.17 F245cb + 0.17 F1233zdE + 0.17 F1234zeE + 0.17 F1243zf | | Organics 0.01 F1233xf + 0.95 F1234yf + 0.01 F245cb + 0.01 F1233zdE + 0.01 F1234zeE + 0.01 F1243zf | | Organics 0.01 F1233xf + 0.01 F1234yf + 0.95 F245cb + 0.01 F1233zdE + 0.01 F1234zeE + 0.01 F1243zf | | Organics 0.01 F1233xf + 0.01 F1234yf + 0.01 F245cb + 0.95 F1233zdE + 0.01 F1234zeE + 0.01 F1243zf | | Organics 0.01 F1233xf + 0.01 F1234yf + 0.01 F245cb + 0.01 F1233zdE + 0.95 F1234zeE + 0.01 F1243zf | | Organics 0.01 F1233xf + 0.01 F1234yf + 0.01 F245cb + 0.01 F1233zdE + 0.01 F1234zeE + 0.95 F1243zf | | Organics 0.95 F1233xf + 0.01 F1234yf + 0.01 F245cb + 0.01 F1233zdE + 0.01 F1234zeE + 0.01 F1243zf | |
|---|---|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.4 | 0 | 6.6 | 0 | 4.6 | 0 | 1.5 | 0 | 4.8 | 0 | 5.8 | 0 | 1.7 |
| 0.05 | 5.4 | 0.05 | 7.6 | 0.05 | 5.8 | 0.05 | 2.6 | 0.05 | 5.8 | 0.05 | 6.7 | 0.05 | 2.8 |
| 0.1 | 5.4 | 0.1 | 7.6 | 0.1 | 5.8 | 0.1 | 2.6 | 0.1 | 5.8 | 0.1 | 6.7 | 0.1 | 2.8 |
| 0.15 | 5.4 | 0.15 | 7.6 | 0.15 | 5.8 | 0.15 | 2.6 | 0.15 | 5.8 | 0.15 | 6.7 | 0.15 | 2.8 |
| 0.2 | 5.4 | 0.2 | 7.6 | 0.2 | 5.8 | 0.2 | 2.6 | 0.2 | 5.8 | 0.2 | 6.7 | 0.2 | 2.8 |
| 0.25 | 5.4 | 0.25 | 7.6 | 0.25 | 5.8 | 0.25 | 2.6 | 0.25 | 5.8 | 0.25 | 6.7 | 0.25 | 2.8 |
| 0.3 | 5.4 | 0.3 | 7.6 | 0.3 | 5.8 | 0.3 | 2.6 | 0.3 | 5.8 | 0.3 | 6.7 | 0.3 | 2.8 |
| 0.35 | 5.4 | 0.35 | 7.6 | 0.35 | 5.8 | 9.35 | 2.6 | 0.35 | 5.8 | 0.35 | 6.7 | 0.35 | 2.8 |
| 0.4 | 5.4 | 0.4 | 7.6 | 0.4 | 5.3 | 0.4 | 2.6 | 0.4 | 5.8 | 0.4 | 6.7 | 0.4 | 2.8 |
| 0.45 | 5.4 | 0.45 | 7.6 | 0.45 | 5.8 | 0.45 | 2.6 | 0.45 | 5.8 | 0.45 | 6.7 | 0.45 | 2.8 |
| 0.5 | 5.4 | 0.5 | 7.6 | 0.5 | 5.8 | 0.5 | 2.6 | 0.5 | 5.8 | 0.5 | 6.7 | 0.5 | 2.8 |
| 0.55 | 5.4 | 0.55 | 7.6 | 0.55 | 5.8 | 0.55 | 2.6 | 0.55 | 5.7 | 0.55 | 6.7 | 0.55 | 2.8 |
| 0.6 | 5.4 | 0.6 | 7.6 | 0.6 | 5.8 | 0.6 | 2.6 | 0.6 | 5.6 | 0.6 | 6.7 | 0.6 | 2.8 |
| 0.65 | 5.4 | 0.65 | 7.6 | 0.65 | 5.8 | 0.65 | 2.6 | 0.65 | 5.5 | 0.65 | 6.6 | 0.65 | 2.8 |
| 0.7 | 5.4 | 0.7 | 7.6 | 0.7 | 5.8 | 0.7 | 2.6 | 0.7 | 5.4 | 0.7 | 6.5 | 0.7 | 2.8 |
| 0.75 | 5.3 | 0.75 | 7.4 | 0.75 | 5.8 | 0.75 | 2.6 | 0.75 | 5.1 | 0.75 | 6.3 | 0.75 | 2.8 |
| 0.8 | 5.0 | 0.8 | 7.1 | 0.8 | 5.8 | 0.8 | 2.5 | 0.8 | 4.8 | 0.8 | 6.1 | 0.8 | 2.8 |
| 0.85 | 4.5 | 0.85 | 6.5 | 0.85 | 5.8 | 0.85 | 2.3 | 0.85 | 4.3 | 0.85 | 5.6 | 0.85 | 2.7 |
| 0.9 | 3.9 | 0.9 | 5.5 | 0.9 | 5.0 | 0.9 | 2.1 | 0.9 | 3.6 | 0.9 | 4.7 | 0.9 | 2.2 |
| 0.95 | 2.8 | 0.95 | 3.8 | 0.95 | 3.5 | 0.95 | 1.7 | 0.95 | 2.6 | 0.95 | 3.4 | 0.95 | 1.8 |
| 1 | 1.2 | 1 | 1.2 | 1 | 1.2 | 1 | 1.2 | 1 | 1.2 | 1 | 1.2 | 1 | 1.2 |

-continued

| HF - HCFO-1233xf - HFO-1234yf - HFC-245cb - HCFO-1233zdE - HFO-1234zeZ - HFO-1243zf | | | | | | | | | | | | | |
|---|---|---|---|---|---|---|---|---|---|---|---|---|---|
| Organics 0.15 F1233xf + 0.17 F1234yf + 0.17 F245cb + 0.17 F1243zf + 0.17 F1233zdE + 0.17 F1234zeZ | | Organics 0.01 F1233xf + 0.95 F1234yf + 0.01 F245cb + 0.01 F1243zf + 0.01 F1233zdE + 0.01 F1234zeZ | | Organics 0.01 F1233xf + 0.01 F1234yf + 0.95 F245cb + 0.01 F1243zf + 0.01 F1233zdE + 0.01 F1234zeZ | | Organics 0.01 F1233xf + 0.01 F1234yf + 0.01 F245cb + 0.95 F1243zf + 0.01 F1233zdE + 0.01 F1234zeZ | | Organics 0.01 F1233xf + 0.01 F1234yf + 0.01 F245cb + 0.01 F1243zf + 0.95 F1233zdE + 0.01 F1234zeZ | | Organics 0.01 F1233xf + 0.01 F1234yf + 0.01 F245cb + 0.01 F1243zf + 0.01 F1233zdE + 0.95 F1234zeZ | | Organics 0.95 F1233xf + 0.01 F1234yf + 0.01 F245cb + 0.01 F1243zf + 0.01 F1233zdE + 0.01 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.8 | 0 | 6.6 | 0 | 4.6 | 0 | 5.7 | 0 | 1.5 | 0 | 1.9 | 0 | 1.7 |
| 0.05 | 4.9 | 0.05 | 7.6 | 0.05 | 5.8 | 0.05 | 6.7 | 0.05 | 2.6 | 0.05 | 3.0 | 0.05 | 2.8 |
| 0.1 | 4.9 | 0.1 | 7.6 | 0.1 | 5.8 | 0.1 | 6.7 | 0.1 | 2.6 | 0.1 | 3.0 | 0.1 | 2.8 |
| 0.15 | 4.9 | 0.15 | 7.6 | 0.15 | 5.8 | 0.15 | 6.7 | 0.15 | 2.6 | 0.15 | 3.0 | 0.15 | 2.8 |
| 0.2 | 4.9 | 0.2 | 7.6 | 0.2 | 5.8 | 0.2 | 6.7 | 0.2 | 2.6 | 0.2 | 3.0 | 0.2 | 2.8 |
| 0.25 | 4.9 | 0.25 | 7.6 | 0.25 | 5.8 | 0.25 | 6.7 | 0.25 | 2.6 | 0.25 | 3.0 | 0.25 | 2.8 |
| 0.3 | 4.9 | 0.3 | 7.6 | 0.3 | 5.8 | 0.3 | 6.7 | 0.3 | 2.6 | 0.3 | 3.0 | 0.3 | 2.8 |
| 0.35 | 4.9 | 0.35 | 7.6 | 0.35 | 5.8 | 0.35 | 6.7 | 0.35 | 2.6 | 0.35 | 3.0 | 0.35 | 2.8 |
| 0.4 | 4.9 | 0.4 | 7.6 | 0.4 | 5.8 | 0.4 | 6.7 | 0.4 | 2.6 | 0.4 | 3.0 | 0.4 | 2.8 |
| 0.45 | 4.9 | 0.45 | 7.6 | 0.45 | 5.8 | 0.45 | 6.7 | 0.45 | 2.6 | 0.45 | 3.0 | 0.45 | 2.8 |
| 0.5 | 4.9 | 0.5 | 7.6 | 0.5 | 5.8 | 0.5 | 6.7 | 0.5 | 2.6 | 0.5 | 3.0 | 0.5 | 2.8 |
| 0.55 | 4.9 | 0.55 | 7.6 | 0.55 | 5.8 | 0.55 | 6.7 | 0.55 | 2.6 | 0.55 | 3.0 | 0.55 | 2.8 |
| 0.6 | 4.9 | 0.6 | 7.6 | 0.6 | 5.8 | 0.5 | 6.6 | 0.6 | 2.6 | 0.6 | 3.0 | 0.6 | 2.8 |
| 0.65 | 4.9 | 0.65 | 7.6 | 0.65 | 5.8 | 0.65 | 6.6 | 0.65 | 2.6 | 0.65 | 3.0 | 0.65 | 2.8 |
| 0.7 | 4.9 | 0.7 | 7.6 | 0.7 | 5.8 | 0.7 | 6.5 | 0.7 | 2.6 | 0.7 | 3.0 | 0.7 | 2.8 |
| 0.75 | 4.9 | 0.75 | 7.4 | 0.75 | 5.8 | 0.75 | 6.3 | 0.75 | 2.6 | 0.75 | 3.0 | 0.75 | 2.8 |
| 0.8 | 4.7 | 0.8 | 7.1 | 0.8 | 5.8 | 0.8 | 6.0 | 0.8 | 2.5 | 0.8 | 2.9 | 0.8 | 2.7 |
| 0.85 | 4.3 | 0.85 | 6.5 | 0.85 | 5.8 | 0.85 | 5.5 | 0.85 | 2.3 | 0.85 | 2.7 | 0.85 | 2.5 |
| 0.9 | 3.7 | 0.9 | 5.5 | 0.9 | 5.0 | 0.9 | 4.7 | 0.9 | 2.0 | 0.9 | 2.4 | 0.9 | 2.2 |
| 0.95 | 2.7 | 0.95 | 3.8 | 0.95 | 3.5 | 0.95 | 3.3 | 0.95 | 1.7 | 0.95 | 1.9 | 0.95 | 1.8 |
| 1 | 1.2 | 1 | 1.2 | 1 | 1.2 | 1 | 1.2 | 1 | 1.2 | 1 | 1.2 | 1 | 1.2 |

| HF - HCFO-1233xf - HFO-1234yf - HCFO-1233zdE - HFO-1234zeE - HFO-1234zeZ - HF0-1243zf | | | | | | | | | | | | | |
|---|---|---|---|---|---|---|---|---|---|---|---|---|---|
| Organics 0.15 F1233xf + 0.17 F1234yf + 0.17 F1233zdE + 0.17 F1243zf + 0.17 F1234zeE + 0.17 F1234zeZ | | Organics 0.01 F1233xf + 0.95 F1234yf + 0.01 F1233zdE + 0.01 F1243zf + 0.01 F1234zeE + 0.01 F1234zeZ | | Organics 0.01 F1233xf + 0.01 F1234yf + 0.95 F1233zdE + 0.01 F1243zf + 0.01 F1234zeE + 0.01 F1234zeZ | | Organics 0.01 F1233xf + 0.01 F1234yf + 0.01 F1233zdE + 0.95 F1243zf + 0.01 F1234zeE + 0.01 F1234zeZ | | Organics 0.01 F1233xf + 0.01 F1234yf + 0.01 F1233zdE + 0.01 F1243zf + 0.95 F1234zeE + 0.01 F1234zeZ | | Organics 0.01 F1233xf + 0.01 F1234yf + 0.01 F1233zdE + 0.01 F1243zf + 0.01 F1234zeE + 0.95 F1234zeZ | | Organics 0.95 F1233xf + 0.01 F1234yf + 0.01 F1233zdE + 0.01 F1243zf + 0.01 F1234zeE + 0.01 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.9 | 0 | 6.6 | 0 | 1.5 | 0 | 5.7 | 0 | 4.8 | 0 | 1.9 | 0 | 1.7 |
| 0.05 | 5.0 | 0.05 | 7.6 | 0.05 | 2.6 | 0.05 | 6.7 | 0.05 | 5.8 | 0.05 | 3.0 | 0.05 | 2.8 |
| 0.1 | 4.9 | 0.1 | 7.6 | 0.1 | 2.6 | 0.1 | 6.7 | 0.1 | 5.8 | 0.1 | 3.0 | 0.1 | 2.8 |
| 0.15 | 4.9 | 0.15 | 7.6 | 0.15 | 2.6 | 0.15 | 6.7 | 0.15 | 5.8 | 0.15 | 3.0 | 0.15 | 2.8 |

-continued

| | | | | | | | | | | | | | |
|---|---|---|---|---|---|---|---|---|---|---|---|---|---|
| 0.2 | 4.9 | 0.2 | 7.6 | 0.2 | 2.6 | 0.2 | 6.7 | 0.2 | 5.8 | 0.2 | 3.0 | 0.2 | 2.8 |
| 0.25 | 4.9 | 0.25 | 7.6 | 0.25 | 2.6 | 0.25 | 6.7 | 0.25 | 5.8 | 0.25 | 3.0 | 0.25 | 2.8 |
| 0.3 | 4.9 | 0.3 | 7.6 | 0.3 | 2.6 | 0.3 | 6.7 | 0.3 | 5.8 | 0.3 | 3.0 | 0.3 | 2.8 |
| 0.35 | 4.9 | 0.35 | 7.6 | 0.35 | 2.6 | 0.35 | 6.7 | 0.35 | 5.8 | 0.35 | 3.0 | 0.35 | 2.8 |
| 0.4 | 4.9 | 0.4 | 7.6 | 0.4 | 2.6 | 0.4 | 6.7 | 0.4 | 5.8 | 0.4 | 3.0 | 0.4 | 2.8 |
| 0.45 | 4.9 | 0.45 | 7.6 | 0.45 | 2.6 | 0.45 | 6.7 | 0.45 | 5.8 | 0.45 | 3.0 | 0.45 | 2.8 |
| 0.5 | 4.9 | 0.5 | 7.6 | 0.5 | 2.6 | 0.5 | 6.7 | 0.5 | 5.7 | 0.5 | 3.0 | 0.5 | 2.8 |
| 0.55 | 4.9 | 0.55 | 7.6 | 0.55 | 2.6 | 0.55 | 6.7 | 0.55 | 5.7 | 0.55 | 3.0 | 0.55 | 2.8 |
| 0.6 | 4.9 | 0.6 | 7.6 | 0.6 | 2.6 | 0.6 | 6.6 | 0.6 | 5.6 | 0.6 | 3.0 | 0.6 | 2.8 |
| 0.65 | 4.9 | 0.65 | 7.6 | 0.65 | 2.6 | 0.65 | 6.6 | 0.65 | 5.5 | 0.65 | 3.0 | 0.65 | 2.8 |
| 0.7 | 4.8 | 0.7 | 7.6 | 0.7 | 2.6 | 0.7 | 6.5 | 0.7 | 5.3 | 0.7 | 3.0 | 0.7 | 2.8 |
| 0.75 | 4.7 | 0.75 | 7.4 | 0.75 | 2.6 | 0.75 | 6.3 | 0.75 | 5.1 | 0.75 | 3.0 | 0.75 | 2.8 |
| 0.8 | 4.4 | 0.8 | 7.1 | 0.8 | 2.5 | 0.8 | 6.0 | 0.8 | 4.8 | 0.8 | 2.9 | 0.8 | 2.5 |
| 0.85 | 4.0 | 0.85 | 6.5 | 0.85 | 2.3 | 0.85 | 5.5 | 0.85 | 4.3 | 0.85 | 2.7 | 0.85 | 2.5 |
| 0.9 | 3.4 | 0.9 | 5.5 | 0.9 | 2.0 | 0.9 | 4.7 | 0.9 | 3.6 | 0.9 | 2.4 | 0.9 | 2.2 |
| 0.95 | 2.5 | 0.95 | 3.8 | 0.95 | 1.7 | 0.95 | 3.3 | 0.95 | 2.6 | 0.95 | 1.9 | 0.95 | 1.8 |
| 1 | 1.2 | 1 | 1.2 | 1 | 1.2 | 1 | 1.2 | 1 | 1.2 | 1 | 1.2 | 1 | 1.2 |

HF - HFO-1234yf - HFC-245cb - HCFO-1233zdE - HFO-1234zeE - HFO-1234zeZ - HFO-1243zf

| Organics 0.15 F1234yf + 0.17 F245cb + 0.17 F1233zdE + 0.17 F1234zeE + 0.17 F1234zeZ + 0.17 F1243zf | | Organics 0.95 F1234yf + 0.01 F245cb + 0.01 F1233zdE + 0.01 F1234zeE + 0.01 F1234zeZ + 0.01 F1243zf | | Organics 0.01 F1234yf + 0.95 F245cb + 0.01 F1233zdE + 0.01 F1234zeE + 0.01 F1234zeZ + 0.01 F1243zf | | Organics 0.01 F1234yf + 0.01 F245cb + 0.95 F1233zdE + 0.01 F1234zeE + 0.01 F1234zeZ + 0.01 F1243zf | | Organics 0.01 F1234yf + 0.01 F245cb + 0.01 F1233zdE + 0.95 F1234zeE + 0.01 F1234zeZ + 0.01 F1243zf | | Organics 0.01 F1234yf + 0.01 F245cb + 0.01 F1233zdE + 0.01 F1234zeE + 0.01 F1234zeZ + 0.95 F1243zf | | Organics 0.01 F1234yf + 0.01 F245cb + 0.01 F1233zdE + 0.01 F1234zeE + 0.95 F1234zeZ + 0.01 F1243zf | |
|---|---|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.3 | 0 | 6.6 | 0 | 4.6 | 0 | 1.5 | 0 | 4.8 | 0 | 5.8 | 0 | 2.0 |
| 0.05 | 5.3 | 0.05 | 7.6 | 0.06 | 5.8 | 0.05 | 2.6 | 0.05 | 5.8 | 0.05 | 6.7 | 0.05 | 3.1 |
| 0.1 | 5.3 | 0.1 | 7.6 | 0.1 | 5.8 | 0.1 | 2.6 | 0.1 | 5.8 | 0.1 | 6.7 | 0.1 | 3.1 |
| 0.15 | 5.3 | 0.15 | 7.6 | 0.15 | 5.3 | 0.15 | 2.6 | 0.15 | 5.8 | 0.15 | 6.7 | 0.15 | 3.1 |
| 0.2 | 5.3 | 0.2 | 7.6 | 0.2 | 5.8 | 0.2 | 2.6 | 0.2 | 5.8 | 0.2 | 6.7 | 0.2 | 3.1 |
| 0.25 | 5.3 | 0.25 | 7.6 | 0.25 | 5.8 | 0.25 | 2.6 | 0.25 | 5.8 | 0.25 | 6.7 | 0.25 | 3.1 |
| 0.3 | 5.3 | 0.3 | 7.6 | 0.3 | 5.8 | 0.3 | 2.6 | 0.3 | 5.8 | 0.3 | 6.7 | 0.3 | 3.1 |
| 0.35 | 5.3 | 0.35 | 7.6 | 0.35 | 5.8 | 0.35 | 2.6 | 0.35 | 5.8 | 0.35 | 6.7 | 0.35 | 3.1 |
| 0.4 | 5.3 | 0.4 | 7.6 | 0.4 | 5.8 | 0.4 | 2.6 | 0.4 | 5.8 | 0.4 | 6.7 | 0.4 | 3.1 |
| 0.45 | 5.3 | 0.45 | 7.6 | 0.45 | 5.8 | 0.45 | 2.6 | 0.45 | 5.8 | 0.45 | 6.7 | 0.45 | 3.1 |
| 0.5 | 5.3 | 0.5 | 7.6 | 0.5 | 5.8 | 0.5 | 2.6 | 0.5 | 5.8 | 0.5 | 6.7 | 0.5 | 3.1 |
| 0.55 | 5.3 | 0.55 | 7.6 | 0.55 | 5.8 | 0.55 | 2.6 | 0.55 | 5.7 | 0.55 | 6.7 | 0.56 | 3.1 |
| 0.6 | 5.3 | 0.6 | 7.6 | 0.6 | 5.8 | 0.6 | 2.6 | 0.6 | 5.6 | 0.6 | 6.7 | 0.5 | 3.1 |
| 0.65 | 5.3 | 0.65 | 7.6 | 0.65 | 5.8 | 0.65 | 2.6 | 0.65 | 5.5 | 0.65 | 6.6 | 0.65 | 3.1 |
| 0.7 | 5.3 | 0.7 | 7.6 | 0.7 | 5.8 | 0.7 | 2.6 | 0.7 | 5.4 | 0.7 | 6.5 | 0.7 | 3.1 |
| 0.75 | 5.2 | 0.75 | 7.4 | 0.75 | 5.8 | 0.75 | 2.6 | 0.75 | 5.1 | 0.75 | 6.3 | 0.75 | 3.1 |
| 0.8 | 4.9 | 0.8 | 7.1 | 0.8 | 5.8 | 0.8 | 2.5 | 0.8 | 4.8 | 0.8 | 6.1 | 0.8 | 2.9 |
| 0.85 | 4.5 | 0.85 | 6.5 | 0.85 | 5.8 | 0.85 | 2.3 | 0.85 | 4.3 | 0.85 | 5.6 | 0.85 | 2.7 |
| 0.9 | 3.9 | 0.9 | 5.5 | 0.9 | 5.0 | 0.9 | 2.1 | 0.9 | 3.6 | 0.9 | 4.7 | 0.9 | 2.4 |
| 0.95 | 2.8 | 0.95 | 3.8 | 0.95 | 3.5 | 0.95 | 1.7 | 0.95 | 2.6 | 0.95 | 3.4 | 0.95 | 1.9 |
| 1 | 1.2 | 1 | 1.2 | 1 | 1.2 | 1 | 1.2 | 1 | 1.2 | 1 | 1.2 | 1 | 1.2 |

-continued

| HF - HCFC-1233zdE - HCFC-244bb - HFC-245fa - Trifluoropropyne - HFO-1225yeZ - HFO-1225zc | | | | | | | |
|---|---|---|---|---|---|---|---|
| MASSFRAC HF | Organics 0.15 F1233zdE + 0.17 F244bb + 0.17 F245fa + 0.17TFP + 0.17 F1225yeZ + 0.17 F1225zc TOTAL PRES bar | Organics 0.95 F1233zdE + 0.01 F244bb + 0.01 F245fa + 0.01 TFP + 0.01 F1225yeZ + 0.01 F1225zc TOTAL PRES bar | Organics 0.01 F1233zdE + 0.95 F244bb + 0.01 F245fa + 0.01 TFP + 0.01 F1225yeZ + 0.01 F1225zc TOTAL PRES bar | Organics 0.01 F1233zdE + 0.01 F244bb + 0.95 F245fa + 0.01 TFP + 0.01 F1225yeZ + 0.01 F1225zc TOTAL PRES bar | Organics 0.01 F1233zdE + 0.01 F244bb + 0.01 F245fa + 0.95 TFP + 0.01 F1225yeZ + 0.01 F1225zc TOTAL PRES bar | Organics 0.01 F1233zdE + 0.01 F244bb + 0.01 F245fa + 0.01 TFP + 0.95 F1225yeZ + 0.01 F1225zc TOTAL PRES bar | Organics 0.01 F1233zdE + 0.01 F244bb + 0.01 F245fa + 0.01 TFP + 0.01 F1225yeZ + 0.95 F1225zc TOTAL PRES bar |
| 0 | 4.8 | 1.5 | 0.9 | 1.7 | 11.3 | 5.1 | 5.3 |
| 0.05 | 5.9 | 2.6 | 2.1 | 2.8 | 12.1 | 6.2 | 6.2 |
| 0.1 | 5.9 | 2.6 | 2.1 | 2.8 | 12.0 | 6.2 | 6.3 |
| 0.15 | 5.8 | 2.6 | 2.1 | 2.8 | 11.9 | 6.2 | 6.3 |
| 0.2 | 5.8 | 2.6 | 2.1 | 2.8 | 11.8 | 6.2 | 6.3 |
| 0.25 | 5.8 | 2.6 | 2.1 | 2.8 | 11.7 | 6.2 | 6.2 |
| 0.3 | 5.8 | 2.6 | 2.1 | 2.8 | 11.6 | 6.2 | 6.2 |
| 0.35 | 5.8 | 2.6 | 2.1 | 2.8 | 11.5 | 6.2 | 6.2 |
| 0.4 | 5.8 | 2.6 | 2.1 | 2.8 | 11.5 | 6.2 | 6.2 |
| 0.45 | 5.8 | 2.6 | 2.0 | 2.8 | 11.4 | 6.2 | 6.2 |
| 0.5 | 5.7 | 2.6 | 2.0 | 2.8 | 11.5 | 6.2 | 6.2 |
| 0.55 | 5.7 | 2.6 | 2.0 | 2.8 | 11.5 | 6.2 | 6.2 |
| 0.6 | 5.7 | 2.6 | 2.0 | 2.8 | 11.5 | 6.2 | 6.1 |
| 0.65 | 5.6 | 2.6 | 2.0 | 2.8 | 11.5 | 6.2 | 6.0 |
| 0.7 | 5.6 | 2.6 | 2.0 | 2.8 | 11.5 | 6.1 | 5.8 |
| 0.75 | 5.4 | 2.6 | 2.0 | 2.8 | 11.6 | 5.9 | 5.6 |
| 0.8 | 5.1 | 2.5 | 2.0 | 2.7 | 11.3 | 5.6 | 5.2 |
| 0.85 | 4.7 | 2.3 | 2.0 | 2.5 | 10.5 | 5.0 | 4.6 |
| 0.9 | 3.9 | 2.1 | 1.8 | 2.2 | 8.9 | 4.2 | 3.8 |
| 0.95 | 2.8 | 1.7 | 1.6 | 1.8 | 6.0 | 3.0 | 2.7 |
| 1 | 1.2 | 1.2 | 1.2 | 1.2 | 1.2 | 1.2 | 1.2 |

Example 17: Temperature and Pressure Range of Systems with 7 Compounds

| System with 7 compounds | Boiling point range | |
|---|---|---|
| | Temper-rature ° C. | Pressure bar abs |
| HC-HCFO-1233xf-HFC-245cb-HCFO-1233zdE-HFO-1234zeE-HFO-1234zeZ-HFO-1243zf | 0 to 40 | ~0.9 to ~10.3 |
| HF-HCFO-1233xf-HFO-1234yf-HFC-245cb-HCFO-1233zdE-HFO-1234zeE-HFO-1234zeZ | 0 to 40 | ~0.9 to ~11.5 |
| HF-HCFO-1233xf-HFO-1234yf-HFC-245cb-HCFO-1233zdE-HFO-1234zeE-HFO-1243zf | 0 to 40 | ~1.0 to ~11.6 |
| HF-HCFO-1233xf-HFO-1234yf-HFC-245cb-HCFO-1233zdE-HFO-1234zeZ-HFO-1243zf | 0 to 40 | ~0.9 to ~11.5 |
| HF-HCFO-1233xf-HFO-1234yf-HCFO-1233zdE-HFO-1234zeE-HFO-1234zeZ-HFO-1243zf | 0 to 40 | ~0.9 to ~11.5 |
| HF-HFO-1234yf-HFC-245b-HCFO-1233zdE-HFO-1234zeE-HFO-1234zeZ-HFO-1243zf | 0 to 40 | ~1.0 to ~11.6 |
| HF-HCFC-1233zdE-HCFC-244bb-HFC-245fa-Trifluoropropyne-HFO-1225yeZ-HFO-1225zc | 0 to 40 | ~0.7 to ~17.5 |

Example 18: Decantation Range of Systems with 7 Compounds

| System with 7 compounds | Decantation ranges Mass percentage of HF Temperature | | |
|---|---|---|---|
| | 0° C. | 25° C. | 40° C. |
| HC-HCFO-1233xf-HFC-245cb-HCFO-1233zdE-HFO-1234zeE-HFO-1234zeZ-HFO-1243zf | 5-75 | 5-70 | 10-55 |
| HF-HCFO-1233xf-HFO-1234yf-HFC-245cb-HCFO-1233zdE-HFO-1234zeE-HFO-1234zeZ | 5-75 | 5-70 | 10-60 |
| HF-HCFO-1233xf-HFO-1234yf-HFC-245cb-HCFO-1233zdE-HFO-1234zeE-HFO-1243zf | 5-75 | 10-65 | 20 |
| HF-HCFO-1233xf-HFO-1234yf-HFC-245cb-HCFO-1233zdE-HFO-1234zeZ-HFO-1243zf | 5-70 | 5-70 | 10-60 |
| HF-HCFO-1233xf-HFO-1234yf-HCFO-1233zdE-HFO-1234zeE-HFO-1234zeZ-HFO-1243zf | 5-75 | 10-65 | 15-45 |
| HF-HFO-1234yf-HFC-245b-HCFO-1233zdE-HFO-1234zeE-HFO-1234zeZ-HFO-1243zf | 5-75 | 10-65 | * |
| HF-HCFC-1233zdE-HCFC-244bb-HFC-245fa-Trifluoropropyne-HFO-1225yeZ-HFO-1225zc | 5-75 | 5-70 | 10-60 |

Example 19: Systems with 8 Compounds

HF-HCFO-1233xf-HFO-1234yf-HFC-245cb-HCFO-1233zdE-HFO-1234zeE-HFO-1234zeZ-HFO-1243zf

| Organics 0.01 F1233xf + 0.94 F1234yf + 0.01 F245cb + 0.01 F1233zdE + 0.01 F1234zeE + 0.01 F1234zeZ + 0.01 F1243zf | | Organics 0.01 F1233xf + 0.01 F1234yf + 0.94 F245cb + 0.01 F1233zdE + 0.01 F1243zeE + 0.01 F1234zeZ + 0.01 F1243zf | | Organics 0.01 F1233xf + 0.01 F1234yf + 0.01 F245cb + 0.94 F1233zdE + 0.01 F1243zeE + 0.01 F1234zeZ + 0.01 F1243zf | | Organics 0.01 F1233xf + 0.01 F1234yf + 0.01 F245cb + 0.01 F1233zdE + 0.94 F1234zeE + 0.01 F1234zeZ + 0.01 F1243zf | | Organics 0.01 F1233xf + 0.01 F1234yf + 0.01 F245cb + 0.01 F1233zdE + 0.01 F1234zeE + 0.94 F1234zeZ + 0.01 F1243zf | | Organics 0.01 F1233xf + 0.01 F1234yf + 0.01 F245cb + 0.01 F1233zdE + 0.01 F1234zeE + 0.01 F1234zeZ + 0.94 F1243zf | | Organics 0.01 F1233xf + 0.14 F1234yf + 0.14 F245cb + 0.14 F1233zdE + 0.14 F1234zeE + 0.14 F1234zeZ + 0.14 F1243zf | |
|---|---|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.6 | 0 | 4.6 | 0 | 1.5 | 0 | 4.8 | 0 | 2.0 | 0 | 5.7 | 0 | 3.9 |
| 0.05 | 7.6 | 0.05 | 5.8 | 0.05 | 2.5 | 0.05 | 5.8 | 0.05 | 3.1 | 0.05 | 6.7 | 0.05 | 5.0 |
| 0.1 | 7.6 | 0.1 | 5.8 | 0.1 | 2.5 | 0.1 | 5.8 | 0.1 | 3.1 | 0.1 | 6.7 | 0.1 | 5.0 |
| 0.15 | 7.6 | 0.15 | 5.8 | 0.15 | 26 | 0.15 | 5.8 | 0.15 | 3.1 | 0.15 | 6.7 | 0.15 | 5.0 |
| 0.2 | 7.6 | 0.2 | 5.8 | 0.2 | 2.6 | 0.2 | 5.5 | 0.2 | 3 1 | 0.2 | 6.7 | 0.2 | 5.0 |
| 0.25 | 7.6 | 0.25 | 5.8 | 0.25 | 25 | 0.25 | 5.8 | 0.25 | 31 | 0.25 | 6.7 | 0.25 | 5.0 |
| 0.3 | 7.6 | 0.3 | 5.8 | 0.3 | 2.6 | 0.3 | 5.8 | 0.3 | 3.1 | 0.3 | 6.7 | 0.3 | 5.0 |
| 0.35 | 7.6 | 0.35 | 5.8 | 0.35 | 2.6 | 0.35 | 5.8 | 0.35 | 3.1 | 0.35 | 6.7 | 0.35 | 5.0 |
| 0.4 | 7.6 | 0.4 | 5.8 | 0.4 | 2.5 | 0.4 | 5.8 | 0.4 | 3.1 | 0.4 | 6.7 | 0.4 | 5.0 |
| 0.45 | 7.6 | 0.45 | 5.8 | 0.45 | 2.5 | 0.45 | 5.8 | 0.45 | 3.1 | 0.45 | 6.7 | 0.45 | 5.0 |
| 0.5 | 7.6 | 0.5 | 5.8 | 0.5 | 2.6 | 0.5 | 5.7 | 0.5 | 3.1 | 0.5 | 6.7 | 0.5 | 5.0 |
| 0.55 | 7.6 | 0.55 | 5.8 | 0.55 | 2.6 | 0.55 | 5.7 | 0.55 | 3.1 | 0.55 | 6.7 | 0.55 | 5.0 |
| 0.6 | 7.6 | 0.6 | 5.8 | 0.6 | 2.6 | 0.6 | 5.6 | 0.6 | 3.1 | 0.6 | 6.6 | 0.6 | 5.0 |
| 0.65 | 7.6 | 0.65 | 5.8 | 0.65 | 2.6 | 0.65 | 5.5 | 0.65 | 3.1 | 0.65 | 6.6 | 0.65 | 5.0 |
| 0.7 | 7.5 | 0.7 | 5.8 | 0.7 | 2.6 | 0.7 | 5.4 | 0.7 | 3.1 | 0.7 | 6.5 | 0.7 | 5.0 |
| 0.75 | 7.4 | 0.75 | 5.8 | 0.75 | 2.6 | 0.75 | 5.1 | 0.75 | 3.1 | 0.75 | 6.3 | 0.75 | 4.9 |
| 0.8 | 7.1 | 0.8 | 5.8 | 0.8 | 2.5 | 0.8 | 4.8 | 0.8 | 2.9 | 0.8 | 6.0 | 0.8 | 4.6 |
| 0.85 | 6.5 | 0.85 | 5.8 | 0.85 | 2.3 | 0.85 | 4.3 | 0.85 | 2.7 | 0.85 | 5.5 | 0.85 | 4.2 |
| 0.9 | 5.5 | 0.9 | 5.0 | 0.9 | 2.1 | 0.9 | 3.6 | 0.9 | 2.4 | 0.9 | 4.7 | 0.9 | 3.6 |
| 0.95 | 3.8 | 0.95 | 3.5 | 0.95 | 1.7 | 0.95 | 2.6 | 0.95 | 1.9 | 0.95 | 3.3 | 0.95 | 2.6 |
| 1 | 1.2 | 1 | 1.2 | 1 | 1.2 | 1 | 1.2 | 1 | 1.2 | 1 | 1.2 | 1 | 1.2 |

HF-HFO-1234yf-HFC-245cb-HCFO-1233xf-HFO-1234zeE-HFO-1234zeZ-HCFO-1233zdE-HCFC-244bb

| MASSFRAC HF | Organics 0.94 F1233xf + 0.01 F1234yf + 0.01 F245cb + 0.01 F1233zdE + 0.01 F1234zeE + 0.01 F1234zeZ + 0.01 F244bb TOTAL PRESSURE bar | Organics 0.01 F1233xf + 0.94 F1234yf + 0.01 F245cb + 0.01 F1233zdE + 0.01 F1234zeE + 0.01 F1234zeZ + 0.01 F244bb TOTAL PRESSURE bar | Organics 0.01 F1233xf + 0.01 F1234yf + 0.94 F245cb + 0.01 F1233zdE + 0.01 F1234zeE + 0.01 F1234zeZ + 0.01 F244bb TOTAL PRESSURE bar | Organics 0.01 F1233xf + 0.01 F1234yf + 0.01 F245cb + 0.94 F1233zdE + 0.01 F1234zeE + 0.01 F1234zeZ + 0.01 F244bb TOTAL PRESSURE bar | Organics 0.01 F1233xf + 0.01 F1234yf + 0.01 F245cb + 0.01 F1233zdE + 0.94 F1234zeE + 0.01 F1234zeZ + 0.01 F244bb TOTAL PRESSURE bar | Organics 0.01 F1233xf + 0.01 F1234yf + 0.01 F245cb + 0.01 F1233zdE + 0.01 F1234zeE + 0.94 F1234zeZ + 0.01 F244bb TOTAL PRESSURE bar | Organics 0.01 F1233xf + 0.01 F1234yf + 0.01 F245cb + 0.01 F1233zdE + 0.01 F1234zeE + 0.01 F1234zeZ + 0.94 F244bb TOTAL PRESSURE bar | Organics 0.16 F1233xf + 0.14 F1234yf + 0.14 F245cb + 0.14 F1233zdE + 0.14 F1234zeE + 0.14 F1234zeZ + 0.14 F244bb TOTAL PRESSURE bar |
|---|---|---|---|---|---|---|---|---|
| 0 | 1.7 | 6.5 | 4.5 | 1.5 | 4.8 | 1.9 | 0.8 | 3.2 |
| 0.05 | 2.8 | 7.5 | 5.7 | 2.6 | 5.7 | 3.0 | 2.0 | 4.3 |
| 0.1 | 2.8 | 7.5 | 5.7 | 2.6 | 5.7 | 3.0 | 2.0 | 4.3 |

-continued

| | | | | | | | | |
|---|---|---|---|---|---|---|---|---|
| 0.15 | 2.8 | 7.5 | 5.7 | 2.6 | 5.7 | 3.0 | 2.0 | 4.3 |
| 0.2 | 2.8 | 7.5 | 5.7 | 2.6 | 5.7 | 3.0 | 2.0 | 4.3 |
| 0.25 | 2.8 | 7.5 | 5.7 | 2.6 | 5.7 | 3.0 | 2.0 | 4.3 |
| 0.3 | 2.8 | 7.5 | 5.7 | 2.6 | 5.7 | 3.0 | 2.0 | 4.3 |
| 0.35 | 2.8 | 7.5 | 5.7 | 2.6 | 5.7 | 3.0 | 2.0 | 4.3 |
| 0.4 | 2.8 | 7.5 | 5.7 | 2.6 | 5.7 | 3.0 | 2.0 | 4.3 |
| 0.45 | 2.8 | 7.5 | 5.7 | 2.6 | 5.7 | 3.0 | 2.0 | 4.3 |
| 0.5 | 2.8 | 7.5 | 5.7 | 2.6 | 5.7 | 3.0 | 2.0 | 4.3 |
| 0.55 | 2.8 | 7.5 | 5.7 | 2.6 | 5.7 | 3.0 | 2.0 | 4.2 |
| 0.6 | 2.8 | 7.5 | 5.7 | 2.6 | 5.6 | 3.0 | 2.0 | 4.2 |
| 0.65 | 2.8 | 7.5 | 5.7 | 2.6 | 5.5 | 3.0 | 2.0 | 4.2 |
| 0.7 | 2.8 | 7.5 | 5.7 | 2.6 | 5.3 | 3.0 | 2.0 | 4.2 |
| 0.75 | 2.8 | 7.4 | 5.7 | 2.6 | 5.1 | 3.0 | 1.9 | 4.2 |
| 0.8 | 2.6 | 7.0 | 5.7 | 2.4 | 4.7 | 2.9 | 1.9 | 4.0 |
| 0.85 | 2.4 | 6.5 | 5.7 | 2.3 | 4.3 | 2.7 | 1.9 | 3.7 |
| 0.9 | 2.2 | 5.4 | 4.9 | 2.0 | 3.6 | 2.4 | 1.8 | 3.2 |
| 0.95 | 1.8 | 3.8 | 3.5 | 1.7 | 2.6 | 1.9 | 1.6 | 2.4 |
| 1 | 1.2 | 1.2 | 1.2 | 1.2 | 1.2 | 1.2 | 1.2 | 1.2 |

HF-HFO-1234YF-HFC-245CB-HCFO-1233XF-HFO-1234zeZ-HCFO-1233zdE-Trifluoropropyne

| MASSFRAC HF | Organics 0.14 F1234yf + 0.14 F245cb + 0.14 F1233xf + 0.14 F1234zeE + 0.14 F1234zeZ + 0.14 F1233zdE + 0.14 TPF TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 TPF TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 TPF TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 TPF TOTAL PRESSURE bar | Organics 0.01 F1234yf + 0.01 F245cb + 0.01 F1233xf + 0.94 F1234zeE + 0.01 F1234zeZ + 0.01 F1233zdE + 0.01 TPF TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 TPF TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 TPF TOTAL PRESSURE bar | Organics 0.01 F1234yf + 0.01 F245cb + 0.01 F1233xf + 0.01 F1234zeE + 0.01 F1234zeZ + 0.01 F1233zdE + 0.94 TPF TOTAL PRESSURE bar |
|---|---|---|---|---|---|---|---|---|
| 0 | 5.0 | 6.7 | 4.7 | 1.8 | 4.9 | 2.0 | 1.6 | 11.2 |
| 0.05 | 6.0 | 7.6 | 5.8 | 2.9 | 5.6 | 3.1 | 2.7 | 12.0 |
| 0.1 | 6.0 | 7.6 | 5.8 | 2.9 | 5.9 | 3.1 | 2.7 | 11.9 |
| 0.15 | 6.0 | 7.6 | 5.8 | 2.9 | 5.9 | 3.1 | 2.7 | 11.8 |
| 0.2 | 6.0 | 7.6 | 5.8 | 2.9 | 5.9 | 3.1 | 2.7 | 11.7 |
| 0.25 | 6.0 | 7.6 | 5.8 | 2.9 | 5.8 | 3.1 | 2.7 | 11.6 |
| 0.3 | 6.0 | 7.6 | 5.8 | 2.9 | 5.8 | 3.1 | 2.7 | 11.5 |
| 0.35 | 6.0 | 7.6 | 5.8 | 2.9 | 5.8 | 3.1 | 2.7 | 11.5 |
| 0.4 | 6.0 | 7.6 | 5.8 | 2.9 | 5.8 | 3.1 | 2.7 | 11.4 |
| 0.45 | 6.0 | 7.6 | 5.8 | 2.9 | 5.8 | 3.1 | 2.7 | 11.4 |
| 0.5 | 6.0 | 7.6 | 5.8 | 2.9 | 5.8 | 3.1 | 2.7 | 11.4 |
| 0.55 | 6.0 | 7.6 | 5.8 | 2.9 | 5.8 | 3.1 | 2.7 | 11.5 |
| 0.6 | 6.0 | 7.6 | 5.8 | 2.9 | 5.7 | 3.1 | 2.7 | 11.5 |
| 0.65 | 6.0 | 7.6 | 5.8 | 2.9 | 5.6 | 3.1 | 2.7 | 11.5 |

-continued

| | | | | | | | | |
|---|---|---|---|---|---|---|---|---|
| 0.7 | 6.0 | 7.6 | 5.8 | 2.9 | 5.4 | 3.1 | 2.7 | 11.5 |
| 0.75 | 5.9 | 7.5 | 5.8 | 2.9 | 5.2 | 3.1 | 2.7 | 11.5 |
| 0.8 | 5.6 | 7.1 | 5.8 | 2.6 | 4.9 | 3.0 | 2.6 | 11.2 |
| 0.85 | 5.1 | 6.6 | 5.8 | 2.6 | 4.4 | 2.8 | 2.4 | 10.4 |
| 0.9 | 4.3 | 5.5 | 5.0 | 2.2 | 3.6 | 2.4 | 2.1 | 8.8 |
| 0.95 | 3.1 | 3.6 | 3.5 | 1.6 | 2.6 | 1.9 | 1.7 | 5.9 |
| 1 | 1.2 | 1.2 | 1.2 | 1.2 | 1.2 | 1.2 | 1.2 | 1.2 |

HF-HFO-1234YF-hfc-245cb-HCFO-1233xf-HFO-1234zeE-HFO-1234zez-HCFO-1233zdE-HFC-245fa

| MASSFRAC HF | Organics 0.16 F1234yf + 0.14 F245cb + 0.14 F1233xf + 0.14 F1234zeE + 0.14 F1234zeZ + 0.14 F1233zdE + 0.14 F245fa TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 F245fa TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 F245fa TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 F245fa TOTAL PRESSURE bar | Organics 0.01 F1234yf + 0.01 F245cb + 0.01 F1233xf + 0.94 F1234zeE + 0.01 F1234zeZ + 0.01 F1233zdE + 0.01 F245fa TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 F245fa TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 F245fa TOTAL PRESSURE bar | Organics 0.01 F1234yf + 0.01 F245cb + 0.01 F1233xf + 0.01 F1234zeE + 0.01 F1234zeZ + 0.01 F1233zdE + 0.94 F245fa TOTAL PRESSURE bar |
|---|---|---|---|---|---|---|---|---|
| 0 | 3.4 | 6.6 | 4.5 | 1.7 | 4.8 | 1.9 | 1.5 | 1.6 |
| 0.05 | 4.5 | 7.5 | 5.7 | 2.8 | 5.7 | 3.0 | 2.6 | 2.8 |
| 0.1 | 4.5 | 7.5 | 5.7 | 2.8 | 5.7 | 3.0 | 2.6 | 2.8 |
| 0.15 | 4.5 | 7.5 | 5.7 | 2.8 | 5.7 | 3.0 | 2.6 | 2.8 |
| 0.2 | 4.5 | 7.5 | 5.7 | 2.8 | 5.7 | 3.0 | 2.6 | 2.8 |
| 0.25 | 4.5 | 7.5 | 5.7 | 2.8 | 5.7 | 3.0 | 2.6 | 2.8 |
| 0.3 | 4.5 | 7.5 | 5.7 | 2.8 | 5.7 | 3.0 | 2.6 | 2.8 |
| 0.35 | 4.5 | 7.5 | 5.7 | 2.8 | 5.7 | 3.0 | 2.6 | 2.8 |
| 0.4 | 4.5 | 7.5 | 5.7 | 2.8 | 5.7 | 3.0 | 2.6 | 2.8 |
| 0.45 | 4.5 | 7.5 | 5.7 | 2.8 | 5.7 | 3.0 | 2.6 | 2.8 |
| 0.5 | 4.5 | 7.5 | 5.7 | 2.8 | 5.7 | 3.0 | 2.6 | 2.8 |
| 0.55 | 4.5 | 7.5 | 5.7 | 2.8 | 5.6 | 3.0 | 2.6 | 2.8 |
| 0.6 | 4.5 | 7.5 | 5.7 | 2.8 | 5.6 | 3.0 | 2.6 | 2.8 |
| 0.65 | 4.5 | 7.5 | 5.7 | 2.8 | 5.5 | 3.0 | 2.6 | 2.8 |
| 0.7 | 4.5 | 7.5 | 5.7 | 2.8 | 5.3 | 3.0 | 2.6 | 2.8 |
| 0.75 | 4.4 | 7.4 | 5.7 | 2.8 | 5.1 | 3.0 | 2.6 | 2.8 |
| 0.8 | 4.2 | 7.1 | 5.8 | 2.6 | 4.7 | 2.9 | 2.5 | 2.7 |
| 0.85 | 3.9 | 6.5 | 5.7 | 2.5 | 4.3 | 2.7 | 2.3 | 2.5 |
| 0.9 | 3.3 | 5.4 | 4.9 | 2.2 | 3.6 | 2.4 | 2.0 | 2.2 |
| 0.95 | 2.4 | 3.6 | 3.5 | 1.8 | 2.6 | 1.9 | 1.7 | 1.8 |
| 1 | 1.2 | 1.2 | 1.2 | 1.2 | 1.2 | 1.2 | 1.2 | 1.2 |

-continued

| HF-HFO-1234yf-HFC-245cb-HCFO-1233xf-HFO-1234zeE-HFO-1234zeZ-HCFO-1233zdE-HFO-1225yeZ | | | | | | | | |
|---|---|---|---|---|---|---|---|---|
| MASSFRAC HF | Organics<br>0.16 F1234yf +<br>0.14 F245cb +<br>0.14 F1233xf +<br>0.14 F1234zeE +<br>0.14 F1234zeZ +<br>0.14 F1233zdE +<br>0.14 F1225yeZ<br>TOTAL PRESSURE bar | Organics<br>0.94 F1234yf +<br>0.01 F245cb +<br>0.01 F1233xf +<br>0.01 F1234zeE +<br>0.01 F1234zeZ +<br>0.01 F1233zdE +<br>0.01 F1225yeZ<br>TOTAL PRESSURE bar | Organics<br>0.01 F1234yf +<br>0.94 F245cb +<br>0.01 F1233xf +<br>0.01 F1234zeE +<br>0.01 F1234zeZ +<br>0.01 F1233zdE +<br>0.01 F1225yeZ<br>TOTAL PRESSURE bar | Organics<br>0.01 F1234yf +<br>0.01 F245cb +<br>0.94 F1233xf +<br>0.01 F1234zeE +<br>0.01 F1234zeZ +<br>0.01 F1233zdE +<br>0.01 F1225yeZ<br>TOTAL PRESSURE bar | Organics<br>0.01 F1234yf +<br>0.01 F245cb +<br>0.01 F1233xf +<br>0.94 F1234zeE +<br>0.01 F1234zeZ +<br>0.01 F1233zdE +<br>0.01 F1225yeZ<br>TOTAL PRESSURE bar | Organics<br>0.01 F1234yf +<br>0.01 F245cb +<br>0.01 F1233xf +<br>0.01 F1234zeE +<br>0.94 F1234zeZ +<br>0.01 F1233zdE +<br>0.01 F1225yeZ<br>TOTAL PRESSURE bar | Organics<br>0.01 F1234yf +<br>0.01 F245cb +<br>0.01 F1233xf +<br>0.01 F1234zeE +<br>0.01 F1234zeZ +<br>0.94 F1233zdE +<br>0.01 F1225yeZ<br>TOTAL PRESSURE bar | Organics<br>0.01 F1234yf +<br>0.01 F245cb +<br>0.01 F1233xf +<br>0.01 F1234zeE +<br>0.01 F1234zeZ +<br>0.01 F1233zdE +<br>0.94 F1225yeZ<br>TOTAL PRESSURE bar |
| 0 | 3.8 | 6.6 | 4.6 | 1.7 | 4.8 | 1.9 | 1.5 | 5.1 |
| 0.05 | 4.9 | 7.6 | 5.8 | 2.8 | 5.8 | 3.0 | 2.6 | 6.1 |
| 0.1 | 4.9 | 7.6 | 5.8 | 2.8 | 5.8 | 3.0 | 2.6 | 6.1 |
| 0.15 | 4.9 | 7.6 | 5.8 | 2.8 | 5.8 | 3.0 | 2.6 | 6.1 |
| 0.2 | 4.9 | 7.6 | 5.8 | 2.8 | 5.8 | 3.0 | 2.6 | 6.1 |
| 0.25 | 4.9 | 7.6 | 5.8 | 2.8 | 5.8 | 3.0 | 2.6 | 6.1 |
| 0.3 | 4.9 | 7.6 | 5.8 | 2.8 | 5.8 | 3.0 | 2.6 | 6.1 |
| 0.35 | 4.9 | 7.6 | 5.8 | 2.8 | 5.8 | 3.0 | 2.6 | 6.1 |
| 0.4 | 4.9 | 7.6 | 5.8 | 2.8 | 5.8 | 3.0 | 2.6 | 6.1 |
| 0.45 | 4.9 | 7.6 | 5.8 | 2.8 | 5.8 | 3.0 | 2.6 | 6.1 |
| 0.5 | 4.9 | 7.6 | 5.8 | 2.8 | 5.7 | 3.0 | 2.6 | 6.1 |
| 0.55 | 4.9 | 7.6 | 5.8 | 2.8 | 5.7 | 3.0 | 2.6 | 6.1 |
| 0.6 | 4.9 | 7.6 | 5.8 | 2.8 | 5.6 | 3.0 | 2.6 | 6.1 |
| 0.65 | 4.9 | 7.6 | 5.8 | 2.8 | 5.5 | 3.0 | 2.6 | 6.1 |
| 0.7 | 4.9 | 7.5 | 5.8 | 2.8 | 5.3 | 3.0 | 2.6 | 6.0 |
| 0.75 | 5.0 | 7.4 | 5.8 | 2.8 | 5.1 | 3.0 | 2.6 | 5.8 |
| 0.8 | 4.6 | 7.1 | 5.8 | 2.7 | 4.8 | 2.9 | 2.5 | 5.5 |
| 0.85 | 4.2 | 6.5 | 5.8 | 2.5 | 4.3 | 2.7 | 2.3 | 5.0 |
| 0.9 | 3.6 | 5.5 | 4.9 | 2.2 | 3.6 | 2.4 | 2.1 | 4.2 |
| 0.95 | 2.6 | 3.8 | 3.5 | 1.8 | 2.6 | 1.9 | 1.7 | 2.9 |
| 1 | 1.2 | 1.2 | 1.2 | 1.2 | 1.2 | 1.2 | 1.2 | 1.2 |

| HF-HFO-1234yf-HFC-245cb-HCFO-1233xf-HFO-1234zeE-HFO-1234zeZ-HCFC-1233zdE-HFO-1225zc | | | | | | | | |
|---|---|---|---|---|---|---|---|---|
| MASSFRAC HF | Organics<br>0.16 F1234yf +<br>0.14 F245cb +<br>0.14 F1233xf +<br>0.14 F1234zeE +<br>0.14 F1234zeZ +<br>0.14 F1233zdE +<br>0.14 F1225ze<br>TOTAL PRESSURE bar | Organics<br>0.94 F1234yf +<br>0.01 F245cb +<br>0.01 F1233xf +<br>0.01 F1234zeE +<br>0.01 F1234zeZ +<br>0.01 F1233zdE +<br>0.01 F1225ze<br>TOTAL PRESSURE bar | Organics<br>0.01 F1234yf +<br>0.94 F245cb +<br>0.01 F1233xf +<br>0.01 F1234zeE +<br>0.01 F1234zeZ +<br>0.01 F1233zdE +<br>0.01 F1225ze<br>TOTAL PRESSURE bar | Organics<br>0.01 F1234yf +<br>0.01 F245cb +<br>0.94 F1233xf +<br>0.01 F1234zeE +<br>0.01 F1234zeZ +<br>0.01 F1233zdE +<br>0.01 F1225ze<br>TOTAL PRESSURE bar | Organics<br>0.01 F1234yf +<br>0.01 F245cb +<br>0.01 F1233xf +<br>0.94 F1234zeE +<br>0.01 F1234zeZ +<br>0.01 F1233zdE +<br>0.01 F1225ze<br>TOTAL PRESSURE bar | Organics<br>0.01 F1234yf +<br>0.01 F245cb +<br>0.01 F1233xf +<br>0.01 F1234zeE +<br>0.94 F1234zeZ +<br>0.01 F1233zdE +<br>0.01 F1225ze<br>TOTAL PRESSURE bar | Organics<br>0.01 F1234yf +<br>0.01 F245cb +<br>0.01 F1233xf +<br>0.01 F1234zeE +<br>0.01 F1234zeZ +<br>0.94 F1233zdE +<br>0.01 F1225ze<br>TOTAL PRESSURE bar | Organics<br>0.01 F1234yf +<br>0.01 F245cb +<br>0.01 F1233xf +<br>0.01 F1234zeE +<br>0.01 F1234zeZ +<br>0.01 F1233zdE +<br>0.94 F1225ze<br>TOTAL PRESSURE bar |
| 0 | 3.9 | 6.6 | 4.6 | 1.7 | 4.8 | 1.9 | 1.5 | 5.2 |
| 0.05 | 4.9 | 7.6 | 5.8 | 2.8 | 5.8 | 3.0 | 2.6 | 6.2 |
| 0.1 | 4.9 | 7.6 | 5.8 | 2.8 | 5.8 | 3.0 | 2.6 | 6.2 |

-continued

| | | | | | | | | |
|---|---|---|---|---|---|---|---|---|
| 0.15 | 4.9 | 7.6 | 5.8 | 2.8 | 5.8 | 3.0 | 2.6 | 6.2 |
| 0.2 | 4.9 | 7.6 | 5.8 | 2.8 | 5.8 | 3.0 | 2.6 | 6.2 |
| 0.25 | 4.9 | 7.6 | 5.8 | 2.8 | 5.8 | 3.0 | 2.6 | 6.2 |
| 0.3 | 4.9 | 7.6 | 5.8 | 2.8 | 5.8 | 3.0 | 2.6 | 6.2 |
| 0.35 | 4.9 | 7.6 | 5.8 | 2.8 | 5.8 | 3.0 | 2.6 | 6.2 |
| 0.4 | 4.9 | 7.6 | 5.8 | 2.8 | 5.8 | 3.0 | 2.6 | 6.2 |
| 0.45 | 4.9 | 7.6 | 5.8 | 2.8 | 5.8 | 3.0 | 2.6 | 6.2 |
| 0.5 | 4.9 | 7.6 | 5.8 | 2.8 | 5.7 | 3.0 | 2.6 | 6.2 |
| 0.55 | 4.9 | 7.6 | 5.8 | 2.8 | 5.7 | 3.0 | 2.6 | 6.1 |
| 0.6 | 4.9 | 7.6 | 5.8 | 2.8 | 5.6 | 3.0 | 2.6 | 6.0 |
| 0.65 | 4.9 | 7.6 | 5.8 | 2.8 | 5.5 | 3.0 | 2.6 | 5.9 |
| 0.7 | 4.9 | 7.5 | 5.8 | 2.8 | 5.3 | 3.0 | 2.6 | 5.8 |
| 0.75 | 4.8 | 7.4 | 5.8 | 2.8 | 5.1 | 3.0 | 2.6 | 5.5 |
| 0.8 | 4.6 | 7.1 | 5.8 | 2.7 | 4.8 | 2.9 | 2.5 | 5.1 |
| 0.85 | 4.2 | 6.5 | 5.8 | 2.5 | 4.3 | 2.7 | 2.3 | 4.6 |
| 0.9 | 3.5 | 5.5 | 4.9 | 2.2 | 3.6 | 2.4 | 2.1 | 3.8 |
| 0.95 | 2.6 | 3.8 | 3.5 | 1.8 | 2.6 | 1.9 | 1.7 | 2.7 |
| 1 | 1.2 | 1.2 | 1.2 | 1.2 | 1.2 | 1.2 | 1.2 | 1.2 |

Example 20: Temperature and Pressure Range of System with 8 Compounds

| System with 8 compounds | Boiling point range Temperature ° C. | Pressure bar abs |
|---|---|---|
| HF-HCFO-1233xf-HFO-1234yf-HFC-245cb-HCFO-1233zdE-HFO-1234zeE-HFO-1234zeZ-HFO-1243zf | 0 to 40 | ~1.0~11.5 |
| HF-HFO-1234yf-HFC-245cb-HCFO-1233xf-HFO-1234zeE-HFO-1234zeZ-HCFO-1233zdE-HCFC-244bb | 0 to 40 | ~0.7 to ~11.5 |
| HF-HFO-1234yf-HFC-245cb-HCFO-1233xf-HFO-1234zeE-HFO-1234zeZ-HCFO-1233zdE-Trifluoropropyne | 0 to 40 | ~1.0 to ~17.4 |
| HF-HFO-1234yf-HFC-245cb-HCFO-1233xf-HFO-1234zeE-HFO-1234zeZ-HCFO-1233zdE-HFC-245fa | 0 to 40 | ~0.9 to ~11.5 |
| HF-HFO-1234yf-HFC-245cb-HCFO-1233xf-HFO-1234zeE-HFO-1234zeZ-HCFO-1233zdE-HFO-1225yeZ | 0 to 40 | ~1.0 to ~11.5 |
| HF-HFO-1234yf-HFC-245cb-HCFO-1233xf-HFO-1234zeE-HFO-1234zeZ-HCFC-1233zdE-HFO-1225zc | 0 to 40 | ~1.0 to ~11.5 |

Example 21: Decantation Ranges of System with 8 Compounds

| System with 8 compounds | Decantation ranges Mass percentage of HF Temperature 0° C. | 25° C. | 40° C. |
|---|---|---|---|
| HF-HCFO-1233xf-HFO-1234yf-HFC-245cb-HCFO-1233zdE-HFO-1234zeE-HFO-1234zeZ-HFO-1243zf | 5-75% | 5-70% | 15-50% |
| HF-HFO-1234yf-HFC-245cb-HCFO-1233xf-HFO-1234zeE-HFO-1234zeZ-HCFO-1233zdE-HCFC-244bb | 5-80 | 5-75 | 5-70 |
| HF-HFO-1234yf-HFC-245cb-HCFO-1233xf-HFO-1234zeE-HFO-1234zeZ-HCFO-1233zdE-Trifluoropropyne | 5-75 | 10-65 | * |
| HF-HFO-1234yf-HFC-245cb-HCFO-1233xf-HFO-1234zeE-HFO-1234zeZ-HCFO-1233zdE-HFC-245fa | 5-75 | 5-70 | 10-60 |
| HF-HFO-1234yf-HFC-245cb-HCFO-1233xf-HFO-1234zeE-HFO-1234zeZ-HCFO-1233zdE-HFO-1225yeZ | 5-75 | 5-70 | 15-55 |
| HF-HFO-1234yf-HFC-245cb-HCFO-1233xf-HFO-1234zeE-HFO-1234zeZ-HCFC-1233zdE-HFO-1225zc | 5-75 | 5-65 | 15-50 |

Example 22: Systems with 13 Compounds

| HF - HFO-1234yf - HFC-245cb - HCFO-1233xf - HCFO-1233zdE - HFO-1234zeE - HFO-1234zeZ - HFC-1243zf - HCFC-244bb - TFP - HFC-245fa - HFO-1225yeZ - HFO-1225zc | | | | | |
|---|---|---|---|---|---|
| MASSFRAC HF | Organics 0.087 F1234yf + 0.083 F245cb + 0.083 F1233xf + 0.083 F1233zdE + 0.083 F1234zeE + 0.083 F1234zeZ + 0.083 F1243zf + 0.083 F244bb + 0.083 F245fa + 0.083 TFP + 0.083 F1225yeZ + 0.83 F1225zc TOTAL PRESSURE bar | Organics 0.89 F1234yf + 0.01 F245cb + 0.01 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.89 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.01 F1233zdE + 0.08 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.89 F12332dE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar |
| 0 | 4.5 | 6.5 | 1.9 | 4.8 | 1.7 |
| 0.05 | 5.6 | 7.5 | 3.0 | 5.8 | 2.9 |
| 0.1 | 5.6 | 7.5 | 3.0 | 5.8 | 2.9 |
| 0.15 | 5.6 | 7.5 | 3.0 | 5.8 | 2.8 |
| 0.2 | 5.6 | 7.5 | 3.0 | 5.8 | 2.8 |
| 0.25 | 5.6 | 7.5 | 3.0 | 5.8 | 2.8 |
| 0.3 | 5.6 | 7.5 | 3.0 | 5.8 | 2.8 |
| 0.35 | 5.6 | 7.5 | 3.0 | 5.8 | 2.8 |
| 0.4 | 5.6 | 7.5 | 3.0 | 5.8 | 2.8 |
| 0.45 | 5.5 | 7.5 | 3.0 | 5.8 | 2.8 |
| 0.5 | 5.5 | 7.5 | 3.0 | 5.8 | 2.8 |
| 0.55 | 5.5 | 7.5 | 3.0 | 5.7 | 2.8 |
| 0.6 | 5.5 | 7.5 | 3.0 | 5.6 | 2.8 |
| 0.65 | 5.5 | 7.5 | 3.0 | 5.5 | 2.8 |
| 0.7 | 5.4 | 7.5 | 3.0 | 5.4 | 2.8 |
| 0.75 | 5.3 | 7.3 | 3.0 | 5.2 | 2.8 |
| 0.8 | 5.1 | 7.0 | 2.8 | 4.8 | 2.7 |
| 0.85 | 4.6 | 6.4 | 2.6 | 4.3 | 2.5 |

-continued

| HF - HFO-1234yf - HFC-245cb - HCFO-1233xf - HCFO-1233zdE - HFO-1234zeE - HFO-1234zeZ - HFC-1243zf - HCFC-244bb - TFP - HFC-245fa - HFO-1225yeZ - HFO-1225zc | | | | | |
|---|---|---|---|---|---|
| MASSFRAC HF | Organics 0.087 F1234yf + 0.083 F245cb + 0.083 F1233xf + 0.083 F1233zdE + 0.083 F1234zeE + 0.083 F1234zeZ + 0.083 F1243zf + 0.083 F244bb + 0.083 F245fa + 0.083 TFP + 0.083 F1225yeZ + 0.83 F1225zc TOTAL PRESSURE bar | Organics 0.89 F1234yf + 0.01 F245cb + 0.01 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.89 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.01 F1233zdE + 0.08 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.89 F12332dE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar |
| 0.9 | 3.9 | 5.4 | 2.3 | 3.6 | 2.2 |
| 0.95 | 2.8 | 3.7 | 1.8 | 2.6 | 1.8 |
| 1 | 1.2 | 1.2 | 1.2 | 1.2 | 1.2 |

Example 23: Temperature and Pressure Range of System with 13 Compounds

| | Boiling point range | |
|---|---|---|
| System with 13 compounds | Temperature ° C. | Pressure bar abs |
| HF - HFO-1234yf - HFC-245cb - HCFO-1233xf - HCFO-1233zdE - HFO-1234zeE - HFO-1234zeZ - HFC-1243zf - HCFC-244bb - TFP - HFC-245fa - HFO-1225yeZ - HFO-1225zc | 0 to 40 | ~0.7~18.0 |

Example 24: Decantation Ranges of System with 13 Compounds

| | Decantation ranges Mass percentage of HF Temperature | | |
|---|---|---|---|
| System with 13 compounds | 0° C. | 25° C. | 40° C. |
| HF - HFO-1234yf - HFC-245cb - HCFO-1233xf - HCFO-1233zdE - HFO-1234zeE - HFO-1234zeZ - HFC-1243zf - HCFC-244bb - TFP - HFC-245fa - HFO-1225yeZ - HFO-1225zc | 5-75% | 10-70% | 15-60% |

The invention claimed is:

1. An azeotropic or quasi-azeotropic composition comprising hydrogen fluoride, E-3,3,3-trifluoro-1-chloropropene, one or more compounds selected from the group consisting of 1,1,1,2,2-pentafluoropropane, 2,3,3,3-tetrafluoropropene, 3,3,3-trifluoropropene, 3,3,3-trifluoro-2-chloropropene, and 1,3,3,3-tetrafluoropropene, and optionally one or more (hydro)halocarbon compounds comprising between 1 and 3 carbon atoms, in which the boiling point of said composition is between −20° C. and 80° C. and at a pressure of between 0.1 and 44 bar absolute, wherein the composition consisting essentially of hydrogen fluoride, E-3,3,3-trifluoro-1-chloropropene, and 1,1,1,3,3-pentafluoropropane is excluded.

2. An azeotropic or quasi-azeotropic composition comprising hydrogen fluoride, E-3,3,3-trifluoro-1-chloropropene, and one or more compounds selected from the group consisting of 1,1,1,2,2-pentafluoropropane, 2,3,3,3-tetrafluoropropene, 3,3,3-trifluoropropene, 3,3,3-trifluoro-2-chloropropene, 1,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane, in which the boiling point of said composition is between −20° C. and 80° C. and at a pressure of between 0.1 and 44 bar absolute, wherein the composition consisting essentially of hydrogen fluoride, E-3,3,3-trifluoro-1-chloropropene, and 1,1,1,3,3-pentafluoropropane is excluded.

3. The composition as claimed in claim 1, in which the composition comprises hydrogen fluoride, E-3,3,3-trifluoro-1-chloropropene and at least one or more organic compounds chosen from 1,1,1,2,2-pentafluoropropane, E-1,3,3,3-tetrafluoropropene, Z-1,3,3,3-tetrafluoropropene, 3,3,3-trifluoropropene and 3,3,3-trifluoro-2-chloropropene.

4. The composition as claimed in claim 1 wherein the composition is heteroazeotropic or quasi-heteroazeotropic.

5. The composition as claimed in claim 1, in which the composition comprises hydrogen fluoride, E-3,3,3-trifluoro-1-chloropropene, 1,1,1,2,2-pentafluoropropane and optionally a compound chosen from E-1,3,3,3-tetrafluoropropene, Z-1,3,3,3-tetrafluoropropene, 3,3,3-trifluoropropene and 3,3,3-trifluoro-2-chloropropene.

6. The composition as claimed in claim 1, in which the composition comprises hydrogen fluoride, E-3,3,3-trifluoro-1-chloropropene, E-1,3,3,3-tetrafluoropropene, and optionally a compound chosen from Z-1,3,3,3-tetrafluoropropene, 3,3,3-trifluoropropene and 3,3,3-trifluoro-2-chloropropene.

7. The composition as claimed in claim 1, in which the composition comprises a hydrogen fluoride, E-3,3,3-trifluoro-1-chloropropene, Z-1,3,3,3-tetrafluoropropene and optionally a compound chosen from 3,3,3-trifluoropropene and 3,3,3-trifluoro-2-chloropropene.

8. The composition as claimed in claim 1, in which the composition comprises hydrogen fluoride, E-3,3,3-trifluoro-1-chloropropene, 3,3,3-trifluoropropene and optionally 3,3,3-trifluoro-2-chloropropene.

9. The composition as claimed in claim 1, in which the composition comprises hydrogen fluoride, E-3,3,3-trifluoro-1-chloropropene, 3,3,3-trifluoro-2-chloropropene.

10. The composition as claimed in claim 1, in which the composition comprises from 1% to 85% by weight of hydrogen fluoride and from 99% to 15% by weight of the sum of the organic compounds.

11. The composition as claimed in claim 1, in which the composition comprises from 5% to 80% by weight of hydrogen fluoride and from 95% to 20% by weight of the sum of the organic compounds.

12. The composition as claimed in claim 1, in which the boiling point of said composition is between 0° C. and 40° C. and at a pressure of between 0.7 and 18 bar absolute.

13. The composition as claimed in claim 1, in which the boiling point of said composition is between 0° C. and 40° C. and at a pressure of between 0.9 and 12.5 bar absolute.

14. The composition as claimed in claim 1, comprising two or more compounds selected from the group consisting of 1,1,1,2,2-pentafluoropropane, 2,3,3,3-tetrafluoropropene, 3,3,3-trifluoropropene, 3,3,3-trifluoro-2-chloropropene, and 1,3,3,3-tetrafluoropropene.

15. The composition as claimed in claim 1, comprising three or more compounds selected from the group consisting of 1,1,1,2,2-pentafluoropropane, 2,3,3,3-tetrafluoropropene, 3,3,3-trifluoropropene, 3,3,3-trifluoro-2-chloropropene, and 1,3,3,3-tetrafluoropropene.

* * * * *